(12) United States Patent
Harrison et al.

(10) Patent No.: US 10,722,857 B2
(45) Date of Patent: Jul. 28, 2020

(54) ENCAPSULATED PERFUME COMPOSITIONS

(71) Applicant: GIVAUDAN SA, Vernier (CH)

(72) Inventors: Ian Michael Harrison, Poissy (FR); Emmanuel Aussant, Paris (FR); Frederic Blondel, Andrezieux (FR); Guillaume Jeanson, Andrezieux (FR)

(73) Assignee: GIVAUDAN S.A., Vernier (CH)

( * ) Notice: Subject to any disclaimer, the term of this patent is extended or adjusted under 35 U.S.C. 154(b) by 307 days.

(21) Appl. No.: 15/738,997

(22) PCT Filed: Jun. 22, 2016

(86) PCT No.: PCT/EP2016/064344
§ 371 (c)(1),
(2) Date: Dec. 21, 2017

(87) PCT Pub. No.: WO2016/207180
PCT Pub. Date: Dec. 29, 2016

(65) Prior Publication Data
US 2018/0169603 A1 Jun. 21, 2018

(30) Foreign Application Priority Data
Jun. 22, 2015 (GB) .................... 1510940.8

(51) Int. Cl.
| | | |
|---|---|---|
| *A61K 8/11* | (2006.01) | |
| *B01J 13/10* | (2006.01) | |
| *B01J 13/16* | (2006.01) | |
| *C11D 3/50* | (2006.01) | |
| *A61Q 13/00* | (2006.01) | |
| *B01J 13/08* | (2006.01) | |
| *B01J 13/20* | (2006.01) | |
| *B01J 13/14* | (2006.01) | |
| *A61K 8/84* | (2006.01) | |
| *C08G 14/10* | (2006.01) | |
| *C08G 12/32* | (2006.01) | |
| *C08G 12/38* | (2006.01) | |
| *C08G 12/42* | (2006.01) | |

(52) U.S. Cl.
CPC .................. *B01J 13/10* (2013.01); *A61K 8/11* (2013.01); *A61K 8/84* (2013.01); *A61Q 13/00* (2013.01); *B01J 13/08* (2013.01); *B01J 13/14* (2013.01); *B01J 13/16* (2013.01); *B01J 13/206* (2013.01); *C08G 12/32* (2013.01); *C08G 12/38* (2013.01); *C08G 12/428* (2013.01); *C08G 14/10* (2013.01); *C11D 3/505* (2013.01); *A61K 2800/56* (2013.01)

(58) Field of Classification Search
CPC ........ A61K 8/11; A61K 8/84; A61K 2800/56; A61Q 13/00; A61Q 5/00; A61Q 8013/08; B01J 13/08; B01J 13/10; B01J 13/14; B01J 13/16; B01J 13/206; C08G 12/32; C08G 12/38; C08G 12/428; C08G 14/10; C11D 3/0015; C11D 3/505
See application file for complete search history.

(56) References Cited

U.S. PATENT DOCUMENTS

| | | | | |
|---|---|---|---|---|
| 8,119,587 | B2 * | 2/2012 | Cavin | ............ A61K 8/06 510/441 |
| 2016/0166480 | A1 * | 6/2016 | Lei | ............ C11D 17/0039 424/401 |

FOREIGN PATENT DOCUMENTS

| | | |
|---|---|---|
| EP | 2860237 A1 | 4/2015 |
| WO | 0231092 A2 | 4/2002 |
| WO | 2007137441 A1 | 12/2007 |
| WO | 2009153695 A1 | 12/2009 |
| WO | 2011075425 A1 | 6/2011 |
| WO | 2013092375 A1 | 12/2012 |

OTHER PUBLICATIONS

International Search Report and Written Opinion of the International Searching Authority for corresponding application PCT/EP2016/064344 dated Sep. 15, 2016.

* cited by examiner

*Primary Examiner* — Irina S Zemel
(74) *Attorney, Agent, or Firm* — Norris McLaughlin, PA

(57) ABSTRACT

An encapsulated perfume composition comprising at least one perfume-containing aminoplast core-shell microcapsule dispersed in an aqueous suspending medium, the microcapsule being characterized in that it bears a positive charge.

19 Claims, No Drawings

ENCAPSULATED PERFUME COMPOSITIONS

This is an application filed under 35 USC 371 of PCT/EP2016/064344 filed 22 Jun. 2016 which in turn was based on GB 1510940.8 filed 22 Jun. 2015. The applicant claims all available priority benefit to the foregoing applications, and incorporates the entirety of their disclosures herein.

FIELD OF THE INVENTION

The present invention is concerned with an encapsulated perfume composition comprising at least one positively charged, perfume-containing aminoplast core-shell microcapsule suspended in a suspending medium; methods of incorporating said composition into consumer products, and to consumer products, including household care, laundry care and personal care products containing said composition.

BACKGROUND OF THE INVENTION

It is known to employ encapsulated fragrance compositions in consumer products, including household care, personal care, and fabric care products. Perfume compositions are encapsulated for a variety of reasons. Encapsulation isolates and protects perfume ingredients from external suspending media, such as consumer product bases, in which they may be incompatible or unstable. Microcapsules can also be used to increase the efficiency with which perfume ingredients are deposited onto substrates, such as skin, hair, fabrics or hard household surfaces, as well as acting as a means of controlling the spatio-temporal release of perfume.

Aminoplast microcapsules are among the most commonly used encapsulating media for perfume compositions. There are established processes of forming aminoplast microcapsules that are well documented in the prior art. Typically, in a first step an oil-in-water emulsion is formed, consisting of fragrance-containing oil droplets dispersed in an aqueous continuous phase. Thereafter, shell-forming amino-aldehyde pre-condensates contained in the emulsion are caused to form encapsulating polymeric shells around the perfume-containing droplets to form core-shell microcapsules.

Reagents and reaction conditions are selected to ensure the amino-aldehyde pre-condensates undergo poly-condensation and crosslinking to form polymeric shells rapidly around the oil droplets, thereby retaining all, or substantially all, of the perfume ingredients within the droplets and preventing subsequent leakage of encapsulated perfume ingredients from the microcapsules. If the shells are unable to form quickly then it may be impossible to form microcapsules, or if microcapsules can be formed they may be characterized by poor fragrance retention and may be prone to agglomeration.

It is conventional to employ polymers as colloidal stabilizers during microcapsule formation. The polymers function in several ways: They ensure that stable oil-in-water emulsions are formed; they ensure that pre-condensates and cross-linking agents are present at the oil-water interface in high concentration; and they provide a template around which the pre-condensates and cross-linking agents can react to form the encapsulating polymeric shells.

Colloidal stabilizers employed in the preparation of aminoplast microcapsules are anionic or non-ionic polymers, see for example U.S. Pat. No. 8,119,587. Particularly effective colloidal stabilizers are acrylic acid-based copolymers bearing sulphonate groups. Examples of these copolymers are available commercially under the brand LUPASOL (ex BASF), such as LUPASOL PA 140, or LUPASOL VFR. These commercial polymers are exemplary colloidal stabilizers, which are widely employed in the preparation of commercial aminoplast microcapsule compositions. Encapsulated perfume compositions formed using these polymeric stabilizers exhibit a good balance between perfume retention during storage, and perfume performance when deposited on a substrate.

Aminoplast microcapsules prepared by the process described above are typically collected in the form of a slurry comprising a plurality of microcapsules suspended in a suitable suspending medium. The microcapsule slurry may then be used directly in applications, or further processed in a manner known per se. For example, it is conventional to post-coat aminoplast microcapsules with a cationic water-soluble polymer in order to provide them with a net positive charge, the purpose of which coating is to act as a deposition aid and increase the affinity of the microcapsules to substrates of interest, whether that is fabric, or keratinous substrates such as hair or skin, and thereby increase the substantivity of encapsulated perfume ingredients on those surfaces.

Aminoplast microcapsules represent a very popular means of encapsulating perfume compositions because they are highly stable, that is, they are able to efficiently retain fragrance within their cores, both during microcapsule formation and subsequently during storage. Furthermore, they can also bring perfumery benefits to consumer products that would be unattainable by applying neat fragrance directly to a consumer product base.

However, whilst it is expected that an encapsulated perfume composition should deliver leakage stability and perfume benefits in consumer products, in order for customers to perceive these compositions favourably, they must also be easy to use, that is, they should be easy for a customer to handle, store, transport, and the like. More particularly, they should be compatible with, as well as easily and inexpensively incorporated into, consumer product bases. If a customer cannot perform these tasks easily and cost-effectively, the encapsulated perfume composition will not be favourably received.

During the development of an encapsulated perfume composition in the form of a slurry of aminoplast microcapsules, the applicant encountered a problem when attempting to incorporate the slurry into consumer product bases, and more particularly consumer product bases containing cationic surfactants, most notably fabric softener or fabric conditioner bases and hair conditioner bases. More particularly, when attempting to incorporate the slurries into cationic bases, the microcapsules were observed to agglomerate, forming unsightly and disturbing aggregates that could not be dispersed with dilution and/or vigorous stirring.

The applicant set out to address this incorporation problem, and surprisingly found that replacing a conventional anionic sulphonate-containing polymeric stabilizer, with an alternative polymer bearing polyatomic cations, as a colloidal stabilizer, it was not only possible to form a stable microcapsule slurry that provide excellent perfume benefits when deposited on substrates, but it was also possible to incorporate the slurry into a consumer product base, and particularly cationic bases used in fabric conditioners and hair conditioners without any signs of the agglomeration problem.

The applicant was also surprised to find that whereas one might expect a colloidal stabilizer to be substantially washed into the continuous phase during microcapsule formation, sufficient amounts of it were retained and embedded in the microcapsule shells such that the microcapsules were found to bear a positive charge sufficient to ensure that the microcapsules exhibited a high affinity to substrates without it being necessary to carry out conventional post-coating of the microcapsules with cationic deposition aids.

SUMMARY OF THE INVENTION

An encapsulated perfume composition comprising at least one aminoplast core-shell microcapsule dispersed in a suspending medium, the aminoplast microcapsule comprising a perfume-containing core encapsulated in a shell comprising a cross-linked network of an aminoplast resin, wherein the microcapsule is positively charged.

An encapsulated perfume composition comprising at least one aminoplast core-shell microcapsule dispersed in a suspending medium, the aminoplast microcapsule comprising a perfume-containing core encapsulated in a shell comprising a cross-linked network of an aminoplast resin, and dispersed within said resin network there is a polymeric colloidal stabilizer bearing a positive charge.

The use of a polymer bearing a positive charge as a colloidal stabilizer in the preparation of an encapsulated perfume composition comprising at least one aminoplast core-shell microcapsule dispersed in a suspending medium, as hereinabove described.

A method of preparing an encapsulated perfume composition as herein above described, said method comprising the step of forming a dispersion of at least one perfume-containing droplet in a suspending medium in the presence of a positively-charged polymeric colloidal stabilizer, and thereafter causing an encapsulating shell of cross-linked aminoplast resin to form around said at least one droplet.

A method of incorporating an encapsulated perfume composition as herein described into a consumer product, particularly a cationic consumer product base such as a fabric conditioner or hair conditioner, comprising the step of forming an encapsulated perfume composition according to a method set forth herein, and mixing the encapsulated perfume composition into the consumer product.

DETAILED DESCRIPTION OF THE INVENTION

Although it is well known in the art that perfume-containing core shell microcapsules, are prone to leakage of perfume ingredients from their cores and into the external suspending media, and particularly so when the external media contain surfactants, the encapsulated perfume compositions of the present invention exhibit good perfume retention. In particular, encapsulated perfume compositions of the present invention are able to retain greater than 50%, greater than 60%, greater than 70%, and more particularly greater than 80% of the total encapsulated perfume after storage as aqueous slurry at 37 degrees centigrade for a period of 18 months. Furthermore, encapsulated perfume compositions of the present invention are able to retain greater than 50%, greater than 60%, greater than 70%, and more particularly greater than 80% of the total encapsulated perfume after being suspended in a fabric conditioner base at 37 degrees centigrade for a period of 4 weeks.

In addition to good leakage stability, the encapsulated perfume compositions of the present invention also bring desirable perfumery benefits to consumer products incorporating same.

The perfumery benefit that the encapsulated perfume compositions can bring to consumer products is measurable in terms of the perfume intensity that is perceived when a substrate, e.g. fabric, hair or skin is rubbed (i.e. post-rub performance). This is an indication of substantivity and sustained perfume performance. The substantivity of aminoplast core-shell microcapsules on substrates such as skin and hair, and fabrics, such as cotton, cotton mixes, viscose, silk and wool is addressed in the prior art by applying a coating of a cationic deposition aid, such as any of the known cationically-charged polymers, to the microcapsule wall, typically in a post-coating step. Although post-coating can provide benefits in terms of increasing the affinity of microcapsules for a substrate surface, and therefore increasing perfume substantivity, an extra process step, plus the cost of goods, adds to the cost of manufacturing. Furthermore, it may be necessary to use relatively large amounts of cationic polymers in a post-coating step because it will be first necessary for the cationic polymers to neutralize negatively charged microcapsules before conferring upon them a net positive charge.

Post-coating a microcapsule with a cationic deposition aid is also complex and its effect on the rate at which a microcapsule releases its perfume can be unpredictable. In particular, the effectiveness of post-coating and the quality of deposition will depend on the compatibility of the deposition aid with the delicate interfacial chemistry. The microcapsule surface will be competing for the cationic polymer with the suspending medium, which may contain a complex mixture of surfactants and other charged materials. As such, the post-coating may be only partial or complete, and any variability in the thickness of the post-coating can affect the rate at which perfume is released. Still further, the extent and thickness of the coating may also change over time as it sloughs off into the surrounding suspending medium rather than remaining anchored to the surface of the microcapsules.

In encapsulated perfume compositions of the present invention, the positively charged polymer acting as a colloidal stabilizer is embedded in the shell during shell formation, and unlike a post-coating, is resistant to being separated from the shell. The effect of this is that the microcapsules retain a positive charge that is substantially stable over time, and substantially insensitive to the nature of the external suspending medium.

It is a particular feature of the present invention that the encapsulated perfume compositions are characterized in that they contain positively charged microcapsules, which are cationic without the need for coating the microcapsules with a cationic deposition aid, e.g. during a post-coating step.

Accordingly, in an embodiment of the invention there is provided a method of forming an encapsulated perfume composition as herein described, said method comprising the step of forming a dispersion of at least one perfume-containing droplet in a suspending medium in the presence of a positively-charged polymeric colloidal stabilizer, and thereafter causing an encapsulating shell of cross-linked aminoplast resin to form around said at least one droplet.

Of course, whereas using the colloidal stabilizer to impart a net positive charge on the microcapsules has the advantage of avoiding the need for coating the microcapsules by post-coating, and encapsulated perfume compositions described herein that are not post-coated with a deposition aid form a preferred aspect of the present invention, the skilled person can, if it so wishes for any purpose, post-coat the encapsulated perfume composition microcapsules with a cationic deposition aid.

In an embodiment of the invention there is provided an encapsulated perfume composition comprising at least one positively-charged aminoplast core-shell microcapsule dispersed in a suspending medium, comprising a perfume-containing core encapsulated in a shell comprising a cross-linked network of an aminoplast resin, and wherein said at least one microcapsule is not coated with a cationic deposition aid.

The encapsulated perfume composition of the present invention is characterized in that the microcapsules have a positive zeta potential, that is, the microcapsules carries a net positive charge.

In a more particular embodiment, the positive zeta potential may be 25 mV or greater.

In a still more particular embodiment, the encapsulated perfume composition is characterized in that the microcapsules have a zeta potential of above 50 mV+/−5 mV.

50 mV represents a rather high zeta potential for microcapsules generally, and aminoplast microcapsules in particular, and it is an indication of the extent to which the microcapsules can resist agglomeration.

Zeta Potential is a term that is well known in the art. It is a term that is used to describe the apparent electrostatic potential generated by any electrically charged objects, such as microcapsules, in suspension, as measured by specific measurement techniques. A detailed discussion of the theoretical basis and practical relevance of the zeta-potential can be found, e.g., in "Zeta Potential in Colloid Sciences" (Robert. J. Hunter; Academic Press, London 1981, 1988). The zeta-potential of an object is measured at some distance from the surface of the object and is generally not equal to and lower than the electrostatic potential at the surface itself. Nevertheless, its value provides a suitable measure of the capability of the object to establish electrostatic interactions with other objects present in the solution, such as surfactants, polyelectrolytes and surfaces.

Methods and apparatus for measuring zeta potential are well known in the art. In the present case, applicant measured the zeta-potential of the microcapsules by the phase analysis light scattering method, using a Zetasizer Nano Z instrument (Malvern).

The zeta-potential of the microcapsules were measured in an aqueous buffer at pH 7. A suitable buffer system is an aqueous solution of $KH_2PO_4/Na_2HPO_4$. A more detailed description of the measurement is provided in the examples, below.

Measuring zeta potential can provide an indication of how firmly the positively charged colloidal stabilizer appears to be entrapped within the aminoplast resin shell of the microcapsules. For example, the applicant measured the zeta potential of a suspension of microcapsules, filtered them, washed them and reconstituted them before repeating the zeta potential measurement, and it was found that the zeta potential before and after washing remained remarkably constant at +50 mV+/−5 mV.

Not only was it entirely surprising that a positively charged polymer could act as a colloidal stabilizer in the preparation of the encapsulated perfume compositions, and also impart sufficient net positive charge on the microcapsules to enhance their affinity towards substrates and improve post-rub performance, its use also simplified the manufacturing process because it was not necessary to employ conventional post-coating treatment of capsules with cationic deposition aids.

Still further, in addition to post-rub performance, increasingly customers are looking for perfume intensity without the need to apply any mechanical force (i.e. rubbing) to a substrate (so-called "pre-rub" performance). Customers perceive pre-rub performance as delivering an up-front freshness to consumer products that is particularly desirable in fabric detergents and conditioners, as well as shampoos, and other personal cleansing compositions. The use of a positively charged polymer as a colloidal stabilizer in the formation of encapsulated perfume compositions, at least did not diminish pre-rub perfume impact, and in some cases improved it.

The use of a colloidal stabilizer is important in the preparation of aminoplast core-shell microcapsules. It helps to control the quality of the shell, which in turn will have a direct bearing on the microcapsule stability perfume performance in use. As stated above, it is conventional to employ anionic colloidal stabilizers, and indeed, highly performing anionic colloidal stabilizers based on sulphonate-functionalized acrylic polymers are available commercially under the trade mark LUPASOL PA 140 or LUPASOL VFR (both ex BASF). It was entirely surprising, therefore, that one could replace these highly performing and conventional anionic materials with the positively charged colloidal stabilizers employed in the present invention, and still produce encapsulated perfume compositions exhibiting not only good post-rub fragrance intensity, but also a good pre-rub intensity. Indeed, consumer products containing the encapsulated perfume composition of the present invention can deliver desirable perfumery benefits at all stages of application of a consumer product, e.g. wet stage, pre-rub and post-rub, compared with anionic aminoplast microcapsules.

In exercising the present invention, the positively charged polymer employed as a colloidal stabilizer may be an ampholytic polymer, which bears polyatomic cations, and more particularly an ampholytic co-polymer, which bears polyatomic cations.

In an embodiment of the invention, the colloidal stabilizer is an ampholytic co-polymer comprising 1 to 99 mol % of a cationic unit; and 1 to 99 mol % of a unit that can form anions.

In a more particular embodiment, the co-polymer may be a terpolymer comprising 1 to 99 mol % of a cationic unit; and 1 to 99 mol % of a unit that can form anions. More particularly still, the terpolymer comprising 1 to 99 mol % of a cationic unit; 1 to 99 mol % of a unit that can form anions; and 0 to 50 mol % of a non-ionic unit.

In an embodiment of the invention the colloidal stabilizer is an ampholytic co-polymer comprising 2 to 99 mol % still more particularly 30 to 95 mol %, and more particularly still 60 to 90 mol % of a cationic unit; and 1 to 98 mol %, more particularly 5 to 70 mol %, still more particularly 10 to 40 mol % of a unit that can form anions; and 0 to 50 mol %, and more particularly 0.1 to 5 mol % of a non-ionic unit.

By "unit" is meant a divalent moiety of a polymer, which is derived from the reaction of a particular monomer, thus, a cationic unit is derived from a cationic monomer, a unit that can form anions is derived from a monomer containing a functional group that can be present in anionic form, and a non-ionic unit is derived from a non-ionic monomer.

In an embodiment of the invention, the ampholytic polymer contains more cationic units than it does units that can form anions, and as such, is characterized in that it has a net positive charge.

In an embodiment of the invention, the polyatomic cations are pH independent.

In an embodiment of the invention, the polyatomic cations are provided by quaternary ammonium groups.

In an embodiment of the invention the cationic unit is derived from a monomer bearing quaternary ammonium ion functionality, said monomer being selected from acrylamide, acrylic, vinyl, allyl or maleic. In particular and in a non-limiting way, the cationic monomer is preferably selected from the group consisting of quaternized dimethylaminoethyl acrylate (ADAME), quaternized dimethylaminoethyl methacrylate (MADAME), dimethyldiallyl ammonium chloride (DADMAC), acrylamidopropyltrimethylammonium chloride (APTAC) and methacrylamidopropyltrimethylammonium chloride (MAPTAC). The most preferred cationic monomer is MAPTAC.

In an embodiment of the invention, the unit that can form anions is derived from a monomer selected from the group consisting of acrylic based monomers, include acrylic acid, methacrylic acid, itaconic acid, crotonic acid, maleic acid, fumaric acid and strong-acid monomers, for example monomers with a sulfonic or a phosphonic acid-type function such as 2-acrylamido-2-methylpropane sulfonic acid, vinylsulfonic acid, vinylphosphonic acid, allylsulfonic acid, allylphosphonic acid, styrene sulfonic acid. The acrylic based monomer may also be any water-soluble salts of these monomers; wherein the salt is a salt of an alkali metal, an alkaline-earth metal or an ammonium. The most preferred acrylic based monomer is acrylic acid, methacrylic acid, or a water soluble salt thereof.

In an embodiment of the invention, the non-ionic unit is derived from a non-ionic monomer selected from the group consisting of water-soluble vinyl monomers, and more particularly acrylamide, methacrylamide, N-isopropylacrylamide, N N-dimethylacrylamide, N-methylolacrylamide. N-vinylformamide, N-vinyl acetamide, N-vinylpyridine and/or N-vinylpyrrolidone can also be used. The preferred non-ionic monomer is acrylamide.

In a particular embodiment, the colloidal stabilizer is an ampholytic co-polymer formed from a cationic monomer containing quaternary ammonium groups; and a monomer that can form anions, more particularly a monomer that is based on acrylic acid, methacrylic acid or a derivative thereof.

In a more particular embodiment, the ampholytic co-polymer is a copolymer of acrylic acid or methacrylic acid, and acrylamidopropyltrimethylammonium chloride (APTAC) or methacrylamidopropyltrimethylammonium chloride (MAPTAC).

In a still more particular embodiment, the ampholytic copolymer is a terpolymer formed from acrylic acid monomer, MAPTAC monomer and acrylamide monomer.

In a more preferred embodiment, the acrylic acid/MAPTAC copolymer, and more particularly the terpolymer, is formed by reacting 1 to 2 molar equivalents of acrylic acid monomer with 4 molar equivalents of the MAPTAC monomer, more particularly 1 molar equivalent of acrylic acid monomer to 4 molar equivalents of MAPTAC monomer, and still more particularly 1.6 molar equivalents of acrylic acid monomer to 4 molar equivalents of MAPTAC monomer.

In an embodiment of the invention the copolymer has a molecular weight of at least 100,000 g/mol, and more particularly at least 500,000 g/mol.

The amount of ampholytic polymer that may be employed in an encapsulated perfume composition according to the present invention may be from 1 to 20 wt % and more particularly 2 to 10 wt % based on the weight of the composition.

The ampholytic polymer can be prepared using polymerization techniques that are well known to a person skilled in the art. These known polymerization techniques include solution polymerization; gel polymerization; precipitation polymerization; inverse emulsion polymerization; aqueous emulsion polymerization; suspension polymerization; and micellar polymerization.

The ampholytic polymer can be structured by at least one structuring agent, which may be chosen from the group comprising polyethylenically unsaturated monomers (having at least two unsaturated functional groups such as for example vinyl, allyl, and acrylic), and compounds having epoxy functional groups. For instance, such structuring agents include methylene bisacrylamide (MBA), triallyamine and polyethylene glycol diacrylate. Alternatively, macro initiators such as polyperoxides, polyazo compounds and polytransfer agents such as polymercaptan polymers may be used.

Another aspect of the invention relates to the method of preparing encapsulated perfume compositions.

Microcapsules are formed when a shell-forming material is caused to poly-condense around perfume-containing oil droplets to form an aminoplast resin shell, which can be cross-linked with a suitable cross-linker.

Suitable shell-forming material is well known in the art. Particularly useful shell-forming materials are any of the amino-aldehyde pre-condensates known in the art. The amino-aldehyde pre-condensate may be a reaction product, such as a polymer or copolymer of at least one amine, such as urea, thiourea, alkyl urea, 6-substituted-2,4-diamino-1,3,5-triazines such as benzoguanamine or glycoluril, and melamine; and at least one aldehyde, such us formaldehyde, acetaldehyde, glyoxal or glutaraldehyde.

In a preferred embodiment, melamine-formaldehyde pre-condensate is used in the formation of aminoplast microcapsules. Melamine-formaldehyde pre-condensate is formed by the reaction of melamine with formaldehyde to form methylolated melamine. Methylolated melamine may also be treated with methanol to form methoxymethylated methylol melamine.

Suitable cross-linkers for use in the preparation of the aminoplast resin shell are aliphatic, aromatic or polymeric polyols. Suitable polyols may be selected from the group consisting of phenol, 3,5-dihydroxy toluene, Bisphenol A, resorcinol, hydroquinone, xylenol, polyhydroxy naphthalene and polyphenols produced by the degradation of cellulose and humic acids. Examples of suitable aliphatic polyols include, but are not limited to 2,2-dimethyl-1,3-propane diol, 1,1,1-tris-(hydroxymethyl)-propane, pentaerythritol, sorbitol, sugars and the like.

The use of cross-linkers improves microcapsule stability, increases perfume retention and reduces loss of perfume through leakage.

A particularly preferred cross-linker is resorcinol. Resorcinol may react with aldehydes, such as formaldehyde to form mixtures of methylolated resorcinol with various degrees of substitution.

The aminoplast resin shell has an inter-linked and complex structure, which is believed to contain amino-aldehyde condensates and cross-linker condensates. The relative amounts of these condensates will be determined by the amounts of pre-condensates and cross-linkers employed in any poly-condensation reaction.

Shell-forming materials and cross linkers are disclosed in U.S. Pat. No. 8,119,587, which is hereby incorporated by reference.

Encapsulated perfume compositions according to the present invention are typically formed by a process of poly-condensation.

It is a common feature of an encapsulation process that it requires the perfume ingredients to be encapsulated to be dispersed in an aqueous phase containing various mixtures of pre-condensates, stabilizing polymers, surfactants, cross-linking agents, and the like, prior to formation of the capsule shell. These ingredients may be mixed together and dispersed in the aqueous phase in any order. However, in accordance with the present invention the emulsification step is undertaken in the presence of the positively charged polymeric colloidal stabilizer described herein.

In an embodiment of the invention, the encapsulation process proceeds by forming an oil-in-water emulsion of perfume oil under moderate-to-high shear in the presence of the colloidal stabilizer, shell-forming amino-aldehyde pre-condensate, as well as cross-linker.

Reaction conditions, such as temperature, stirring speed and the geometry of the mixer may be selected to obtain a desired average microcapsule size range and microcapsule size distribution, the selection of which parameters are well within the purview of those of skill of the art.

Thereafter, the mixture, under continual stirring, can be adjusted to a pH of about 3 to 4, more particularly 3.2 to 3.8 by the addition of a suitable acid, for example a Bronsted acid such as formic acid. The temperature can be increased at this stage to about 75 degrees centigrade+/−5 degrees centigrade, or more particularly up to 90+/−5 degrees centigrade. During this step, the encapsulating shells condense around the perfume oil droplets and are hardened by cross-linking. Cross-linking is initiated when the temperature is increased to a temperature of about 35° C. or above.

A formaldehyde scavenger, such as ethylene urea, may be added during this step.

The resultant microcapsule slurry is cooled, and the suspended microcapsules are stabilized using a suspending agent. The pH of the slurry may also be adjusted at this stage to within a range of about 5 to 7, more particularly 5.7 to 6.7 with the addition of a suitable alkaline material, such as ammonia. At this stage, it is also conventional to add a biocide to the slurry.

In an embodiment of the present invention there is provided a method of forming an encapsulated perfume composition as herein described, the method comprising the step of forming a dispersion of at least one perfume-containing droplet in an aqueous suspending medium in the presence of a positively-charged polymeric colloidal stabilizer, and thereafter initiating an encapsulating shell of cross-linked aminoplast resin to form around said at least one droplet, and hardening of the shell by cross-linking.

In a more particular embodiment the method comprises the steps of:

a) providing an aqueous phase comprising a positively charged polymeric colloidal stabilizer, a shell-forming melamine formaldehyde pre-condensate and optionally a cross-linker;

b) providing an oil phase comprising perfume ingredients to be encapsulated;

c) mixing aqueous phase and oil phase in a reactor to form an emulsion comprising droplets of perfume ingredients dispersed in an aqueous external phase;

d) adjusting the pH and temperature within the reactor to initiate coacervation and shell formation around the droplets thereby to form core-shell microcapsules; and e) adjusting temperature within the reactor to initiate cross-linking and harden the shells of said core-shell capsules, before cooling to form the encapsulated perfume composition in the form of a slurry.

The resultant slurry may be further processed by adjusting the pH in a range of about 5.5 to about 7, and adding anti-microbial agents, as well as suspending agents to ensure that the microcapsules remain well dispersed within the slurry.

The slurry may have solids content in the range of about 20 to 60%, and more particularly about 30 to 50%. As used herein, the term "solids content" refers to the total weight of microcapsules expressed as a percentage of the total weight of the slurry (i.e. the combined weight of the shell material and the core contents). The total weight of encapsulated perfume may be between about 30 to 45% by weight, based on the weight of the slurry, and more particularly about 35 to 40% by weight.

The shell to core ratio of the microcapsules can be obtained by measuring the effective amount of microcapsules that have been washed and separated by filtration. The damp microcapsule cake can then be extracted using microwave solvent extraction methods, and the amount of core material measured using gas chromatographic analysis.

In accordance with the method of the present invention described herein, it is possible to prepare encapsulated perfume compositions comprising microcapsules having a core to shell weight ratio of at least 8:2, and more particularly at least 9:1. Microcapsules characterized by such a core to shell weight ratio can contain a high loading of a perfume composition, are sufficiently robust to survive manufacture and other operations related to supply chain, such as storage, transportation and incorporation into all manner of consumer products disclosed herein. Furthermore, in use they are breakable under moderate force as to release perfume in a desirable manner, as is more fully described herein.

Encapsulated perfume compositions of the present invention may be comprised of microcapsules having a volume average diameter (D 50) anywhere between 1 and 1000 μm, if desired. However, stable and performing encapsulated perfume compositions more typically comprise microcapsules that have an average diameter (D 50) between 5 μm to 50 μm, still more particularly 5 μm to 20 μm, for example 10 μm. The volume average diameter is obtained by conducting light scattering measurements using a Malvern 2000S instrument, using techniques generally known in the art.

Surprisingly, it was discovered that for a given microcapsule average diameter, more particularly for a microcapsule average diameter of 5 to 20 μm, and more particularly 5 to 8 μm, encapsulated perfume compositions formed using the positively charged colloidal stabilizer in accordance with the present invention, exhibited improved perfumery benefits when deposited on a substrate compared with encapsulated perfume compositions formed using prior art acrylic-based anionic colloidal stabilizers.

Particle size distribution is not only important for delivering the perfumery benefits described above, it is also important from an aesthetics view point. Microcapsules must be readily dispersible in slurry. Excessive creaming or sedimentation or the presence of large and visible agglomerates is not only unsightly; it can also create a negative perception in relation to performance and quality in the minds of formulators trying to incorporate the slurry into consumer product bases. In extreme cases, it may actually affect performance and quality of the slurry. In order to avoid such negative perceptions, it is desirable that not only should the microcapsules be well dispersed within a slurry; it is also highly important that the microcapsules do not agglomerate when the slurry is incorporated into consumer product bases. As stated above, this can be a problem with state of the art melamine-formaldehyde microcapsules. However, encapsulated perfume compositions formed in accordance with the present invention contain microcapsules that are resistant to the agglomeration phenomena observed with conventional microcapsules.

Encapsulated perfume compositions of the present invention may be further characterized in terms of the shell thickness of the microcapsules, which may range from 10 to 500 nm, and more particularly 50 to 150 nm. Furthermore, the shell to core mass ratio of the microcapsules may be less than 30% and still more particularly less than 20% and more particularly less than 10%.

As stated herein, the encapsulated perfume compositions of the present invention are obtained in the form of a slurry of microcapsules dispersed in an aqueous suspending medium. It is conventional to add a suspending agent to stabilize the microcapsules in the suspending medium.

Suspending agents are typically hydrocolloids that improve the physical stability of microcapsules in slurries, by preventing creaming, coagulation or sedimentation of microcapsules. Examples of hydrocolloids include polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((meth)acrylic acid), poly(maleic acid), poly(alkyl(meth)acrylate-co-(meth)acrylic acid), poly(acrylic acid-co-maleic acid) copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quartenized forms.

Having regard to the high positive zeta potential characteristic of the microcapsules, it was found that particularly physically stable and low viscosity slurries could be obtained when cationic suspending agents were employed. Particularly useful cationic suspending agents are acrylamide-based cationic thickening agents. Preferable suspending agents are cationic acrylamides including Flosoft products, and in particular Flosoft FS 222, available commercially from the company SNF Floerger, Andrézieux Cedex, FRANCE.

Slurries containing such suspending agents do not display any signs of agglomeration and have a relatively low viscosity, more particularly 500 to 5000 cps, and still more particularly about 1000 cps, measured on a Brookfield LVT viscometer at rotation speed of 60 rpm, more particularly 1000 cps at 30 to 40 wt % capsules in the slurry.

Encapsulated perfume compositions of the present invention as hereinabove defined may contain additional formulation aids such as viscosifying agents, biocides, chelating agents, and the like.

If it is desired to isolate the microcapsules in the form of a dry powder, a slurry may be spray dried in a further step. Prior to the spray drying step, it may be desirable to add a flow aid, such as silica or the like to the slurry to ensure the realization of fine, free-flowing powdered microcapsules with low surface perfume oil.

The invention provides in another of its aspects a method of stably incorporating an encapsulated perfume composition into a consumer product, the method comprising the steps of providing an encapsulated perfume composition in the form of a slurry as herein described, and mixing the slurry into the consumer product.

In a more particular embodiment in a method of stably incorporating an encapsulated perfume composition into a consumer product the slurry comprises a suspending agent as defined hereinabove.

In a more particular embodiment, the D50 of the microcapsules in the encapsulated perfume composition is 5 to 50 microns, more particularly 5 to 20 microns.

In a more particular embodiment, the D50 of the microcapsules in the encapsulated perfume composition is 5 to 50 microns, more particularly 5 to 20 microns, and the D50 of the microcapsules incorporated into the consumer product is 5 to 50 microns, more particularly 5 to 20 microns.

The encapsulated perfume compositions of the present invention may be used to encapsulate all manner of perfume ingredients. A full list of possible perfume ingredients can be found in perfumery monographs, such as "Perfume & Flavor Chemicals", S. Arctander (Allured Publishing, 1994), as well as later editions of this work, which are herein incorporated by reference.

However, the applicant has found that by employing perfume ingredient selection criteria set forth herein below, it is possible to influence both the permeability and diffusivity of perfume ingredients through the shell.

More specifically, the applicant has found that a parameter of perfume ingredient selection, which is the electron density distribution within a perfume ingredient, as reflected by the temperature-independent integral of the molecular iso-surface having electron density equal to $$0.002 e/a_0^3$$

wherein e is the dimension-less electron charge and $a_0$ is the Bohr radius of the hydrogen atom ($a_0$=5.2917720859×10$^{-11}$ m).

Employing Molecular Operating Environment chemical computational software (Version 2009, ex Chemical Computing Group, Canada, or later versions thereof, and optionally using the DDASSL RECON software plug-in (Rensselaer Polytechnic Institute, 2001-2003, or later versions thereof)), the value of this integral is given by the so-called RECON_VOLTAE quantum chemically derived descriptor. In particular, it was surprisingly found that the leakage of perfume ingredients through a microcapsule shell is considerably suppressed when the value of the molecular iso-surface integral of ingredients exceeds a certain value, more fully described herein below.

RECON VOLTAE is a parameter describing or expressing the topography of a molecule iso-surface that encloses a molecular space having an electron density is equal to 0.002 $e/a_0^3$.

In the encapsulated perfume compositions described herein below, the concentration of any encapsulated perfume ingredients (wt %) is expressed relative to the total amount of perfume ingredients encapsulated and not to the total material encapsulated. For example, although it is preferred that only perfume ingredients are encapsulated, it is contemplated that in addition to perfume ingredients, other non-perfumery ingredients or excipients may be encapsulated such as solvents or diluents, which may be beneficial in reducing the amount of perfume composition that might leak from the cores. For example, certain perfume ingredients may be provided as solutions or are diluted in suitable solvents, such as triethyl citrate "TEC". In such cases, only the amount of perfume ingredient is counted in the wt % calculation and not the solvent or diluent used to dissolve or dilute the perfume ingredient.

Such solvents or diluents are hydrophobic materials that are miscible in the perfume ingredients, and which have little or no odour in the quantities employed. Solvents commonly employed have high C log P values, for example greater than 6 and even greater than 10. Solvents include triglyceride oil, mono and diglycerides, mineral oil, silicone oil, diethyl phthalate, poly (alpha-olefins), castor oil and isopropyl myristate.

The cores of core-shell microcapsules may also contain commonly employed adjuvants. The term "adjuvants" refers to ingredients that may affect the performance of a composition, other than its hedonic performance. For example, an adjuvant may be an ingredient that acts as an aid to processing a perfume composition or consumer product containing said composition, or it may improve handling or storage of a perfume composition or consumer product. It might also be an ingredient that provides additional benefits such as imparting colour or texture. It might also be an ingredient that imparts light resistance or chemical stability to one or more ingredients contained in a perfume composition or consumer product. A detailed description of the nature and type of adjuvants commonly used in perfume compositions or consumer products cannot be exhaustive, but such ingredients are well known to a person skilled in the art. Examples of adjuvants include surfactants and emulsifiers; viscosity and rheology modifiers; thickening and gelling agents; preservative materials; pigments, dyestuffs and colouring matters; extenders, fillers and reinforcing agents; stabilizers against the detrimental effects of heat and light, bulking agents, acidulants, buffering agents and antioxidants.

A more detailed discussion of such solvents, diluents or adjuvants may be found in perfumery monographs such as the Arctander reference mentioned hereinabove.

Furthermore, in encapsulated perfume compositions it is preferred if they are comprised of at least 3 perfume ingredients, more particularly at least 5, still more particularly at least 7 and more particularly still at least 9 perfume ingredients having known RECON VOLTAE values larger than the threshold values referred to below.

It is preferred if in the practice of the present invention, perfume compositions to be encapsulated contain perfume ingredients having known RECON_VOLTAE values larger than about 1200 $Bohr^3$, more particularly larger than about 1540 $Bohr^3$, and still more particularly larger than about 1750 $Bohr^3$.

As used herein, the term "known" as it is used in relation to the RECON_VOLTAE values, or any of the other physico-chemical parameters related to the perfume ingredients described herein, means the values are known to a formulator of a perfume composition, or can be calculated in accordance with the teaching provided herein.

Preferably, more than 70 wt %, in particular more than 80 wt %, and more particularly more than 90 wt % of the perfume ingredients encapsulated have known RECON_VOLTAE values larger than about 1200 $Bohr^3$.

More particularly, more than 30 wt %, more than 35 wt %, more than 40 wt % of the perfume ingredients encapsulated have known RECON_VOLTAE values larger than about 1540 $Bohr^3$.

Encapsulated perfume compositions containing such a distribution of encapsulated perfume ingredients are particularly suitable for incorporation into aggressive (or extractive) media. These media include fabric softening or conditioning products, and particularly those containing quaternized ester surfactants (so-called "esterquats") and non-ionic surfactants. They are also usefully employed in powdered or granulated detergents, and liquid detergent compositions, and particular those formats designed as unit dosage forms contained in pouches or pods, and often referred to in the art as "liquid tabs". A fuller discussion of these ingredients and formulations is provided herein below.

They are particularly suitable for use in fabric softening or conditioning products containing unstructured surfactants. The term "unstructured surfactants" is known to persons skilled in the art. It refers to surfactant-containing compositions in which the surfactants tend to be present in the form of micelles. Micellar surfactants are particularly efficient in extracting encapsulated perfume ingredients from microcapsules.

Unstructured surfactants are to be contrasted with "structured surfactants". Structured surfactants compositions contain water, surfactant, and optionally other dissolved matter, which together form a mesophase, or a dispersion of a mesophase in a continuous aqueous medium. Surfactants and water interact to form phases that are neither liquids nor crystals; these are usually termed "liquid crystal phases," or alternatively "mesomorphic phases" or "mesophases." Because surfactants are highly organised in such compositions, they tend not to be particularly extractive towards encapsulated perfume ingredients.

Unstructured surfactants can usually be distinguished over structure surfactants upon visual inspection because the former tend to be transparent, or substantially so, whereas the latter, because of their structure, tend to appear as opaque, turbid or pearlescent.

Encapsulated perfume compositions in which more than 70 wt %, more than 80 wt %, more than 90 wt % of the perfume ingredients encapsulated have known RECON VOLTAE values larger than about 1750 $Bohr^3$ form further embodiments of the present invention.

Encapsulated perfume compositions containing such a distribution of encapsulated perfume ingredients are particularly suitable for incorporation into very aggressive media, such as those found in shampoos, hair conditioners and other personal cleansing compositions that may contain high levels of anionic, non-ionic and/or zwitterionic surfactants. A fuller discussion of these ingredients and formulations containing them is provided herein below.

By formulating perfume compositions in accordance with the known RECON VOLTAE values set out herein, it is possible to form encapsulated perfume compositions that are less prone to leakage or extraction into surrounding suspending media, and particularly those highly extractive media referred to herein.

Without wishing to be bound by theory, it is believed that the electron density distribution of a perfume ingredient, as reflected by its RECON VOLTAE value, influences the way the ingredient diffuses through the shell. In particular, the diffusion of ingredients having RECON VOLTAE values above the threshold values recited hereinabove, e.g. above about 1200, is delayed, or even suppressed, relative to perfume ingredients having RECON VOLTAE values below the given threshold value. It follows from the above that in order to provide encapsulated perfume compositions having desirable long-term stability in consumer products, particularly those that are considered aggressive or extractive media, such as those found in personal cleansing compositions and laundry detergent bases, while still delivering perfume at a desired release rate once deposited on a substrate, and particularly a dry substrate, the encapsulated perfume composition should contain a certain amount of perfume ingredients having known RECON VOLTAE values below the aforementioned 1200 $Bohr^3$ threshold. These sub-threshold perfume ingredients will diffuse more readily from core-shell microcapsules.

Being in possession of the knowledge of the RECON VOLTAE parameter, and the relationship of RECON VOLTAE to both performance and stability of encapsulated perfume compositions, the skilled person is able to create a variety of perfumes for encapsulation by balancing the relative amounts of both sub- and super-threshold perfume ingredients, designed to be both stable and performant when used in more or less extractive consumer product bases.

Thus, an encapsulated perfume composition as defined hereinabove, additionally comprising encapsulated perfume ingredients having RECON VOLTAE values below 1200 Bohr$^3$, forms another embodiment of the present invention.

In a particular embodiment an encapsulated perfume composition is characterized by a distribution of perfume ingredients having known RECON VOLTAE values, wherein 70 wt % or more, 80 wt % or more, 90 wt % or more of the perfume ingredients have known RECON VOLTAE values larger than 1200 Bohr$^3$ and 0.1 to 30 wt %, more particularly from 1 to 20 wt % and more particularly still from 1 to 10 wt % of perfume ingredients having known RECON VOLTAE values below 1200 Bohr$^3$.

In another particular embodiment an encapsulated perfume composition is characterized by a distribution of perfume ingredients having known RECON VOLTAE values, wherein: 30 wt % or more, 35 wt % or more, 40 wt % or more of perfume ingredients have known RECON VOLTAE values larger than 1540 Bohr$^3$; and 30 wt % or more, 40 wt % or more, 50 wt % or more of the perfume ingredients have known RECON VOLTAE values from 1200 Bohr$^3$ to 1540 Bohr$^3$; and from 0.1 to 30 wt %, from 1 to 20 wt %, from 1 to 10 wt % of the perfume ingredients have known RECON VOLTAE values below 1200 Bohr$^3$.

In another particular embodiment an encapsulated perfume composition is characterized by a distribution of perfume ingredients having known RECON VOLTAE values, wherein: from 0.5 to 30 wt %, from 1 to 25 wt %, from 5 to 20 wt % of the perfume ingredients have known RECON VOLTAE values above 1750 Bohr$^3$; and 20 to 60 wt %, 25 to 55 wt %, 30 to 50 wt % of the perfume ingredients having known RECON VOLTAE values from 1540 Bohr$^3$ to 1750 Bohr$^3$; and 5 to 50 wt %, more particularly 10 to 40 wt %, 15 to 30 wt % of the perfume ingredients have known RECON VOLTAE values from 1200 Bohr$^3$ to 1540 Bohr$^3$; and from 0.1 to 30 wt %, from 1 to 20 wt %, from 1 to 10 wt % of perfume ingredients have known RECON VOLTAE values below 1200 Bohr$^3$.

In yet another particular embodiment the encapsulated perfume composition is characterized by a distribution of perfume ingredients having known RECON VOLTAE values, wherein 70 wt % or more, 80 wt % or more, 90 wt % or more of perfume ingredients have known RECON VOLTAE values larger than 1750 Bohr$^3$; and from 0.1 to 30 wt %, from 1 to 20 wt %, from 1 to 10 wt % of the perfume ingredients have known RECON VOLTAE values below 1750 Bohr$^3$.

In encapsulated perfume compositions described herein, it is preferred if the weight average of known RECON VOLTAE values of the encapsulated perfume ingredients should be larger than 1540 Bohr$^3$ and more particularly larger than 1750 Bohr$^3$.

The weight average of known RECON VOLTAE values is defined here as the weighed algebraic mean of the ingredient known RECON VOLTAE values divided by the number of ingredients:

$$\langle RECON\_VOLTAE \rangle_{perfume} \equiv 1/n \sum_n (\%_i)(RECON\_VOLTAE_i)$$

wherein n is the number of ingredients i, $\%_i$ the weight percentage of ingredient i and RECON VOLTAE$_i$, the RECON VOLTAE value of ingredient i.

Particularly stable and performant encapsulated perfume compositions can be prepared, when the selection of perfume ingredients is made on the basis of both the RECON VOLTAE parameter as described hereinabove, and according to a perfume ingredient's equilibrium headspace-capsule partition coefficient "Kcaps". The equilibrium headspace-capsule partition coefficient is defined as the headspace concentration ($HS_i^c$) of a perfume ingredient i in equilibrium with a microcapsule containing an encapsulated perfume composition P comprising perfume ingredient i at a given concentration divided by the headspace concentration ($HS_i^p$) in equilibrium with free perfume P comprising same concentration of ingredient i.

$$Kcaps_i = \frac{HS_i^c}{HS_i^p}$$

The headspace concentration in equilibrium with a microcapsule can be measured using techniques well known to a person skilled in the art. In a typical procedure, a known concentration of microcapsules is transferred to a vial VC, which is closed with a septum and allowed to equilibrate at 25° C., and a known amount of free perfume is transferred to a vial VP containing a strip of blotter paper on which the perfume is deposited with a syringe. The vial is closed with a septum and allowed to equilibrate at 25° C. Headspace aliquots are then taken from both vials and the headspace concentration profiles are determined quantitatively using methods known in the art, such as headspace capillary gas chromatography, headspace gas chromatography ion mobility spectrometry, gas spectroscopy and the like.

Kcaps may be determined experimentally, or it can be calculated for an ingredient using techniques known in the art. In particular, the effect of perfume ingredients on microcapsule stability can be predicted from QSAR analysis using MOE software.

As the person skilled in the art will appreciate, QSAR methods, in the context of the present invention, assume that performance of a perfume ingredient is correlated with its chemical structure and that as a consequence activity can be modeled as a function of calculable physiochemical attributes. Such a model for performance prediction can then be used to screen the palette of known perfume ingredients, or indeed libraries of other molecules for useful candidate ingredients.

Using QSAR analysis of a representative sample of perfume ingredients in the present invention resulted in the identification of a physicochemical parameter ($\log_{10}$ Kcaps) contributing to the effect of perfume ingredients on the stability of microcapules.

$\log_{10}$Kcaps was calculated by constructing a Quantitative Structure Activity Relationship, by performing a linear regression of molecular descriptors available within computational chemistry perfume MOE (Molecular Operation Environment, version 2013.08.01, purchased from Chemical Computing Group, Corporate Headquarters, 1010 Sherbrooke St. W, Suite 910, Montreal, Canada H3A 2R7, optionally using the DDASSL RECON software plug-in (Rensselaer Polytechnic Institute, 2001-2003, or later versions thereof)). QSAR analysis was carried out using a total of 75 perfume ingredients selected for the analysis on the basis of them being a representative set of perfume ingredients that had been used in encapsulated perfume compositions. The resulting QSAR equation is given below:

Log$_{10}$Kcaps=−0.613884945931533+0.3671456789640-78 Average_EO_Neg+0.154423533060832 E_sol+1.723-05610065098 MACCS(136)+0.0650007063247245 PEO-E_VSA+3-1.6045990231291 PEOE_VSA_FPOS+12.05-72868318683 RA_2 D_pEP10-1082.58386145862 RA_n EP2-0.0382420195399682 RECON_Del(K)NA3+53.582-2 360317755 RECON_FEP9-2.50813850930136 REC- ON_ FPIP8+5.73871249195905 RECON_SIKAl0+0.04- 0005-4462330909 kS_tsC The definition of the molecular descriptors used in above equation can be found in MOE manual version 2013.08.01 (edited by Molecular Operation Environment, Chemical Computing Group, Corporate Headquarters, 1010 Sherbrooke St. W, Suite 910, Montreal, Canada H3A 2R7); or R. Todeschini and V. Consonni, Handbook of Molecular Descriptors, Wiley, 2000; and DDASSL RECON manual (Rensselaer Polytechnic Institute, 2001-2003, or later versions thereof).

Calculated Log$_{10}$ Kcaps values of some perfume ingredients are provided in the Tables below.

Perfume ingredients that are particularly useful in encapsulated perfume compositions according to the present invention may be grouped according to their respective RECON VOLTAE values and their calculated log 10 Kcaps values.

Thus, GROUP 1 perfume ingredients have RECON_VOLTAE values larger than 1200 Bohr$^3$ and calculated log$_{10}$Kcaps which are greater than −3, where the term log$_{10}$ refers to the decimal logarithm. Perfume ingredients of GROUP 1 include but are not limited to:—

| Perfumery ingredient | RECON_VOLTAE (Bohr3) | LogKcaps |
|---|---|---|
| HEDIONE (methyl 3-oxo-2-pentylcyclopentaneacetate) | 1784 | −2.4 |
| ALLYL CYCLOHEXYL PROPIONATE (allyl 3-cyclohexylpropanoate) | 1606 | −2.0 |
| AGRUMEX (2-(tert-butyl)cyclohexyl acetate) | 1678 | −1.9 |
| DIMETHYL BENZYL CARBINYL ACETATE (2-methyl-1-phenylpropan-2-yl acetate) | 1506 | −2.4 |
| IRISONE ALPHA ((E)-4-(2,6,6-trimethylcyclohex-2-en-1-yl)but-3-en-2-one) | 1676 | −1.8 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| NECTARYL (2-(2-(4-methylcyclohex-3-en-1-yl)propyl)cyclopentanone) | 1822 | −1.9 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| JASMACYCLENE ((3aR,6S,7aS)-3a,4,5,6,7,7a-hexahydro-1H-4,7-methanoinden-6-yl acetate) | 1418 | −1.7 |
| FLOROCYCLENE ((3aR,6S,7aS)-3a,4,5,6,7,7a-hexahydro-1H-4,7-methanoinden-6-yl propionate) | 1549 | −1.6 |
| HEXYL SALICYLATE (hexyl 2-hydroxybenzoate) | 1685 | −1.6 |
| DIPENTENE (1-methyl-4-(prop-1-en-2-yl)cyclohex-1-ene) | 1203 | −0.1 |
| TETRAHYDRO LINALOOL (3,7-dimethyloctan-3-ol) | 1449 | −2.2 |
| AMYL SALICYLATE (pentyl 2-hydroxybenzoate) | 1556 | −1.4 |
| ALDEHYDE C 12 MNA PURE (2-methylundecanal) | 1661 | −2.3 |
| BUTYL CYCLOHEXYL ACETATE PARA (4-(tert-butyl)cyclohexyl acetate) | 1682 | −2.7 |
| DAMASCONE DELTA ((E)-1-(2,6,6-trimethylcyclohex-3-en-1-yl)but-2-en-1-one) | 1654 | −1.3 |
| DIMETHYL BENZYL CARBINYL BUTYRATE (2-methyl-1-phenylpropan-2-yl butyrate) | 1767 | −1.6 |
| EUCALYPTOL ((1s,4s)-1,3,3-trimethyl-2-oxabicyclo[2.2.2]octane) | 1278 | −1.0 |
| FRUTONILE (2-methyldecanenitrile) | 1597 | −1.9 |
| HEXYL CINNAMIC ALDEHYDE ((E)-2-benzylideneoctanal) | 1778 | −2.5 |
| IONONE BETA ((E)-4-(2,6,6-trimethyl cyclohex-1-en-1-yl)but-3-en-2-one) | 1670 | −1.6 |
| TERPINYL ACETATE (2-(4-methylcyclohex-3-en-1-yl)propan-2-yl acetate) | 1590 | −2.0 |
| UNDECAVERTOL ((E)-4-methyldec-3-en-5-ol) | 1531 | −2.1 |
| LINALOOL (3,7-dimethylocta-1,6-dien-3-ol) | 1367 | −2.3 |
| GARDOCYCLENE ((3aR,6S,7aS)-3a,4,5,6,7,7a-hexahydro-1H-4,7-methanoinden-6-yl isobutyrate) | 1677 | −1.5 |
| IRISONE ((E)-4-(2,6,6-trimethylcyclohex-2-en-1-yl)but-3-en-2-one) | 1676 | −1.8 |
| LILIAL (3-(4-(tert-butyl)phenyl)-2-methylpropanal) | 1738 | −2.0 |
| LINALYL ACETATE (3,7-dimethylocta-1,6-dien-3-yl acetate) | 1653 | −1.5 |
| GERANIOL ((E)-3,7-dimethylocta-2,6-dien-1-ol) | 1357 | −2.0 |
| ALLYL OENANTHATE (allyl heptanoate) | 1436 | −2.5 |
| PETALIA (2-cyclohexylidene-2-(o-tolyl)acetonitrile) | 1753 | −1.4 |
| NEOBERGAMATE FORTE (2-methyl-6-methyleneoct-7-en-2-yl acetate) | 1650 | −1.4 |

-continued

| Perfumery ingredient | RECON_VOLTAE (Bohr3) | LogKcaps |
|---|---|---|
| ISONONYL ACETATE (3,5,5-trimethylhexyl acetate) | 1632 | −1.0 |
| FRESKOMENTHE (2-(sec-butyl)cyclohexanone) | 1313 | −1.6 |
| ORIVONE (4-(tert-pentyl)cyclohexanone) | 1474 | −2.1 |
| NONADYL (6,8-dimethylnonan-2-ol) | 1579 | −1.8 |
| METHYL PAMPLEMOUSSE (6,6-dimethoxy-2,5,5-trimethylhex-2-ene) | 1632 | −1.9 |
| ETHYL CAPRYLATE (ethyl octanoate) | 1462 | −1.5 |
| AMBER CORE (1-((2-(tert-butyl)cyclohexyl)oxy)butan-2-ol) | 1972 | −2.3 |
| CASHMERAN (1,1,2,3,3-pentamethyl-2,3,6,7-tetrahydro-1H-inden-4(5H)-one) | 1772 | −1.9 |
| CITRONELLOL (3,7-dimethyloct-6-en-1-ol) | 1392 | −2.4 |
| DAMASCENONE ((E)-1-(2,6,6-trimethyl cyclohexa-1,3-dien-1-yl)but-2-en-1-one) | 1608 | −1.5 |
| ETHYL SAFRANATE (ethyl 2,6,6-trimethylcyclohexa-1,3-diene-1-carboxylate) | 1579 | −2.0 |
| EUCALYPTOL ((1s,4s)-1,3,3-trimethyl-2-oxabicyclo[2.2.2]octane) | 1278 | −1.0 |
| PEONILE (2-cyclohexylidene-2-phenylacetonitrile) | 1633 | −0.9 |
| DELPHONE (2-pentylcyclopentanone) | 1313 | −1.9 |
| SILVIAL (3-(4-isobutylphenyl)-2-methylpropanal) | 1700 | −2.5 |
| TETRAHYDRO MYRCENOL (2,6-dimethyloctan-2-ol) | 1449 | −2.1 |
| CITRONELLYL PROPIONATE (3,7-dimethyloct-6-en-1-yl propionate) | 1808 | −2.0 |
| CYCLOHEXYL SALICYLATE (cyclohexyl 2-hydroxybenzoate) | 1610 | −2.2 |
| ETHYL CAPROATE (ethyl hexanoate) | 1203 | −1.4 |
| CORANOL (4-cyclohexyl-2-methylbutan-2-ol) | 1486 | −2.7 |
| BORNYL ACETATE ((2S,4S)-1,7,7-trimethylbicyclo[2.2.1]heptan-2-yl acetate) | 1631 | −1.8 |
| ALDEHYDE C 10 DECYLIC (decanal) | 1403 | −2.9 |
| ALDEHYDE C 110 UNDECYLIC (undecanal) | 1533 | −2.8 |
| ALDEHYDE MANDARINE 10%/TEC ((E)-dodec-2-enal) | 1615 | −2.7 |
| AMBERMAX (1,3,4,5,6,7-hexahydro-.beta.,1,1,5,5-pentamethyl-2H-2,4a-Methanonaphthalene-8-ethanol) | 2275 | −2.8 |
| BELAMBRE ((1R,2S,4R)-2'-isopropyl-1,7,7-trimethylspiro[bicyclo[2.2.1]heptane-2,4'-[1,3]dioxane]) | 2112 | −1.6 |
| CITRONELLYL NITRILE (3,7-dimethyloct-6-enenitrile) | 1429 | −1.6 |
| FLORHYDRAL (3-(3-isopropylphenyl)butanal) | 1568 | −2.7 |
| GERANYL ACETATE SYNTHETIC ((E)-3,7-dimethylocta-2,6-dien-1-yl acetate) | 1643 | −2.4 |
| HABANOLIDE ((E)-oxacyclohexadec-12-en-2-one) | 1978 | −2.6 |
| HEXYL ISOBUTYRATE (hexyl isobutyrate) | 1460 | −1.0 |
| MYRALDENE (4-(4-methylpent-3-en-1-yl)cyclohex-3-enecarbaldehyde) | 1613 | −2.2 |
| TRIDECENE-2-NITRILE ((E)-tridec-2-enenitrile) | 1818 | −1.5 |
| ROSACETOL (2,2,2-trichloro-1-phenylethyl acetate) | 1731 | −1.5 |
| CITRONELLYL ACETATE (3,7-dimethyloct-6-en-1-yl acetate) | 1678 | −1.7 |
| ETHYL LINALOOL ((E)-3,7-dimethylnona-1,6-dien-3-ol) | 1497 | −2.1 |
| DIPENTENE (1-methyl-4-(prop-1-en-2-yl)cyclohex-1-ene) | 1203 | −0.1 |
| GERANYL ISOBUTYRATE ((E)-3,7-dimethylocta-2,6-dien-1-yl isobutyrate) | 1901 | −1.2 |
| ISOPROPYL METHYL-2-BUTYRATE (isopropyl 2-methyl butanoate) | 1212 | −1.1 |
| RADJANOL SUPER ((E)-2-ethyl-4-(2,2,3-trimethyl cyclopent-3-en-1-yl)but-2-en-1-ol) | 1829 | −2.3 |
| TERPINOLENE (1-methyl-4-(propan-2-ylidene)cyclohex-1-ene) | 1204 | −0.1 |
| ETHYL LINALYL ACETATE ((Z)-3,7-dimethylnona-1,6-dien-3-yl acetate) | 1783 | −1.1 |
| SERENOLIDE (2-(1-(3,3-dimethylcyclohexyl)ethoxy)-2-methylpropyl cyclopropanecarboxylate) | 2429 | −2.0 |
| CITRAL ((E)-3,7-dimethylocta-2,6-dienal) | 1311 | −1.8 |
| DIMETHYL OCTENONE (4,7-dimethyloct-6-en-3-one) | 1360 | −0.8 |
| GALBANONE PURE (1-(3,3-dimethylcyclohex-1-en-1-yl)pent-4-en-1-one) | 1663 | −1.9 |
| KOAVONE ((Z)-3,4,5,6,6-pentamethylhept-3-en-2-one) | 1675 | −1.6 |
| NEROLIDYLE ((Z)-3,7,11-trimethyldodeca-1,6,10-trien-3-yl acetate) | 2257 | −2.3 |
| ADOXAL (2,6,10-trimethylundec-9-enal) | 1878 | −2.5 |
| MENTHOL NATURAL (2-isopropyl-5-methylcyclohexanol) | 1357 | −2.1 |

-continued

| Perfumery ingredient | RECON_VOLTAE (Bohr3) | LogKcaps |
|---|---|---|
| ALDEHYDE C 12 LAURIC (dodecanal) | 1662 | −2.9 |
| CITRONELLAL (3,7-dimethyloct-6-enal) | 1363 | −2.4 |
| COSMONE ((Z)-3-methylcyclotetradec-5-enone) | 1924 | −2.5 |
| CYCLAMEN ALDEHYDE (3-(4-isopropylphenyl)-2-methylpropanal) | 1567 | −1.6 |
| DIMETHYL BENZYL CARBINOL (2-methyl-1-phenylpropan-2-ol) | 1223 | −2.4 |
| FLORALOZONE (3-(4-ethylphenyl)-2,2-dimethylpropanal) | 1608 | −1.9 |
| HERBANATE ((2S)-ethyl 3-isopropylbicyclo[2.2.1]hept-5-ene-2-carboxylate) | 1629 | −0.7 |
| LEMONILE ((2E,6Z)-3,7-dimethylnona-2,6-dienenitrile) | 1515 | −1.5 |
| DIMETOL (2,6-dimethylheptan-2-ol) | 1320 | −2.0 |
| PIVAROSE (2,2-dimethyl-2-pheylethyl propanoate) | 1665 | −2.5 |
| PRECYCLEMONE B (1-methyl-4-(4-methylpent-3-en-1-yl)cyclohex-3-enecarbaldehyde) | 1783 | −2.2 |
| CITRONELLYL ACETATE (3,7-dimethyloct-6-en-1-yl acetate) | 1678 | −1.7 |
| ALDEHYDE C 11 UNDECYLENIC (undec-10-enal) | 1498 | −2.9 |
| ETHYL OENANTHATE (ethyl heptanoate) | 1333 | −1.5 |
| KARANAL (5-(sec-butyl)-2-(2,4-dimethylcyclohex-3-en-1-yl)-5-methyl-1,3-dioxane) | 2242 | −1.4 |
| NERYL ACETATE HC ((Z)-3,7-dimethylocta-2,6-dien-1-yl acetate) | 1643 | −2.4 |
| THIBETOLIDE (oxacyclohexadecan-2-one) | 2017 | −2.2 |
| FLOROPAL (2,4,6-trimethyl-4-phenyl-1,3-dioxane) | 1596 | −1.1 |
| GIVESCONE (ethyl 2-ethyl-6,6-dimethylcyclohex-2-enecarboxylate) | 1754 | −1.5 |
| TERPINENE GAMMA (1-methyl-4-propan-2-ylcyclohexa-1,4-diene) | 1205 | −0.4 |
| FIXOLIDE (1-(3,5,5,6,8,8-hexamethyl-5,6,7,8-tetrahydronaphthalen-2-yl)ethanone) | 2207 | −2.2 |
| CITRAL LEMAROME N ((E)-3,7-dimethylocta-2,6-dienal) | 1311 | −2.1 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| PARADISAMIDE (2-ethyl-N-methyl-N-(m-tolyl)butanamide) | 1790 | −3.0 |
| RASPBERRY KETONE (N112) (4-(4-hydroxyl)henyl)butan-2-one) | 1243 | −2.4 |
| ROSYRANE SUPER (4-methylene-2-phenyltetrahydro-2H-pyran) | 1353 | −1.8 |
| NEOFOLIONE ((E)-methyl non-2-enoate) | 1418 | −2.1 |
| APHERMATE (1-(3,3-dimethylcyclohexyl)ethyl formate) | 1549 | −1.9 |
| CARYOPHYLLENE ((Z)-4,11,11-trimethyl-8-methylenebicyclo[7.2.0]undec-4-ene) | 1809 | −1.0 |
| STEMONE ((E)-5-methylheptan-3-one oxime) | 1250 | −1.7 |
| EBANOL ((E)-3-methyl-5-(2,2,3-trimethylcyclopent-3-en-1-yl)pent-4-en-2-ol) | 1832 | −2.5 |
| CYCLOMYRAL (8,8-dimethyl-1,2,3,4,5,6,7,8-octahydronaphthalene-2-carbaldehyde) | 1610 | −2.4 |
| FENCHYL ACETATE ((2S)-1,3,3-trimethylbicyclo[2.2.1]heptan-2-yl acetate) | 1628 | −2.2 |
| JASMONE CIS ((Z)-3-methyl-2-(pent-2-en-1-yl)cyclopent-2-enone) | 1379 | −1.7 |
| METHYL NONYL KETONE EXTRA (undecan-2-one) | 1532 | −1.8 |
| SYLKOLIDE ((E)-2-((3,5-dimethylhex-3-en-2-yl)oxy)-2-methylpropyl cyclopropanecarboxylate) | 2177 | −1.9 |
| MELONAL (2,6-dimethylhept-5-enal) | 1229 | −2.0 |
| BUTYL BUTYRO LACTATE (1-butoxy-1-oxopropan-2-yl butyrate) | 1680 | −0.1 |
| ALDEHYDE ISO C 11 ((E)-undec-9-enal) | 1491 | −3.0 |
| DAMASCENONE GIV ((E)-1-(2,6,6-trimethylcyclohexa-1,3-dien-1-yl)but-2-en-1-one) | 1608 | −1.5 |
| ROSALVA (dec-9-en-1-ol) | 1397 | −2.6 |
| VIRIDINE ((2,2-dimethoxyethyl)benzene) | 1281 | −2.7 |
| FRUITATE ((3aS,4S,7R,7aS)-ethyl octahydro-1H-4,7-methanoindene-3a-carboxylate) | 1617 | −1.1 |
| CITRONELLYL FORMATE (3,7-dimethyloct-6-en-1-yl formate) | 1544 | −1.9 |
| EUCALYPTOL ((1s,4s)-1,3,3-trimethyl-2-oxabicyclo[2.2.2]octane) | 1278 | −1.0 |

| Perfumery ingredient | RECON_VOLTAE (Bohr3) | LogKcaps |
|---|---|---|
| IRONE ALPHA ((E)-4-(2,5,6,6-tetramethylcyclohex-2-en-1-yl)but-3-en-2-one) | 1800 | −1.5 |
| MENTHONE (2-isopropyl-5-methylcyclohexanone) | 1312 | −1.4 |
| HEXENYL-3-CIS BUTYRATE ((Z)-hex-3-en-1-yl butyrate) | 1421 | −1.2 |
| ALDEHYDE C 11 MOA (2-methyldecanal) | 1530 | −2.6 |
| CLONAL (dodecanenitrile) | 1723 | −1.0 |
| DAMASCONE ALPHA ((E)-1-(2,6,6-trimethyl cyclohex-2-en-1-yl)but-2-en-1-one) | 1657 | −1.1 |
| DECENAL-4-TRANS ((E)-dec-4-enal) | 1363 | −2.8 |
| DUPICAL ((E)-4-((3aS,7aS)-hexahydro-1H-4,7-methanoinden-5(6H)-ylidene)butanal) | 1607 | −2.5 |
| FENCHYL ALCOHOL ((1S,2R,4R)-1,3,3-trimethylbicyclo[2.2.1]heptan-2-ol) | 1345 | −2.0 |
| INDOFLOR (4,4a,5,9b-tetrahydroindeno[1,2-d][1,3]dioxine) | 1245 | −2.7 |
| MALTYL ISOBUTYRATE (2-methyl-4-oxo-4H-pyran-3-yl isobutyrate) | 1398 | −0.1 |
| METHYL OCTYNE CARBONATE (methyl non-2-ynoate) | 1376 | −1.8 |
| PELARGENE (2-methyl-4-methylene-6-phenyltetrahydro-2H-pyran) | 1480 | −1.5 |
| PYRALONE (6-(sec-butyl)quinoline) | 1466 | −1.8 |
| SUPER MUGUET ((E)-6-ethyl-3-methyloct-6-en-1-ol) | 1522 | −2.7 |
| VELOUTONE (2,2,5-trimethyl-5-pentylcyclopentanone) | 1778 | −1.9 |
| RHUBAFURANE (2,2,5-trimethyl-5-pentylcyclopentanone) | 1434 | −1.9 |
| SPIROGALBANONE (1-(spiro[4.5]dec-6-en-7-yl)pent-4-en-1-one) | 1850 | −2.0 |
| DIHYDRO ANETHOLE (propanedioic acid 1-(1-(3,3-dimethyl cyclohexyl)ethyl) 3-ethyl ester) | 1219 | −1.7 |
| ZINARINE (2-(2,4-dimethyl cyclohexyl)pyridine) | 1557 | −2.1 |
| BIGARYL (8-(sec-butyl)-5,6,7,8-tetrahydroquinoline) | 1563 | −2.0 |
| CAS SYRANE (5-tert-butyl-2-methyl-5-propyl-2H-furan) | 1624 | −1.6 |
| MANZANATE (ethyl 2-methylpentanoate) | 1202 | −1.4 |
| NONENAL-6-CIS ((Z)-non-6-enal) | 1234 | −2.5 |
| ALLYL AMYL GLYCOLATE (allyl 2-(isopentyloxy)acetate) | 1495 | −2.2 |
| DIHYDRO JASMONE (3-methyl-2-pentylcyclopent-2-enone) | 1409 | −1.7 |
| ISOCYCLOCITRAL (2,4,6-trimethylcyclohex-3-enecarbaldehyde) | 1266 | −1.8 |
| LEAF ACETAL ((Z)-1-(1-ethoxyethoxy)hex-3-ene) | 1457 | −0.7 |
| CYCLOGALBANATE (allyl 2-(cyclohexyloxy)acetate) | 1546 | −2.4 |
| LIFFAROME GIV ((Z)-hex-3-en-1-yl methyl carbonate) | 1218 | −1.5 |
| CITRATHAL R ((Z)-1,1-diethoxy-3,7-dimethylocta-2,6-diene) | 1933 | −1.1 |
| ROSYFOLIA ((1-methyl-2-(5-methylhex-4-en-2-yl)cyclopropyl)-methanol) | 1685 | −1.0 |
| (3-(4-isobutyl-2-methylphenyl)propanal) | 1700 | −2.5 |

When encapsulated in the amounts referred to hereinabove microcapsules containing perfume ingredients of GROUP 1 exhibit good resistance to leakage when suspended in mildly extractive media, such as those encountered in fabric softener or conditioning compositions, and particularly those compositions containing structured surfactants.

Those encapsulated perfume compositions described hereinabove containing perfume ingredients characterized by a RECON VOLTAE value larger than about 1200 Bohr³, wherein those ingredients are additionally characterized by having a $\log_{10}$ Kcaps greater than −3 (i.e. GROUP 1 ingredients) form additional embodiments of the present invention.

Furthermore, fabric softener or conditioning compositions, particularly those containing structured surfactants, containing said encapsulated perfume compositions form further embodiments of the present invention.

A second group of perfume ingredients, so called GROUP 2 ingredients, have RECON_VOLTAE values larger than 1540 Bohr³ and $\log_{10}$ Kcaps greater than −3. Perfume ingredients of GROUP 2 include but are not limited to:—

| Perfumery ingredient | RECON_VOLTAE (Bohr3) | LogKcaps |
|---|---|---|
| HEDIONE (methyl 3-oxo-2-pentylcyclopentaneacetate) | 1784 | −2.4 |
| ALLYL CYCLOHEXYL PROPIONATE (allyl 3-cyclohexylpropanoate) | 1606 | −2.0 |
| AGRUMEX (2-(tert-butyl)cyclohexyl acetate) | 1678 | −1.9 |

| Perfumery ingredient | RECON_VOLTAE (Bohr3) | LogKcaps |
|---|---|---|
| IRISONE ALPHA ((E)-4-(2,6,6-trimethylcyclohex-2-en-1-yl)but-3-en-2-one) | 1676 | −1.8 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| NECTARYL (2-(2-(4-methylcyclohex-3-en-1-yl)propyl)cyclopentanone) | 1822 | −1.9 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| FLOROCYCLENE ((3aR,6S,7aS)-3a,4,5,6,7,7a-hexahydro-1H-4,7-methanoinden-6-yl propionate) | 1549 | −1.6 |
| HEXYL SALICYLATE (hexyl 2-hydroxybenzoate) | 1685 | −1.6 |
| ALDEHYDE C 12 MNA PURE (2-methylundecanal) | 1661 | −2.3 |
| BUTYL CYCLOHEXYL ACETATE PARA (4-(tert-butyl)cyclohexyl acetate) | 1682 | −2.7 |
| DAMASCONE DELTA ((E)-1-(2,6,6-trimethylcyclohex-3-en-1-yl)but-2-en-1-one) | 1654 | −1.3 |
| DIMETHYL BENZYL CARBINYL BUTYRATE (2-methyl-1-phenylpropan-2-yl butyrate) | 1767 | −1.6 |
| HEXYL CINNAMIC ALDEHYDE ((E)-2-benzylideneoctanal) | 1778 | −2.5 |
| IONONE BETA ((E)-4-(2,6,6-trimethylcyclohex-1-en-1-yl)but-3-en-2-one) | 1670 | −1.6 |
| TERPINYL ACETATE (2-(4-methylcyclohex-3-en-1-yl)propan-2-yl acetate) | 1590 | −2.0 |
| GARDOCYCLENE ((3aR,6S,7aS)-3a,4,5,6,7,7a-hexahydro-1H-4,7-methanoinden-6-yl isobutyrate) | 1677 | −1.5 |
| IRISONE PURE ((E)-4-(2,6,6-trimethylcyclohex-2-en-1-yl)but-3-en-2-one) | 1676 | −1.8 |
| LILIAL (3-(4-(tert-butyl)phenyl)-2-methylpropanal) | 1738 | −2.0 |
| LINALYL ACETATE SYNTHETIC (3,7-dimethylocta-1,6-dien-3-yl acetate) | 1653 | −1.5 |
| PETALIA (2-cyclohexylidene-2-(o-tolyl)acetonitrile) | 1753 | −1.4 |
| NEOBERGAMATE FORTE (2-methyl-6-methyleneoct-7-en-2-yl acetate) | 1650 | −1.4 |
| ISONONYL ACETATE PURE (3,5,5-trimethylhexyl acetate) | 1632 | −1.0 |
| NONADYL (6,8-dimethylnonan-2-ol) | 1579 | −1.8 |
| METHYL PAMPLEMOUSSE (6,6-dimethoxy-2,5,5-trimethylhex-2-ene) | 1632 | −1.9 |
| AMBER CORE (1-((2-(tert-butyl)cyclohexyl)oxy)butan-2-ol) | 1972 | −2.3 |
| CASHMERAN (1,1,2,3,3-pentamethyl-2,3,6,7-tetrahydro-1H-inden-4(5H)-one) | 1772 | −1.9 |
| DAMASCENONE ((E)-1-(2,6,6-trimethylcyclohexa-1,3-dien-1-yl)but-2-en-1-one) | 1608 | −1.5 |
| ETHYL SAFRANATE (ethyl 2,6,6-trimethylcyclohexa-1,3-diene-1-carboxylate) | 1579 | −2.0 |
| PEONILE (2-cyclohexylidene-2-phenylacetonitrile) | 1633 | −0.9 |
| SILVIAL (3-(4-isobutylphenyl)-2-methylpropanal) | 1700 | −2.5 |
| CITRONELLYL PROPIONATE (3,7-dimethyloct-6-en-1-yl propionate) | 1808 | −2.0 |
| CYCLOHEXYL SALICYLATE (cyclohexyl 2-hydroxybenzoate) | 1610 | −2.2 |
| BORNYL ACETATE ((2S,4S)-1,7,7-trimethylbicyclo[2.2.1]heptan-2-yl acetate) | 1631 | −1.8 |
| ALDEHYDE MANDARINE ((E)-dodec-2-enal) | 1615 | −2.7 |
| AMBERMAX (1,3,4,5,6,7-hexahydro-.beta.,1,1,5,5-pentamethyl-2H-2,4a-Methanonaphthalene-8-ethanol) | 2275 | −2.8 |

-continued

| Perfumery ingredient | RECON_VOLTAE (Bohr3) | LogKcaps |
|---|---|---|
| BELAMBRE 50%/IPM ((1R,2S,4R)-2'-isopropyl-1,7,7-trimethylspiro[bicyclo[2.2.1]heptane-2,4'-[1,3]dioxane]) | 2112 | −1.6 |
| FLORHYDRAL (3-(3-isopropylphenyl)butanal) | 1568 | −2.7 |
| GERANYL ACETATE SYNTHETIC ((E)-3,7-dimethylocta-2,6-dien-1-yl acetate) | 1643 | −2.4 |
| HABANOLIDE ((E)-oxacyclohexadec-12-en-2-one) | 1978 | −2.6 |
| MYRALDENE (4-(4-methylpent-3-en-1-yl)cyclohex-3-enecarbaldehyde) | 1613 | −2.2 |
| TRIDECENE-2-NITRILE ((E)-tridec-2-enenitrile) | 1818 | −1.5 |
| ROSACETOL (2,2,2-trichloro-1-phenylethyl acetate) | 1731 | −1.5 |
| CITRONELLYL ACETATE (3,7-dimethyloct-6-en-1-yl acetate) | 1678 | −1.7 |
| GERANYL ISOBUTYRATE ((E)-3,7-dimethylocta-2,6-dien-1-yl isobutyrate) | 1901 | −1.2 |
| RADJANOL SUPER ((E)-2-ethyl-4-(2,2,3-trimethylcyclopent-3-en-1-yl)but-2-en-1-ol) | 1829 | −2.3 |
| ETHYL LINALYL ACETATE ((Z)-3,7-dimethylnona-1,6-dien-3-yl acetate) | 1783 | −1.1 |
| SERENOLIDE (2-(1-(3,3-dimethylcyclohexyl)ethoxy)-2-methylpropyl cyclopropanecarboxylate) | 2429 | −2.0 |
| GALBANONE PURE (1-(3,3-dimethylcyclohex-1-en-1-yl)pent-4-en-1-one) | 1663 | −1.9 |
| KOAVONE ((Z)-3,4,5,6,6-pentamethylhept-3-en-2-one) | 1675 | −1.6 |
| NEROLIDYLE ((Z)-3,7,11-trimethyldodeca-1,6,10-trien-3-yl acetate) | 2257 | −2.3 |
| ADOXAL (2,6,10-trimethylundec-9-enal) | 1878 | −2.5 |
| ALDEHYDE C 12 LAURIC (dodecanal) | 1662 | −2.9 |
| COSMONE ((Z)-3-methylcyclotetradec-5-enone) | 1924 | −2.5 |
| CYCLAMEN ALDEHYDE (3-(4-isopropylphenyl)-2-methylpropanal) | 1567 | −1.6 |
| FLORALOZONE (3-(4-ethylphenyl)-2,2-dimethylpropanal) | 1608 | −1.9 |
| HERBANATE ((2S)-ethyl 3-isopropylbicyclo[2.2.1]hept-5-ene-2-carboxylate) | 1629 | −0.7 |
| PIVAROSE (2,2-dimethyl-2-pheylethyl propanoate) | 1665 | −2.5 |
| PRECYCLEMONE B (1-methyl-4-(4-methylpent-3-en-1-yl)cyclohex-3-enecarbaldehyde) | 1783 | −2.2 |
| CITRONELLYL ACETATE (3,7-dimethyloct-6-en-1-yl acetate) | 1678 | −1.7 |
| KARANAL (5-(sec-butyl)-2-(2,4-dimethylcyclohex-3-en-1-yl)-5-methyl-1,3-dioxane) | 2242 | −1.4 |
| NERYL ACETATE HC ((Z)-3,7-dimethylocta-2,6-dien-1-yl acetate) | 1643 | −2.4 |
| THIBETOLIDE (oxacyclohexadecan-2-one) | 2017 | −2.2 |
| FLOROPAL (2,4,6-trimethyl-4-phenyl-1,3-dioxane) | 1596 | −1.1 |
| GIVESCONE (ethyl 2-ethyl-6,6-dimethylcyclohex-2-enecarboxylate) | 1754 | −1.5 |
| FIXOLIDE (1-(3,5,5,6,8,8-hexamethyl-5,6,7,8-tetrahydronaphthalen-2-yl)ethanone) | 2207 | −2.2 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| PARADISAMIDE (2-ethyl-N-methyl-N-(m-tolyl)butanamide) | 1790 | −3.0 |
| CARYOPHYLLENE ((Z)-4,11,11-trimethyl-8-methylenebicyclo[7.2.0]undec-4-ene) | 1809 | −1.0 |
| EBANOL ((E)-3-methyl-5-(2,2,3-trimethylcyclopent-3-en-1-yl)pent-4-en-2-ol) | 1832 | −2.5 |
| CYCLOMYRAL (8,8-dimethyl-1,2,3,4,5,6,7,8-octahydronaphthalene-2-carbaldehyde) | 1610 | −2.4 |

-continued

| Perfumery ingredient | RECON_VOLTAE (Bohr3) | LogKcaps |
|---|---|---|
| FENCHYL ACETATE ((2S)-1,3,3-trimethylbicyclo[2.2.1]heptan-2-yl acetate) | 1628 | −2.2 |
| SYLKOLIDE ((E)-2-((3,5-dimethylhex-3-en-2-yl)oxy)-2-methylpropyl cyclopropanecarboxylate) | 2177 | −1.9 |
| BUTYL BUTYRO LACTATE (1-butoxy-1-oxopropan-2-yl butyrate) | 1680 | −0.1 |
| DAMASCENONE GIV ((E)-1-(2,6,6-trimethylcyclohexa-1,3-dien-1-yl)but-2-en-1-one) | 1608 | −1.5 |
| FRUITATE ((3aS,4S,7R,7aS)-ethyl octahydro-1H-4,7-methanoindene-3a-carboxylate) | 1617 | −1.1 |
| IRONE ALPHA ((E)-4-(2,5,6,6-tetramethylcyclohex-2-en-1-yl)but-3-en-2-one) | 1800 | −1.5 |
| CLONAL (dodecanenitrile) | 1723 | −1.0 |
| DAMASCONE ALPHA ((E)-1-(2,6,6-trimethylcyclohex-2-en-1-yl)but-2-en-1-one) | 1657 | −1.1 |
| DUPICAL ((E)-4-((3aS,7aS)-hexahydro-1H-4,7-methanoinden-5(6H)-ylidene)butanal) | 1607 | −2.5 |
| VELOUTONE (2,2,5-trimethyl-5-pentylcyclopentanone) | 1778 | −1.9 |
| SPIROGALBANONE (1-(spiro[4.5]dec-6-en-7-yl)pent-4-en-1-one) | 1850 | −2.0 |
| ZINARINE (2-(2,4-dimethylcyclohexyl)pyridine) | 1557 | −2.1 |
| BIGARYL (8-(sec-butyl)-5,6,7,8-tetrahydroquinoline) | 1563 | −2.0 |
| CASSYRANE (5-tert-butyl-2-methyl-5-propyl-2H-furan) | 1624 | −1.6 |
| CITRATHAL R ((Z)-1,1-diethoxy-3,7-dimethylocta-2,6-diene) | 1933 | −1.1 |
| ROSYFOLIA ((1-methyl-2-(5-methylhex-4-en-2-yl)cyclopropyl)-methanol) | 1685 | −1.0 |
| (3-(4-isobutyl-2-methylphenyl)propanal) | 1700 | −2.5 |

When employed in encapsulated perfume compositions in the amounts referred to hereinabove in accordance with the present invention, microcapsules containing GROUP 2 ingredients exhibit good resistance to leakage when suspended in harshly extractive media, such as solid and liquid laundry care detergents, and particularly those formats that are designed as unit dosage forms contained in pouches or pods, and often referred to in the art as "liquid tabs", further discussion of which is provided herein below.

Those encapsulated perfume compositions described hereinabove containing perfume ingredients characterized by a RECON VOLTAE value larger than about 1540 Bohr$^3$, wherein those ingredients are additionally characterized by having a $\log_{10}$ Kcaps greater than −3 (i.e. GROUP 2 ingredients) form additional embodiments of the present invention.

A GROUP 3 of perfume ingredients is characterized by ingredients having RECON VOLTAE values larger than 1750 Bohr$^3$ and $\log_{10}$ Kcaps greater than −3. Perfume ingredients of GROUP 3 include but are not limited to:—

| Perfumery ingredient | RECON_VOLTAE (Bohr3) | LogKcaps |
|---|---|---|
| ADOXAL (2,6,10-trimethylundec-9-enal) | 1878 | −2.5 |
| AMBER CORE (1-((2-(tert-butyl)cyclohexyl)oxy)butan-2-ol) | 1972 | −2.3 |
| AMBERMAX (1,3,4,5,6,7-hexahydro-.beta.,1,1,5,5-pentamethyl-2H-2,4a-Methanonaphthalene-8-ethanol) | 2275 | −2.8 |
| AMBROCENIDE ((4aR,5R,7aS,9R)-Octahydro-2,2,5,8,8,9a-hexamethyl-4H-4a,9-methanoazuleno[5,6-d]-1,3-dioxole) | 2339 | −2.1 |
| BELAMBRE ((1R,2S,4R)-2'-isopropyl-1,7,7-trimethylspiro[bicyclo[2.2.1]heptane-2,4'-[1,3]dioxane]) | 2112 | −1.6 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| CARYOPHYLLENE ((Z)-4,11,11-trimethyl-8-methylenebicyclo[7.2.0]undec-4-ene) | 1809 | −1.0 |

-continued

| Perfumery ingredient | RECON_VOLTAE (Bohr3) | LogKcaps |
|---|---|---|
| CASHMERAN (1,1,2,3,3-pentamethyl-2,3,6,7-tetrahydro-1H-inden-4(5H)-one) | 1772 | −1.9 |
| CITRONELLYL PROPIONATE (3,7-dimethyloct-6-en-1-yl propionate) | 1808 | −2.0 |
| COSMONE ((Z)-3-methylcyclotetradec-5-enone) | 1924 | −2.5 |
| DIMETHYL BENZYL CARBINYL BUTYRATE (2-methyl-1-phenylpropan-2-yl butyrate) | 1767 | −1.6 |
| EBANOL ((E)-3-methyl-5-(2,2,3-trimethylcyclopent-3-en-1-yl)pent-4-en-2-ol) | 1832 | −2.5 |
| ETHYL LINALYL ACETATE ((Z)-3,7-dimethylnona-1,6-dien-3-yl acetate) | 1783 | −1.1 |
| FIXOLIDE (1-(3,5,5,6,8,8-hexamethyl-5,6,7,8-tetrahydronaphthalen-2-yl)ethanone) | 2207 | −2.2 |
| GERANYL ISOBUTYRATE ((E)-3,7-dimethylocta-2,6-dien-1-yl isobutyrate) | 1901 | −1.2 |
| GIVESCONE (ethyl 2-ethyl-6,6-dimethylcyclohex-2-enecarboxylate) | 1754 | −1.5 |
| HABANOLIDE ((E)-oxacyclohexadec-12-en-2-one) | 1978 | −2.6 |
| HEDIONE (methyl 3-oxo-2-pentylcyclopentaneacetate) | 1784 | −2.4 |
| HEXYL CINNAMIC ALDEHYDE ((E)-2-benzylideneoctanal) | 1778 | −2.5 |
| IRONE ALPHA ((E)-4-(2,5,6,6-tetramethylcyclohex-2-en-1-yl)but-3-en-2-one) | 1800 | −1.5 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| KARANAL (5-(sec-butyl)-2-(2,4-dimethylcyclohex-3-en-1-yl)-5-methyl-1,3-dioxane) | 2242 | −1.4 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| NECTARYL (2-(2-(4-methylcyclohex-3-en-1-yl)propyl)cyclopentanone) | 1822 | −1.9 |
| NEROLIDYLE ((Z)-3,7,11-trimethyldodeca-1,6,10-trien-3-yl acetate) | 2257 | −2.3 |
| PARADISAMIDE (2-ethyl-N-methyl-N-(m-tolyl)butanamide) | 1790 | −3.0 |
| PETALIA (2-cyclohexylidene-2-(o-tolyl)acetonitrile) | 1753 | −1.4 |
| PRECYCLEMONE B (1-methyl-4-(4-methylpent-3-en-1-yl)cyclohex-3-enecarbaldehyde) | 1783 | −2.2 |
| RADJANOL SUPER ((E)-2-ethyl-4-(2,2,3-trimethylcyclopent-3-en-1-yl)but-2-en-1-ol) | 1829 | −2.3 |
| SERENOLIDE (2-(1-(3,3-dimethylcyclohexyl)ethoxy)-2-methylpropyl cyclopropanecarboxylate) | 2429 | −2.0 |
| SYLKOLIDE ((E)-2-((3,5-dimethylhex-3-en-2-yl)oxy)-2-methylpropyl cyclopropanecarboxylate) | 2177 | −1.9 |
| THIBETOLIDE (oxacyclohexadecan-2-one) | 2017 | −2.2 |
| TRIDECENE-2-NITRILE ((E)-tridec-2-enenitrile) | 1818 | −2.2 |
| VELOUTONE (2,2,5-trimethyl-5-pentylcyclopentanone) | 1778 | −1.9 |
| SPIROGALBANONE (1-(spiro[4.5]dec-6-en-7-yl)pent-4-en-1-one) | 1850 | −2.0 |
| CITRATHAL R ((Z)-1,1-diethoxy-3,7-dimethylocta-2,6-diene) | 1933 | −1.1 |

When said ingredients are employed in encapsulated perfume compositions in the amounts referred to hereinabove in accordance with the present invention, microcapsules containing the perfume ingredients of GROUP 3 exhibit good resistance to leakage when suspended in harshly extractive media, such as encountered in shampoos, hair conditioners and other personal cleansing compositions.

Those encapsulated perfume compositions described hereinabove containing perfume ingredients characterized by a RECON VOLTAE value larger than about 1200 Bohr$^3$, wherein those ingredients are additionally characterized by having a login K caps greater than −3 (i.e. GROUP 3 ingredients) form additional embodiments of the present invention.

Furthermore, personal cleansing compositions, including shampoos, containing said encapsulated perfume compositions form still further embodiments of the present invention.

A particular challenge that faces formulators of encapsulated perfume compositions is to strike an acceptable balance between microcapsule stability (i.e. the resistance to leakage of perfume ingredients from the cores of microcapsules) and performance, that is, the ability of a microcapsule to release perfume over time at a desired rate. Typically, if microcapsules are very stable during storage in extractive bases, then they tend not to release their core contents other than in response to quite high mechanical forces. When such microcapsules are deposited on substrates, such as fabric, hair or skin, a perfume impression may only be noticeable with vigorous rubbing of the treated substrate. Such microcapsules are said to possess "post-rub" performance, but the pre-rub odour impression is weak or non-existent.

The provision encapsulated perfume compositions comprising stable microcapsules, and particularly microcapsules that are stable in aggressive or extractive media that also exhibit acceptable pre-rub odour impression is challenging.

The present invention articulates another physicochemical parameter that correlates well with pre-rub odour impression of perfume ingredients encapsulated in core shell microcapsules.

The intrinsic Pre-Rub Odour Contribution ("PROC") of a perfume ingredient is given by the concentration (wt %) of a perfume ingredient to be encapsulated, multiplied by its standard Odour Value ($OV_i$), and by its equilibrium headspace-capsule partition coefficient "Kcaps". Hence for each perfume ingredient i, a Pre-Rub Odour Contribution is defined by $$PROC_i = OV_i[\log_{10} Kcaps_i + 3]$$

Furthermore, the partial Pre-Rub Odour Contribution (pPROC) of an ingredient is defined as its concentration (wt %) in the perfume multiplied by its standard Odour Value ($OV_i$) and by its equilibrium headspace-capsule partition coefficient Kcaps. Hence for each perfume ingredient i, a partial Pre-Rub Odour Contribution is defined by $$pPROC_i = c_i OV_i[\log_{10} Kcaps_i + 3]$$

Finally, the total Pre-Rub Odour Contribution (tPROC) is the sum of the partial Pre-Rub Odour Contribution (pPROC) over all ingredients in an encapsulated perfume composition.

The standard Odour Value ($OV_i$) is defined as the ratio of the standard equilibrium headspace concentration of the ingredient to the Odour Detection Threshold of this ingredient.

The term "standard equilibrium headspace concentration" used hereinabove refers to the concentration of a perfume ingredient in equilibrium with its condensed form (that is, its solid or liquid form) at a temperature of 25° C. and under a pressure of 1 atmosphere. It can be measured by using any of the quantitative headspace analysis techniques known in the art, see for example Mueller and Lamparsky in Perfumes: Art, Science and Technology, Chapter 6 "The Measurement of Odors" at pages 176-179 (Elsevier 1991).

The term Odour Detection Threshold ($ODT_i$) used herein above refers to the average concentration above which a perfume ingredient i can be perceived by a panellist and can be measured by olfactometry, as described, for example in Mueller and Lamparsky (op. cit).

The equilibrium headspace concentration may be measured as follows: 500 mg of the test compound is added to a headspace container which is then sealed. The container is then incubated at constant 25'C until the compound reached equilibrium between the gas and the liquid phase. A defined volume of this saturated headspace (usually 0.5-1 lt) is trapped on a micro filter using Porapak Q as sorbent. After filter extraction with an appropriate solvent (usually 30-100 ul methyl tert. butyl ether), an aliquot of the extract is analyzed by gas chromatography (GC). Quantification is performed by the external standard calibration method. The concentration in the original headspace can be calculated (in terms of µg/l) from the headspace volume sucked through the micro filter and the aliquot of the filter extract injected into the gas chromatograph. The final headspace concentration value of a given test compound is obtained as the mean value of three independent measurements. Further information of the technique hereinabove described may be found in the article of Etzweiler, F.; Senn E. and Neuner-Jehle N., Ber. Bunsen-Ges. Phys. Chem. 1984, 88, 578-583, which is hereby incorporated by reference.

The Odour Detection Threshold ($ODT_i$) may be measured by using an olfactometer. The following steps can be carried out and the odour thresholds for each compounds listed in Table hereinbelow.

The olfactometer functions on the principle of a linear dilution of an odorant in a carrier gas. The quantity of odorant displaced depends on its vapour pressure and the carrier gas flow. A constant flow of nitrogen, regulated by a flow regulator, carries the odorant from a sample container to a mixing chamber. There, the carrier gas-odour mixture is diluted with odourless air. From the mixing chamber one part of the diluted odorous air is allowed to flow via a fused silica capillary to the sniffing funnel. The flow rate through the capillary, which determines the dosage of odorous air from the mixing chamber into the sniffing funnel, depends on the opening the valve which can be regulated via PC from 1 to 256 ml in binary steps. The final dilution of the odorous air sample occurs in the glass funnel by flushing them permanently with odourless air at a flow rate of 8 lt/min. Forced-choice triangle presentation is achieved by a special automated channel setting device where only one position of a switch the odorant delivering capillary enters in the sniffing funnel, whereas in two other positions the capillary is positioned outside the funnel and where the effluent is sucked away. After each trial the channel setting is changed automatically and in a random order. The concentration is calculated from the odorants vapour pressure and from the dilution ratios that were applied in the olfactometer, assuming that vapour pressure saturation is achieved in the sample generator. As a control the concentration is determined analytically by sampling a known volume from the capillary effluent into a headspace filter and by subsequent gas chromatographic quantitation of the odourant in the desorption solution.

Each panellist (panel of 15 persons) starts sniffing at the olfactometer at a concentration level at which it perceives the odorant at medium intensity. After three correct answers in three consecutive trials (or four correct answers of five trials) at the same level, stimulus concentration is decreased by a factor of two to the next lower level, and so on, until the panellist has reached its threshold level. The final threshold value of a given odorant is obtained as the mean value of all individual threshold levels.

Encapsulated perfume compositions of the present invention displaying good pre-rub performance may be prepared by selecting perfume ingredients on the basis of their PROC values, such that the total Pre-Rub Odour Contribution of the perfume ingredients encapsulated in the composition is be between about $0.5\times10^6$ and $1.0\times10^7$, more particularly between $1\times10^6$ and $8\times10^6$ and more particularly still between $1.5\times10^6$ and $6\times10^6$.

Still further, in order to obtain encapsulated perfume compositions having optimal performance in terms of stability with respect to leakage, particularly in highly extractive/aggressive media and performance, in particular pre-rub performance, the perfume ingredients may be selected on the basis of their PROC values, such that the total Pre-Rub Odour Contribution of the perfume ingredients encapsulated in the composition should be between about $0.5\times10^6$ and $1\times10^7$, more particularly between $1\times10^6$ and $8\times10^6$ and more particularly still between $1.5\times10^6$ and $6\times10^6$, and the distribution of perfume ingredient RECON_VOLTAE and $\log_{10}$ Kcaps values are within the ranges as disclosed hereinabove.

A GROUP 4 of perfume ingredients, and their respective PROC values is listed in the Table below. It is preferred that encapsulated perfume compositions having high total PROC values are composed of the GROUP 4 ingredients specified herein below, although having regard to the teaching of the present invention, the skilled person may easily calculate the PROC values of other perfume ingredients not listed, and use them in encapsulated perfume compositions of the present invention.

GROUP 4 perfumery ingredients include but are not limited to:—

| Perfumery ingredient | PROC |
|---|---|
| MANZANATE (ethyl 2-methylpentanoate) | 99577526 |
| DAMASCONE DELTA ((E)-1-(2,6,6-trimethylcyclohex-3-en-1-yl)but-2-en-1-one) | 65924274 |
| DAMASCENONE ((E)-1-(2,6,6-trimethylcyclohexa-1,3-dien-1-yl)but-2-en-1-one) | 33149935 |
| EUCALYPTOL ((1s,4s)-1,3,3-trimethyl-2-oxabicyclo[2.2.2]octane) | 20085069 |
| ETHYL CAPROATE (ethyl hexanoate) | 16063000 |
| NONENAL-6-CIS ((Z)-non-6-enal) | 14610000 |
| ALDEHYDE C 12 MNA (2-methylundecanal) | 6849504 |
| GALBANONE PURE (1-(3,3-dimethylcyclohex-1-en-1-yl)pent-4-en-1-one) | 4793532 |
| BIGARYL (8-(sec-butyl)-5,6,7,8-tetrahydroquinoline) | 4223123 |
| MELONAL (2,6-dimethylhept-5-enal) | 3633579 |
| DAMASCONE ALPHA ((E)-1-(2,6,6-trimethylcyclohex-2-en-1-yl)but-2-en-1-one) | 1869529 |
| ROSYRANE SUPER (4-methylene-2-phenyltetrahydro-2H-pyran) | 1841920 |
| PELARGENE (2-methyl-4-methylene-6-phenyltetrahydro-2H-pyran) | 1768363 |
| SPIROGALBANONE (1-(spiro[4.5]dec-6-en-7-yl)pent-4-en-1-one) | 1489842 |
| ETHYL SAFRANATE (ethyl 2,6,6-trimethylcyclohexa-1,3-diene-1-carboxylate) | 1446690 |
| DECENAL-4-TRANS ((E)-dec-4-enal) | 1068978 |
| CASSYRANE (5-tert-butyl-2-methyl-5-propyl-2H-furan) | 911423 |
| DELPHONE (2-pentylcyclopentanone) | 771798 |
| TERPINOLENE (1-methyl-4-(propan-2-ylidene)cyclohex-1-ene) | 672048 |
| IONONE BETA ((E)-4-(2,6,6-trimethylcyclohex-1-en-1-yl)but-3-en-2-one) | 668147 |
| ETHYL OENANTHATE (ethyl heptanoate) | 467433 |
| ALLYL AMYL GLYCOLATE (allyl 2-(isopentyloxy)acetate) | 448677 |
| LINALOOL (3,7-dimethylocta-1,6-dien-3-ol) | 405669 |
| ISOCYCLOCITRAL (2,4,6-trimethylcyclohex-3-enecarbaldehyde) | 362665 |
| ISOPROPYL METHYL-2-BUTYRATE (isopropyl 2-methyl butanoate) | 320608 |
| FLORHYDRAL (3-(3-isopropylphenyl)butanal) | 294597 |
| DIMETOL (2,6-dimethylheptan-2-ol) | 294170 |
| ROSYFOLIA (3-(4-isobutyl-2-methylphenyl)propanal) | 279858 |
| 3-(4-isobutyl-2-methylphenyl)propanal (3-(4-isobutyl-2-methylphenyl)propanal) | 279536 |
| METHYL OCTYNE CARBONATE (methyl non-2-ynoate) | 270258 |
| JASMACYCLENE ((3aR,6S,7aS)-3a,4,5,6,7,7a-hexahydro-1H-4,7-methanoinden-6-yl acetate) | 259747 |
| CYCLOGALBANATE (allyl 2-(cyclohexyloxy)acetate) | 220660 |
| FLOROPAL (2,4,6-trimethyl-4-phenyl-1,3-dioxane) | 215929 |
| DIPENTENE (1-methyl-4-(prop-1-en-2-yl)cyclohex-1-ene) | 189713 |
| FRUITATE ((3aS,4S,7R,7aS)-ethyl octahydro-1H-4,7-methanoindene-3a-carboxylate) | 176891 |
| METHYL PAMPLEMOUSSE (6,6-dimethoxy-2,5,5-trimethylhex-2-ene) | 151438 |
| IRISONE PURE ((E)-4-(2,6,6-trimethylcyclohex-2-en-1-yl)but-3-en-2-one) | 143717 |
| IRISONE ALPHA ((E)-4-(2,6,6-trimethylcyclohex-2-en-1-yl)but-3-en-2-one) | 143714 |
| LIFFAROME ((Z)-hex-3-en-1-yl methyl carbonate) | 141869 |
| CASHMERAN (1,1,2,3,3-pentamethyl-2,3,6,7-tetrahydro-1H-inden-4(5H)-one) | 141286 |
| TETRAHYDRO LINALOOL (3,7-dimethyloctan-3-ol) | 140812 |
| CITRONELLAL (3,7-dimethyloct-6-enal) | 126286 |
| ETHYL LINALOOL ((E)-3,7-dimethylnona-1,6-dien-3-ol) | 122602 |
| LEMONILE ((2E,6Z)-3,7-dimethylnona-2,6-dienenitrile) | 112447 |
| RHUBAFURAN (2,4-dimethyl-4-phenyltetrahydrofuran) | 109862 |
| FLOROCYCLENE ((3aR,6S,7aS)-3a,4,5,6,7,7a-hexahydro-1H-4,7-methanoinden-6-yl propionate) | 109419 |
| EBANOL ((E)-3-methyl-5-(2,2,3-trimethylcyclopent-3-en-1-yl)pent-4-en-2-ol) | 106853 |
| HEXENYL-3-CIS BUTYRATE ((Z)-hex-3-en-1-yl butyrate) | 97634 |
| ISORALDEINE 70 ((E)-3-methyl-4-(2,6,6-trimethylcyclohex-2-en-1-yl)but-3-en-2-one) | 83954 |

-continued

| Perfumery ingredient | PROC |
|---|---|
| MENTHONE (2-isopropyl-5-methylcyclohexanone) | 83516 |
| ETHYL CAPRYLATE (ethyl octanoate) | 81140 |
| GIVESCONE (ethyl 2-ethyl-6,6-dimethylcyclohex-2-enecarboxylate) | 76022 |
| CITRONELLYL NITRILE (3,7-dimethyloct-6-enenitrile) | 71124 |
| JASMONE CIS ((Z)-3-methyl-2-(pent-2-en-1-yl)cyclopent-2-enone) | 66032 |
| FENCHYL ALCOHOL ((1S,2R,4R)-1,3,3-trimethylbicyclo[2.2.1]heptan-2-ol) | 65384 |
| RADJANOL SUPER ((E)-2-ethyl-4-(2,2,3-trimethylcyclopent-3-en-1-yl)but-2-en-1-ol) | 64782 |
| UNDECAVERTOL ((E)-4-methyldec-3-en-5-ol) | 61799 |
| DUPICAL ((E)-4-((3aS,7aS)-hexahydro-1H-4,7-methanoinden-5(6H)-ylidene)butanal) | 60602 |
| BOISAMBRENE FORTE ((ethoxymethoxy)cyclododecane) | 59050 |
| ALDEHYDE C 11 MOA (2-methyldecanal) | 58883 |
| ISO E SUPER (1-(2,3,8,8-tetramethyl-1,2,3,4,5,6,7,8-octahydronaphthalen-2-yl)ethanone) | 52929 |
| DIMETHYL OCTENONE (4,7-dimethyloct-6-en-3-one) | 51879 |
| TERPINENE GAMMA (1-methyl-4-propan-2-ylcyclohexa-1,4-diene) | 51728 |
| FRESKOMENTHE (2-(sec-butyl)cyclohexanone) | 49849 |
| HEDIONE (methyl 3-oxo-2-pentylcyclopentaneacetate) | 47438 |
| CLONAL (dodecanenitrile) | 46090 |
| GARDOCYCLENE ((3aR,6S,7aS)-3a,4,5,6,7,7a-hexahydro-1H-4,7-methanoinden-6-yl isobutyrate) | 42816 |
| HERBANATE ((2S)-ethyl 3-isopropylbicyclo[2.2.1]hept-5-ene-2-carboxylate) | 38513 |
| LILIAL (3-(4-(tert-butyl)phenyl)-2-methylpropanal) | 32603 |
| SYLKOLIDE ((E)-2-((3,5-dimethylhex-3-en-2-yl)oxy)-2-methylpropyl cyclopropanecarboxylate) | 32277 |
| GERANIOL ((E)-3,7-dimethylocta-2,6-dien-1-ol) | 32071 |
| KOAVONE ((Z)-3,4,5,6,6-pentamethylhept-3-en-2-one) | 31805 |
| ROSACETOL (2,2,2-trichloro-1-phenylethyl acetate) | 31559 |
| CYCLAMEN ALDEHYDE (3-(4-isopropylphenyl)-2-methylpropanal) | 31268 |
| ALLYL CYCLOHEXYL PROPIONATE (allyl 3-cyclohexylpropanoate) | 29587 |
| BELAMBRE 50%/IPM ((1R,2S,4R)-2'-isopropyl-1,7,7-trimethylspiro[bicyclo[2.2.1]heptane-2,4'-[1,3]dioxane]) | 27187 |
| NONADYL (6,8-dimethylnonan-2-ol) | 26158 |
| FRUTONILE (2-methyldecanenitrile) | 24822 |
| TRIDECENE-2-NITRILE ((E)-tridec-2-enenitrile) | 24181 |
| PYRALONE (6-(sec-butyl)quinoline) | 23864 |
| STEMONE ((E)-5-methylheptan-3-one oxime) | 22947 |
| CITRAL LEMAROME N ((E)-3,7-dimethylocta-2,6-dienal) | 20039 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 19783 |
| ALDEHYDE C 110 UNDECYLIC (undecanal) | 18200 |
| SILVIAL (3-(4-isobutylphenyl)-2-methylpropanal) | 16666 |
| ALDEHYDE C 11 UNDECYLENIC (undec-10-enal) | 15988 |
| CITRONELLOL (3,7-dimethyloct-6-en-1-ol) | 15832 |
| ROSALVA (dec-9-en-1-ol) | 14982 |
| VELOUTONE (2,2,5-trimethyl-5-pentylcyclopentanone) | 14571 |
| MYRALDENE (4-(4-methylpent-3-en-1-yl)cyclohex-3-enecarbaldehyde) | 13927 |
| AMYL SALICYLATE (pentyl 2-hydroxybenzoate) | 13880 |
| TETRAHYDRO MYRCENOL (2,6-dimethyloctan-2-ol) | 13764 |
| BOISIRIS ((1S,2R,5R)-2-ethoxy-2,6,6-trimethyl-9-methylenebicyclo[3.3.1]nonane) | 13558 |
| NECTARYL (2-(2-(4-methylcyclohex-3-en-1-yl)propyl)cyclopentanone) | 13091 |
| METHYL NONYL KETONE EXTRA (undecan-2-one) | 11831 |
| PETALIA (2-cyclohexylidene-2-(o-tolyl)acetonitrile) | 10949 |
| FLORALOZONE (3-(4-ethylphenyl)-2,2-dimethylpropanal) | 10053 |
| PEONILE (2-cyclohexylidene-2-phenylacetonitrile) | 9995 |
| AGRUMEX (2-(tert-butyl)cyclohexyl acetate) | 9864 |
| IRONE ALPHA ((E)-4-(2,5,6,6-tetramethylcyclohex-2-en-1-yl)but-3-en-2-one) | 9686 |
| ORIVONE (4-(tert-pentyl)cyclohexanone) | 9146 |
| NEOBERGAMATE FORTE (2-methyl-6-methyleneoct-7-en-2-yl acetate) | 8351 |
| ISONONYL ACETATE (3,5,5-trimethylhexyl acetate) | 7732 |
| ALLYL OENANTHATE (allyl heptanoate) | 7580 |
| DIMETHYL BENZYL CARBINYL ACETATE (2-methyl-1-phenylpropan-2-yl acetate) | 7061 |
| COSMONE ((Z)-3-methylcyclotetradec-5-enone) | 6460 |
| SERENOLIDE (2-(1-(3,3-dimethylcyclohexyl)ethoxy)-2-methylpropyl cyclopropanecarboxylate) | 5947 |
| RASPBERRY KETONE (N112) (4-(4-hydroxyphenyl)butan-2-one) | 5860 |
| ETHYL LINALYL ACETATE ((Z)-3,7-dimethylnona-1,6-dien-3-yl acetate) | 5526 |
| DIMETHYL BENZYL CARBINYL BUTYRATE (2-methyl-1-phenylpropan-2-yl butyrate) | 5269 |
| MALTYL ISOBUTYRATE (2-methyl-4-oxo-4H-pyran-3-yl isobutyrate) | 5209 |
| HEXYL SALICYLATE (hexyl 2-hydroxybenzoate) | 4862 |

-continued

| Perfumery ingredient | PROC |
|---|---|
| AMBER CORE (1-((2-(tert-butyl)cyclohexyl)oxy)butan-2-ol) | 4356 |
| PRECYCLEMONE B (1-methyl-4-(4-methylpent-3-en-1-yl)cyclohex-3-enecarbaldehyde) | 4350 |
| HEXYL ISOBUTYRATE (hexyl isobutyrate) | 4190 |
| ADOXAL (2,6,10-trimethylundec-9-enal) | 3827 |
| THIBETOLIDE (oxacyclohexadecan-2-one) | 3525 |
| NEOFOLIONE ((E)-methyl non-2-enoate) | 3459 |
| TERPINYL ACETATE (2-(4-methylcyclohex-3-en-1-yl)propan-2-yl acetate) | 3429 |
| FENCHYL ACETATE ((2S)-1,3,3-trimethylbicyclo[2.2.1]heptan-2-yl acetate) | 3166 |
| SUPER MUGUET ((E)-6-ethyl-3-methyloct-6-en-1-ol) | 2813 |
| KARANAL (5-(sec-butyl)-2-(2,4-dimethylcyclohex-3-en-1-yl)-5-methyl-1,3-dioxane) | 2751 |
| CITRONELLYL PROPIONATE (3,7-dimethyloct-6-en-1-yl propionate) | 2710 |
| LINALYL ACETATE SYNTHETIC (3,7-dimethylocta-1,6-dien-3-yl acetate) | 2676 |
| BUTYL CYCLOHEXYL ACETATE PARA (4-(tert-butyl)cyclohexyl acetate) | 2526 |
| CYCLOHEXYL SALICYLATE (cyclohexyl 2-hydroxybenzoate) | 2454 |
| ALDEHYDE C 12 LAURIC (dodecanal) | 2369 |
| APHERMATE (1-(3,3-dimethylcyclohexyl)ethyl formate) | 2320 |
| GERANYL ISOBUTYRATE ((E)-3,7-dimethylocta-2,6-dien-1-yl isobutyrate) | 1972 |
| CITRONELLYL ACETATE (3,7-dimethyloct-6-en-1-yl acetate) | 1744 |
| ALDEHYDE MANDARINE ((E)-dodec-2-enal) | 1675 |
| BORNYL ACETATE ((2S,4S)-1,7,7-trimethylbicyclo[2.2.1]heptan-2-yl acetate) | 1498 |
| VIRIDINE ((2,2-dimethoxyethyl)benzene) | 1437 |
| CITRONELLYL FORMATE (3,7-dimethyloct-6-en-1-yl formate) | 1414 |
| PIVAROSE (2,2-dimethyl-2-pheylethyl propanoate) | 1206 |
| MENTHOL NATURAL (2-isopropyl-5-methylcyclohexanol) | 1177 |
| AMBERMAX (1,3,4,5,6,7-hexahydro-.beta.,1,1,5,5-pentamethyl-2H-2,4a-Methanonaphthalene-8-ethanol) | 1066 |
| BUTYL BUTYRO LACTATE (1-butoxy-1-oxopropan-2-yl butyrate) | 999 |
| CITRATHAL R ((Z)-1,1-diethoxy-3,7-dimethylocta-2,6-diene) | 995 |
| HABANOLIDE ((E)-oxacyclohexadec-12-en-2-one) | 991 |
| INDOFLOR (4,4a,5,9b-tetrahydroindeno[1,2-d][1,3]dioxine) | 830 |
| CORANOL (4-cyclohexyl-2-methylbutan-2-ol) | 740 |
| CARYOPHYLLENE ((Z)-4,11,11-trimethyl-8-methylenebicyclo[7.2.0]undec-4-ene) | 609 |
| GERANYL ACETATE ((E)-3,7-dimethylocta-2,6-dien-1-yl acetate) | 593 |
| PARADISAMIDE (2-ethyl-N-methyl-N-(m-tolyl)butanamide) | 550 |
| FIXOLIDE (1-(3,5,5,6,8,8-hexamethyl-5,6,7,8-tetrahydronaphthalen-2-yl)ethanone) | 550 |
| NERYL ACETATE HC ((Z)-3,7-dimethylocta-2,6-dien-1-yl acetate) | 472 |
| DIMETHYL BENZYL CARBINOL (2-methyl-1-phenylpropan-2-ol) | 264 |
| HEXYL CINNAMIC ALDEHYDE ((E)-2-benzylideneoctanal) | 192 |
| NEROLIDYLE ((Z)-3,7,11-trimethyldodeca-1,6,10-trien-3-yl acetate) | 175 |

It is preferred that an encapsulated perfume composition of the present invention contains at least 3, more particularly at least 5, still more particularly at least 7, and more particularly still, at least 9 GROUP 4 perfume ingredients.

Those encapsulated perfume compositions described hereinabove additionally comprising GROUP 4 ingredients, and in particular at least 3, more particularly at least 5, still more particularly at least 7, and more particularly still, at least 9 GROUP 4 perfume ingredients represent additional aspects of the present invention.

Furthermore, fabric softener or conditioning compositions, particularly those containing structured surfactants; or solid or liquid laundry detergent compositions, and particularly those formats designed as unit dosage forms contained in pouches or pods, and often referred to in the art as "liquid tabs"; or harshly extractive media, including personal care cleansing compositions, such as shampoos, containing encapsulated perfume compositions described herein comprising GROUP 4 ingredients, form further embodiments of the present invention.

Where trivial names or trade names are used in relation to the specific perfume ingredients recited above, the applicant includes within the ambit of the invention not only proprietary perfume ingredients but also the corresponding generic ingredient. The skilled person will be entirely familiar with the correspondence between trade names, trivial names and more conventional nomenclature, such as IUPAC nomenclature, or the skilled person can easily find such correspondence in perfumery text books or other references such as the website thegoodscentscompany.com.

In a particular embodiment of the present invention, an encapsulated perfume composition is characterized in that the total Pre-Rub Odour Contribution of the encapsulated perfume ingredients is between $0.5 \times 10^6$ and $1.0 \times 10^7$, more particularly between $1 \times 10^6$ and $8 \times 10^6$ and more particularly still, between $1.5 \times 10^6$ and $6 \times 10^6$; and the distribution of RECON VOLTAE values of encapsulated perfume ingredients is such that 70 wt % or more, 80 wt % or more, 90 wt % or more of the perfume ingredients have known RECON VOLTAE values larger than 1200 Bohr$^3$; and from 0.1 to 30 wt %, from 1 to 20 wt %, from 1 to 10 wt % of perfume ingredients having known RECON VOLTAE values below 1200 Bohr$^3$.

In another particular embodiment, an encapsulated perfume composition is characterized in that the total Pre-Rub Odour Contribution of the encapsulated perfume ingredients is between $0.5 \times 10^6$ and $1.0 \times 10^7$, more particularly between $1 \times 10^6$ and $8 \times 10^6$ and more particularly still between $1.5 \times 10^6$ and $6 \times 10^6$, and more particularly still between $1.5 \times 10^6$ and $6 \times 10^6$; and the distribution of known RECON VOLTAE values of encapsulated perfume ingredients is such that 30 wt % or more, 35 wt % or more, 40 wt % or more of the perfume ingredients have known RECON VOLTAE values larger than 1540 Bohr$^3$; and 30 wt % or more, 40 wt % or more, 50 wt % or more of the perfume ingredients have known RECON VOLTAE values from 1200 Bohr$^3$ to 1540 Bohr$^3$; and from 0.1 to 30 wt %, from 1 to 20 wt %, from 1 to 10 wt % of perfume ingredients have known RECON VOLTAE values below 1200 Bohr$^3$.

In another particular embodiment an encapsulated perfume composition contains encapsulated perfume ingredients characterized by a total Pre-Rub Odour Contribution between $0.5 \times 10^6$ and $1.0 \times 10^7$, more particularly $1 \times 10^6$ and $8 \times 10^6$ and more particularly still $1.5 \times 10^6$ and $6 \times 10^6$; and the distribution of known RECON VOLTAE values of encapsulated perfume ingredients is such that from 0.5 to 30, from 1 to 25 wt %, from 5 to 20 wt % of at least one perfume ingredient have known RECON VOLTAE values above 1750 Bohr$^3$; and 20 to 60 wt %, 25 to 55 wt %, 30 to 50 wt % of the perfume ingredients have known RECON VOLTAE values from 1540 Bohr$^3$ to 1750 Bohr$^3$; and 5 to 50 wt %, 10 to 40 wt %, 15 to 30 wt % of the perfume ingredients have known RECON VOLTAE values from 1200 Bohr$^3$ to 1540 Bohr$^3$; and from 0.1 to 30 wt %, from 1 to 20 wt %, from 1 to 10 wt % of perfume ingredients have known RECON VOLTAE values below 1200 Bohr$^3$.

In another particular embodiment an encapsulated perfume composition contains encapsulated perfume ingredients characterized by a total Pre-Rub Odour Contribution between $0.5 \times 10^6$ and $1.0 \times 10^7$, more particularly between $1 \times 10^6$ and $8 \times 10^6$ and more particularly still between $1.5 \times 10^6$ and $6 \times 10^6$; and the distribution of known RECON VOLTAE values of encapsulated perfume ingredients is such that 70 wt % or more, 80 wt % or more, 90 wt % or more of the perfume ingredients have known RECON VOLTAE values larger than 1750 Bohr$^3$; and from 0.1 to 30 wt %, from 1 to 20 wt %, from 1 to 10 wt % of the perfume ingredients have RECON VOLTAE values below 1750 Bohr$^3$.

RECON VOLTAE and $\log_{10}$ Kcaps values for other perfume ingredients, one or more of which may be employed in encapsulated perfume compositions according to the present invention, are set forth in the following table.

| Ingredient (NAME (IUPAC name)) | RECON_VOLTAE | Log Kcaps |
|---|---|---|
| ACETAL CD ((2-benzyl-1,3-dioxolan-4-yl)methanol) | 1387 | −4.0 |
| ACETAL E ((2-(1-ethoxyethoxy)ethyl)benzene) | 1531 | −1.1 |
| ACETAL R ((2-(1-propoxyethoxy)ethyl)benzene) | 1661 | −1.2 |
| ACETANISOLE (1-(4-methoxyphenyl)ethanone) | 1114 | −2.3 |
| ACETATE PA (allyl 2-phenoxyacetate) | 1407 | −3.5 |
| ACETOIN (3-hydroxybutan-2-one) | 690 | −1.4 |
| ACETOPHENONE (acetophenone) | 923 | −1.5 |
| ACETYL CARYOPHYLLENE ((Z)-4,11,11-trimethyl-8-methylenebicyclo[7.2.0]undec-4-ene) | 2092 | −1.0 |
| ACETYL ISOEUGENOL CRYSTALS ((E)-2-methoxy-4-(prop-1-en-1-yl)phenyl acetate) | 1526 | −2.8 |
| AGARBOIS (N-ethyl-N-(m-tolyl)propionamide) | 1537 | −3.0 |
| ALCOHOL C 10 DECYLIC (decan-1-ol) | 1432 | −2.7 |
| ALCOHOL C 12 LAURIC (dodecan-1-ol) | 1690 | −2.5 |
| ALCOHOL C 13 OXO (tridecan-1-ol) | 1819 | −2.4 |
| ALCOHOL C 6 HEXYLIC (hexan-1-ol) | 915 | −2.9 |
| ALCOHOL C 8 OCTYLIC (octan-1-ol) | 1173 | −3.0 |
| ALCOHOL C 9 NONYLIC (nonan-1-ol) | 1302 | −3.0 |
| ALDEHYDE C 6 HEXYLIC FOOD GRADE (hexan-1-ol) | 885 | −2.8 |
| ALDEHYDE C 7 HEPTYLIC (heptanal) | 1016 | −2.7 |
| ALDEHYDE C 8 OCTYLIC FOOD GRADE (octanal) | 1145 | −2.7 |
| ALDEHYDE C 9 ISONONYLIC (3,5,5-trimethylhexanal) | 1317 | −2.5 |
| ALDEHYDE C 9 NONYLIC FOOD GRADE (nonanal) | 1274 | −2.8 |
| ALICATE (2,6-dimethylheptan-4-yl acetate) | 1605 | −1.8 |
| ALLYLCAPROATE (allyl hexanoate) | 1307 | −1.8 |
| AMBERKETAL (3,8,8,11a-tetramethyldodecahydro-1H-3,5a-epoxynaphtho[2,1-c]oxepine) | 2339 | −4.0 |
| AMBRETTOLIDE ((Z)-oxacycloheptadec-10-en-2-one) | 2108 | −5.0 |
| AMBRINOL (2,5,5-trimethyl-1,2,3,4,4a,5,6,7-octahydronaphthalen-2-ol) | 1651 | −2.3 |
| AMBROCENIDE ((4aR,5R,7aS,9R)-Octahydro-2,2,5,8,8,9a-hexamethyl-4H-4a,9-methanoazuleno[5,6-d]-1,3-dioxole) | 2339 | −2.1 |
| AMBROFIX (3a,6,6,9a-tetramethyldodecahydronaphtho[2,1-b]furan) | 2039 | −2.0 |
| AMBROXAN (3a,6,6,9a-tetramethyl-2,4,5,5a,7,8,9,9b-octahydro-1H-benzo[e][1]benzofuran) | 2039 | −2.0 |
| AMYL ACETATE (pentyl acetate) | 1075 | −1.2 |
| AMYL BENZOATE (pentyl benzoate) | 1494 | −1.2 |
| AMYL BUTYRATE (pentyl butanoate) | 1333 | −1.6 |
| AMYL CINNAMIC ALDEHYDE ((Z)-2-benzylideneheptanal) | 1649 | −2.8 |
| AMYL PHENYL ACETATE (pentyl 2-phenylacetate) | 1623 | −2.9 |
| AMYL VINYL CARBINOL (oct-1-en-3-ol) | 1149 | −2.9 |
| ANAPEAR ((E)-methyl octa-4,7-dienoate) | 1257 | −2.8 |
| ANATOLYL (phenethyl 2-methylbutanoate) | 1625 | −2.1 |
| ANETHOLE ((E)-1-methoxy-4-(prop-1-en-1-yl)benzene) | 1175 | −1.7 |
| ANISYL ACETATE (4-methoxybenzyl acetate) | 1309 | −3.6 |
| ANISYL ALCOHOL ((4-methoxyphenyl)methanol) | 1021 | −4.0 |
| ANTHER ((2-(isopentyloxy)ethyl)benzene) | 1597 | −1.3 |
| AUBEPINE PARA CRESOL (4-methoxybenzaldehyde) | 981 | −2.1 |

-continued

| Ingredient (NAME (IUPAC name)) | RECON_VOLTAE | Log Kcaps |
|---|---|---|
| AZARBRE (3,5-diethyl-2,5-dimethylcyclohex-2-enone) | 1591 | −1.5 |
| BENZALDEHYDE (benzaldehyde) | 790 | −0.9 |
| BENZOPHENONE (benzophenone) | 1347 | −1.5 |
| BENZYL ACETATE (benzyl acetate) | 1118 | −1.6 |
| BENZYL ACETONE (4-phenylbutan-2-one) | 1180 | −1.8 |
| BENZYL ALCOHOL (phenylmethanol) | 831 | −2.6 |
| BENZYL BENZOATE (benzyl benzoate) | 1539 | −3.6 |
| BENZYL BUTYRATE (benzyl butanoate) | 1378 | −1.7 |
| BENZYL CINNAMATE (benzyl 3-phenylprop-2-enoate) | 1748 | −2.5 |
| BENZYL FORMATE (benzyl formate) | 984 | −2.0 |
| BENZYL ISOBUTYRATE (benzyl isobutanoate) | 1374 | −1.4 |
| BENZYL ISOVALERATE (benzyl 3-methylbutanoate) | 1510 | −1.4 |
| BENZYL METHYL ETHER ((methoxymethyl)benzene) | 960 | −2.2 |
| BENZYL PHENYL ACETATE (benzyl 2-phenylacetate) | 1669 | −5.2 |
| BENZYL PROPIONATE (benzyl propionate) | 1249 | −1.6 |
| BENZYL SALICYLATE (benzyl 2-hydroxybenzoate) | 1601 | −5.0 |
| BICYCLO NONALACTONE (octahydro-2H-chromen-2-one) | 1160 | −2.6 |
| BIGARADE OXIDE ((4aS,6R,7S,8aR)-3,3,6,7-tetramethyl-2,4,4a,5,6,7,8,8a-octahydrochromene) | 1610 | −1.2 |
| BISABOLENE ((E)-1-methyl-4-(6-methylhepta-2,5-dien-2-yl)cyclohex-1-ene) | 1804 | −0.8 |
| BORNEOL CRYSTALS ((1S,2S,4S)-1,7,7-trimethylbicyclo[2.2.1]heptan-2-ol) | 1345 | −2.0 |
| BOURGEONAL (3-(4-(tert-butyl)phenyl)propanal) | 1609 | −3.2 |
| BUCCOXIME ((1R,5S,E)-1,5-dimethylbicyclo[3.2.1]octan-8-one oxime) | 1402 | −2.3 |
| BUTYL ISOBUTYRATE, ISO- (2-methylpropyl 2-methylpropanoate) | 1202 | −1.7 |
| BUTYL QUINOLINE SECONDARY (6-(sec-butyl)quinoline) | 1466 | −1.8 |
| CALMODE (1,2,4-trimethoxy-5-propylbenzene) | 1602 | −3.3 |
| CALONE 1951 (7-methyl-2H-benzo[b][1,4]dioxepin-3(4H)-one) | 1228 | −0.9 |
| CALYPSONE (6-methoxy-2,6-dimethyloctanal) | 1596 | −2.5 |
| CAMPHENE ((1S,4R)-2,2-dimethyl-3-methylenebicyclo[2.2.1]heptane) | 1202 | −0.3 |
| CAMPHOR ((1S,4S)-1,7,7-trimethylbicyclo[2.2.1]heptan-2-one) | 1301 | −1.9 |
| CANTHOXAL (3-(4-methoxyphenyl)-2-methylpropanal) | 1372 | −3.3 |
| CARAMEL LACTONE (3-hydroxy-4,5-dimethylfuran-2(5H)-one) | 885 | −3.5 |
| CARVACROL (5-isopropyl-2-methylphenol) | 1217 | −2.0 |
| CARVONE LAEVO (2-methyl-5-(prop-1-en-2-yl)cyclohex-2-enone) | 1249 | −1.2 |
| CASSIONE (4-(1-3-benzodioxol-5-yl)-2-butanone) | 1360 | −2.8 |
| CELERY KETONE (3-methyl-5-propylcyclohex-2-enone) | 1262 | −1.4 |
| CENTIFOLYL (2-phenylethyl 2,2-dimethylpropanoate) | 1665 | −2.0 |
| CEPIONATE (methyl 2-(3-oxo-2-pentylcyclopentyl)acetate) | 1784 | −2.4 |
| CETALOX (3a,6,6,9a-tetramethyl-2,4,5,5a,7,8,9,9b-octahydro-1H-benzo[e][1]benzofuran) | 2039 | −2.1 |
| CETONAL (2-methyl-4-(2,6,6-trimethylcyclohex-2-en-1-yl)butanal) | 1825 | −2.6 |
| CETONE ALPHA ((E)-3-methyl-4-(2,6,6-trimethylcyclohex-2-en-1-yl)but-3-en-2-one) | 1782 | −1.6 |
| CETONE V ((E)-1-(2,6,6-trimethylcyclohex-2-en-1-yl)hepta-1,6-dien-3-one) | 2028 | −3.3 |
| CINNAMALVA ((E)-3-phenylprop-2-en-1-yl acetate) | 1075 | −2.0 |
| CINNAMIC ALCOHOL ((E)-3-phenylprop-2-en-1-ol) | 1048 | −2.4 |
| CINNAMIC ALDEHYDE ((2E)-3-phenylprop-2-enal) | 1001 | −2.0 |
| CINNAMYL ACETATE ((E)-3-phenylprop-2-en-1-yl acetate) | 1334 | −1.7 |
| CINNAMYL CINNAMATE (3-phenylprop-2-enyl 3-phenylprop-2-enoate) | 1967 | −3.2 |
| CITRAL DIMETHYL ACETAL ((E)-1,1-dimethoxy-3,7-dimethylocta-2,6-diene) | 1680 | −1.9 |
| CITRONELLYL ISOBUTYRATE (3,7-dimethyloct-6-en-1-yl isobutanoate) | 1936 | −1.3 |
| CITRONELLYL OXYACETALDEHYDE (2-((3,7-dimethyloct-6-en-1-yl)oxy)acetaldehyde) | 1679 | −3.4 |
| CIVETTON E ((Z)-cycloheptadec-9-enone) | 2180 | −2.5 |
| CLARITONE (2,4,4,7-tetramethyloct-6-en-3-one) | 1658 | −0.9 |
| CONIFERAN (2-(tert-pentyl)cyclohexyl acetate) | 1807 | −1.9 |
| CORPS CASSIS (2-(2-mercaptopropan-2-yl)-5-methylcyclohexanone) | 1483 | −2.2 |
| CORPS PAMPLEMOUSSE PURE ((4S)-4,7,7-trimethyl-6-thiabicyclo[3.2.1]octane) | 1374 | 0.1 |
| CORYLONE DRIED (2-hydroxy-3-methylcyclopent-2-enone) | 822 | −2.8 |
| COUMARIN (2H-chromen-2-one) | 985 | −1.9 |
| CREOSOL (2-methoxy-4-methylphenol) | 1021 | −2.6 |
| CRESOL PARA (p-cresol) | 830 | −1.8 |
| CRESYL ACETATE PARA (p-tolyl acetate) | 1115 | −2.2 |
| CRESYL CAPRYLATE PARA (p-tolyl octanoate) | 1892 | −2.6 |

| Ingredient (NAME (IUPAC name)) | RECON_VOLTAE | Log Kcaps |
|---|---|---|
| CRESYL ISOBUTYRATE PARA (p-tolyl isobutanoate) | 1374 | −1.9 |
| CRESYL METHYL ETHER PARA (1-methoxy-4-methylbenzene) | 959 | −1.8 |
| CRESYL PHENYL ACETATE PARA (p-tolyl 2-phenylacetate) | 1666 | −4.9 |
| CUMIN NITRILE (4-isopropylbenzonitrile) | 1246 | −1.2 |
| CUMINIC ALDEHYDE (4-isopropylbenzaldehyde) | 1177 | −1.0 |
| CUMINYL ALCOHOL ((4-isopropylphenyl)methanol) | 1217 | −2.8 |
| CYCLAL C (2,4-dimethylcyclohex-3-enecarbaldehyde) | 1138 | −1.9 |
| CYCLEMONE A (8,8-dimethyl-1,2,3,4,5,6,7,8-octahydronaphthalene-2-carbaldehyde) | 1610 | −2.4 |
| CYCLOHEXAL (4-(4-hydroxy-4-methylpentyl)cyclohex-3-enecarbaldehyde) | 1719 | −3.7 |
| CYCLOHEXYL ETHYL ACETATE (2-cyclohexylethyl acetate) | 1371 | −1.9 |
| CYCLOMETHYLENE CITRONELLOL (3-(4-methylcyclohex-3-en-1-yl)butan-1-ol) | 1425 | −1.9 |
| CYDRANE (hexyl 2-methylbutanoate) | 1588 | −0.5 |
| CYMENE PARA (1-methyl-4-propan-2-ylbenzene) | 1155 | −0.6 |
| CYPRISATE (methyl 1,4-dimethylcyclohexanecarboxylate) | 2826 | −2.0 |
| DAMASCONE BETA ((E)-1-(2,6,6-trimethylcyclohex-1-en-1-yl)but-2-en-1-one) | 1655 | −1.3 |
| DECADIENAL ((2E,4E)-deca-2,4-dienal) | 1309 | −2.2 |
| DECALACTONE DELTA (6-pentyltetrahydro-2H-pyran-2-one) | 1378 | −3.2 |
| DECALACTONE GAMMA (5-hexyloxolan-2-one) | 1386 | −3.7 |
| DECANONITRILE (decanenitrile) | 1464 | −1.5 |
| DECATONE (6-isopropyloctahydronaphthalen-2(1H)-one) | 1610 | −2.2 |
| DECEN-1-AL, CIS-4- ((Z)-dec-4-enal) | 1363 | −2.8 |
| DECENAL-2-TRANS ((E)-dec-2-enal) | 1356 | −2.1 |
| DECENAL-9 (9-decenal) | 1369 | −3.3 |
| DELTA-3 CARENE ((1S,6S)-3,7,7-trimethylbicyclo[4.1.0]hept-3-ene) | 1200 | −1.0 |
| DIETHYL MALONATE (diethyl propanedioate) | 1152 | −1.4 |
| DIHEXYL FUMARATE (dihexyl-but-2-enedioate) | 2263 | −1.7 |
| DIHYDRO AMBRATE (2-(sec-butyl)-1-vinylcyclohexyl acetate) | 1865 | −2.4 |
| DIHYDRO EUGENOL (2-methoxy-4-propylphenol) | 1281 | −2.5 |
| DIHYDRO FARNESAL ((Z)-3,7,11-trimethyldodeca-6,10-dienal) | 1967 | −4.0 |
| DIHYDRO IONONE BETA (4-(2,6,6-trimethylcyclohex-1-en-1-yl)butan-2-one) | 1695 | −1.5 |
| DIHYDRO LINALOOL (3,7-dimethyloct-6-en-3-ol) | 1403 | −2.0 |
| DIHYDRO MYRCENOL (2,6-dimethyloct-7-en-2-ol) | 1410 | −2.8 |
| DIHYDRO MYRCENYL ACETATE (2,6-dimethyloct-7-en-2-yl acetate) | 1695 | −2.3 |
| DIHYDRO TERPINEOL (2-(4-methylcyclohexyl)propan-2-ol) | 1356 | −2.0 |
| DIHYDRO TERPINYL ACETATE (2-(4-methylcyclohexyl)propan-2-yl acetate) | 1639 | −1.5 |
| DIMETHYL ANTHRANILATE (methyl 2-(methylamino)benzoate) | 1206 | −3.0 |
| DIMETHYL HYDROQUINONE CRYSTALS (1,4-dimethoxybenzene) | 1022 | −2.9 |
| DIMETHYL PHENYL ETHYL CARBINOL (2-methyl-4-phenylbutan-2-ol) | 1352 | −2.2 |
| DIMYRCETOL (2,6-dimethyloct-7-en-2-ol) | 2969 | −1.9 |
| DIPHENYL METHANE (diphenylmethane) | 1320 | −1.4 |
| DIPHENYL OXIDE (oxydibenzene) | 1260 | −1.2 |
| DISPIRONE (7,9-dimethylspiro[5.5]undecan-3-one) | 1648 | −2.4 |
| DODECALACTONE DELTA (6-heptyltetrahydro-2H-pyran-2-one) | 1636 | −3.4 |
| DODECALACTONE GAMMA (5-octyloxolan-2-one) | 1644 | −3.9 |
| ESTRAGOLE (1-allyl-4-methoxybenzene) | 1180 | −1.7 |
| ETHYL 2,4-DECADIENOATE ((2E,4Z)-ethyl deca-2,4-dienoate) | 1625 | −1.5 |
| ETHYL ACETATE (ethyl acetate) | 685 | −0.7 |
| ETHYL ACETO ACETATE (ethyl 3-oxobutanoate) | 964 | −1.0 |
| ETHYL AMYL KETONE (octan-3-one) | 1146 | −1.3 |
| ETHYL BENZOATE (ethyl benzoate) | 1106 | −1.7 |
| ETHYL BUTYRATE (ethyl butanoate) | 945 | −1.2 |
| ETHYL CINNAMATE (ethyl 3-phenylprop-2-enoate) | 1317 | −1.0 |
| ETHYL ISOAMYL KETONE (6-methylheptan-3-one) | 1149 | −1.2 |
| ETHYL ISOBUTYRATE (ethyl 2-methylpropionate) | 940 | −0.8 |
| ETHYL ISOVALERATE (ethyl 3-methylbutanoate) | 1077 | −1.3 |
| ETHYL LAITONE (8-ethyl-1-oxaspiro[4.5]decan-2-one) | 1429 | −2.2 |
| ETHYL MALTOL (2-ethyl-3-hydroxy-4H-pyran-4-one) | 985 | −3.7 |
| ETHYL METHYL-2-BUTYRATE (ethyl 2-methylbutanoate) | 1069 | −0.6 |
| ETHYL PELARGONATE (ethyl nonanoate) | 1591 | −2.4 |
| ETHYL PHENYL ACETATE (ethyl 2-phenylacetate) | 1236 | −2.6 |
| ETHYL PHENYL GLYCIDATE (ethyl 3-phenyloxirane-2-carboxylate) | 1347 | −1.9 |
| ETHYL PROPIONATE (ethyl propionate) | 816 | −2.0 |
| ETHYL SALICYLATE (ethyl 2-hydroxybenzoate) | 1168 | −1.2 |
| ETHYL VANILLIN (3-ethoxy-4-hydroxybenzaldehyde) | 1168 | −2.2 |

| Ingredient (NAME (IUPAC name)) | RECON_VOLTAE | Log Kcaps |
|---|---|---|
| ETHYL-2 DIMETHYL-3,5 PYRAZINE (2-ethyl-3,5-dimethylpyrazine) | 1100 | −2.4 |
| ETHYLENE BRASSYLATE (1,4-dioxacycloheptadecane-5,17-dione) | 2096 | −3.0 |
| EUGENOL PURE (4-allyl-2-methoxyphenol) | 1242 | −2.8 |
| EUGENYL ACETATE (4-allyl-2-methoxyphenyl acetate) | 1527 | −3.5 |
| EVERNYL (methyl 2,4-dihydroxy-3,6-dimethylbenzoate) | 1362 | −3.6 |
| FARNESENE ((E)-7,11-dimethyl-3-methylenedodeca-1,6,10-triene) | 1863 | −2.2 |
| FARNESOL ((2E,6Z)-3,7,11-trimethyldodeca-2,6,10-trien-1-ol) | 1962 | −4.5 |
| FENCHONE ALPHA (1,3,3-trimethylbicyclo[2.2.1]heptan-2-one) | 1301 | −1.6 |
| FENNALDEHYDE (3-(4-methoxyphenyl)-2-methylpropanal) | 1372 | −3.3 |
| FLEURANIL (3-(4-ethylphenyl)-2,2-dimethylpropanenitrile) | 1674 | −1.7 |
| FLORALYM (2,6-dimethyloct-7-en-2-ol) | 1410 | −2.8 |
| FLORAMAT (2-(tert-butyl)cyclohexyl ethyl carbonate) | 1863 | −0.5 |
| FLORIDILE ((E)-undec-9-enenitrile) | 1560 | −2.8 |
| FLOROL (2-isobutyl-4-methyltetrahydro-2H-pyran-4-ol) | 1432 | −2.5 |
| FLOROSA (tetrahydro-4-methyl-2-(2-methylpropyl)-2H-pyran-4-ol) | 1432 | −2.5 |
| FLORYMOSS ((Z)-1-(cycloct-3-en-1-yl)propan-1-ol) | 1451 | −2.9 |
| FOLENOX (4,4,8,8-tetramethyloctahydro-4a,7-methanonaphtho[1,8a-b]oxirene) | 1865 | −1.5 |
| FOLIONE (methyl oct-2-ynoate) | 1246 | −1.7 |
| FOLROSIA (4-isopropylcyclohexanol) | 1229 | −2.3 |
| FRAISTONE (ethyl 2-(2,4-dimethyl-1,3-dioxolan-2-yl)acetate) | 1440 | −3.1 |
| FRESCILE (3-methyldodecanenitrile) | 1859 | −1.9 |
| FRUCTONE (ethyl 2-(2-methyl-1,3-dioxolan-2-yl)acetate) | 1307 | −3.3 |
| GALAXOLIDE (4,6,6,7,8,8-hexamethyl-1,3,4,6,7,8-hexahydrocyclopenta[g]isochromene) | 2160 | −4.3 |
| GARDAMIDE (N,2-dimethyl-N-phenylbutanamide) | 1534 | −2.5 |
| GARDENOL (1-phenylethyl acetate) | 1246 | −1.7 |
| GEORGYWOOD (1-(1,2,8,8-tetramethyl-1,2,3,4,5,6,7,8-octahydronaphthalen-2-yl)ethanone) | 2037 | −1.3 |
| GERANODYLE (2-(2-hydroxypropan-2-yl)-5-methylcyclohexanol) | 1420 | −4.0 |
| GERANYL ACETONE ((E)-6,10-dimethylundeca-5,9-dien-2-one) | 1705 | −1.1 |
| GERANYL CROTONATE ((E)-3,7-dimethylocta-2,6-dien-1-yl but-2-enoate) | 1862 | −2.3 |
| GERANYL FORMATE ((E)-3,7-dimethylocta-2,6-dien-1-yl formate) | 1510 | −1.6 |
| GERANYL PHENYL ACETATE ((E)-3,7-dimethylocta-2,6-dien-1-yl 2-phenylacetate) | 2194 | −3.8 |
| GERANYL PROPIONATE ((E)-3,7-dimethylocta-2,6-dien-1-yl propionate) | 1773 | −1.6 |
| GLYCOLIERRAL (2-(8-isopropyl-6-methylbicyclo[2.2.2]oct-5-en-2-yl)-1,3-dioxolane) | 1854 | −1.6 |
| GRISALVA (3a-ethyl-6,6,9a-trimethyldodecahydronaphtho[1,2-c]furan) | 2203 | −2.6 |
| GRISAMBROL B (ethyl picolinate) | 1076 | −2.4 |
| GUAIACOL (2-methoxyphenol) | 893 | −2.9 |
| GUAIYL ACETATE (2-(3,8-dimethyl-1,2,3,4,5,6,7,8-octahydroazulen-5-yl)propan-2-yl acetate) | 2161 | −1.9 |
| GYRANE (2-butyl-4,6-dimethyl-3,6-dihydro-2H-pyran) | 1446 | −2.1 |
| HELIOTROPINE (benzo[d][1,3]dioxole-5-carbaldehyde) | 971 | −1.4 |
| HELVETOLIDE (2-(1-(3,3-dimethylcyclohexyl)ethoxy)-2-methylpropyl propionate) | 2388 | −3.1 |
| HEPTALACTONE GAMMA (5-propyloxolan-2-one) | 996 | −2.2 |
| HERBAVERT (3-ethoxy-1,1,5-trimethylcyclohexane) | 1520 | −1.4 |
| HERBOXANE (2-butyl-4,4,6-trimethyl-1,3-dioxane) | 1562 | −3.7 |
| HERCOLYN D (methyl 7-isopropyl-1,4a-dimethyl-1,2,3,4,4a,4b,5,6,7,8,10,10a-dodecahydrophenanthrene-1-carboxylate) | 2656 | −5.0 |
| HEXENAL-2-TRANS (E-hex-2-enal) | 841 | −1.7 |
| HEXENOL-2-TRANS ((E)-hex-2-en-1-ol) | 886 | −2.5 |
| HEXENOL-3-CIS ((Z)-hex-3-en-1-ol) | 876 | −2.5 |
| HEXENYL ACETATE CIS (cis-hex-3-enyl acetate) | 1165 | −1.4 |
| HEXENYL HEXENOATE CIS-3 ((Z)-(Z)-hex-3-en-1-yl hex-3-enoate) | 1644 | −3.4 |
| HEXENYL-3-CIS ACETATE ((Z)-hex-3-en-1-yl acetate) | 1162 | −1.4 |
| HEXENYL-3-CIS BENZOATE ((Z)-hex-3-en-1-yl benzoate) | 1584 | −2.4 |
| HEXENYL-3-CIS FORMATE ((Z)-hex-3-en-1-yl formate) | 1029 | −1.9 |
| HEXENYL-3-CIS ISOBUTYRATE ((Z)-hex-3-en-1-yl isobutanoate) | 1420 | −0.7 |
| HEXENYL-3-CIS METHYL-2-BUTYRATE ((Z)-hept-3-en-1-yl 2-methyl butanoate) | 1549 | −1.5 |
| HEXENYL-3-CIS PROPIONATE ((Z)-hex-3-en-1-yl propionate) | 1292 | −1.2 |

-continued

| Ingredient (NAME (IUPAC name)) | RECON_VOLTAE | Log Kcaps |
|---|---|---|
| HEXENYL-3-CIS SALICYLATE ((Z)-hex-3-en-1-yl 2-hydroxybenzoate) | 1646 | −3.5 |
| HEXENYL-3-CIS TIGLATE ((E)-(Z)-hex-3-en-1-yl 2-methylbut-2-enoate) | 1505 | −1.8 |
| HEXENYL-3-TRANS ACETATE ((E)-hex-3-enyl] acetate) | 1162 | −1.5 |
| HEXYL ACETATE (hexyl acetate) | 1202 | −1.2 |
| HEXYL BENZOATE (hexyl benzoate) | 1623 | −1.4 |
| HEXYL BUTYRATE (hexyl butanoate) | 1462 | −1.8 |
| HEXYL PROPIONATE (hexyl propionate) | 1333 | −1.5 |
| HOMOFURONOL (2-ethyl-4-hydroxy-5-methylfuran-3(2H)-one) | 1025 | −3.6 |
| HYDRATROPIC ALDEHYDE (2-phenylpropanal) | 1048 | −2.4 |
| HYDROXYCITRONELLAL DIMETHYL ACETAL (8,8-dimethoxy-2,6-dimethyloctan-2-ol) | 1831 | −3.0 |
| HYDROXYCITRONELLAL (7-hydroxy-3,7-dimethyloctanal) | 1472 | −4.2 |
| IRISANTHEME ((E)-3-methyl-4-(2,6,6-trimethylcyclohex-2-en-1-yl)but-3-en-2-one) | 1806 | −1.7 |
| IRIVAL ((E)-non-2-enenitrile) | 1301 | −1.4 |
| ISO CYCLO GERANIOL ((2,4,6-trimethylcyclohex-3-en-1-yl)methanol) | 1295 | −1.6 |
| ISOAMYL ACETATE (isopentyl acetate) | 1075 | −1.2 |
| ISOAMYL BUTYRATE (isopentyl butanoate) | 1335 | −0.5 |
| ISOAMYL PROPIONATE (isopentyl propionate) | 1206 | −1.1 |
| ISOBUTYL BENZOATE (2-methylpropyl benzoate) | 1368 | −1.4 |
| ISOBUTYL ISOBUTYRATE (2-methylpropyl 2-methylpropanoate) | 1202 | −1.7 |
| ISOBUTYL METHOXY PYRAZINE (2-methylpropyl 3-methoxypyrazine) | 1311 | −2.2 |
| ISOBUTYL PHENYLACETATE (2-methylpropyl 2-phenylacetate) | 1497 | −2.0 |
| ISOBUTYL QUINOLINE-2 (6-butan-2-yl-quinoline) | 1473 | −1.6 |
| ISOBUTYL SALICYLATE (isobutyl 2-hydroxybenzoate) | 1430 | −1.6 |
| ISOEUGENOL ((E)-2-methoxy-4-(prop-1-en-1-yl)phenol) | 1238 | −2.5 |
| ISOJASMONE T (2-hexylcyclopent-2-enone) | 1411 | −2.0 |
| ISOLONGIFOLANONE (2,2,7,7-tetramethyltricyclo[6.2.1.01,6]undecan-5-one) | 1900 | −1.5 |
| ISOMENTHONE DL (2-isopropyl-5-methylcyclohexanone) | 1315 | −1.5 |
| ISONONANOL (3,5,5-trimethylhexan-1-ol) | 1345 | −2.4 |
| ISOPENTYRATE (4-methylpent-4-en-2-yl isobutanoate) | 1434 | −1.2 |
| ISOPROPYL QUINOLINE (6-isopropylquinoline) | 1336 | −1.7 |
| ISOPULEGOL (5-methyl-2-(prop-1-en-2-yl)cyclohexanol) | 1315 | −2.3 |
| ISORALDEINE CETONE ALPHA ((E)-3-methyl-4-(2,6,6-trimethylcyclohex-2-en-1-yl)but-3-en-2-one) | 1806 | −1.6 |
| JASMAL (3-pentyltetrahydro-2H-pyran-4-yl acetate) | 1709 | −4.3 |
| JASMATONE (2-hexylcyclopentanone) | 1439 | −2.2 |
| JASMIN LACTONE DELTA ((Z)-6-(pent-2-en-1-yl)tetrahydro-2H-pyran-2-one) | 1343 | −2.4 |
| JASMIN LACTONE GAMMA ((Z)-5-(hex-3-en-1-yl)-5-methyloxolan-2-one) | 1472 | −2.4 |
| JASMOLACTONE ((E)-6-(pent-3-en-1-yl)tetrahydro-2H-pyran-2-one) | 1341 | −2.5 |
| JASMONYL (3-butyl-5-methyltetrahydro-2H-pyran-4-yl acetate) | 1708 | −3.1 |
| JASMOPYRANE (3-pentyltetrahydro-2H-pyran-4-yl acetate) | 1709 | −3.0 |
| JAVANOL ((1-methyl-2-((1,2,2-trimethylbicyclo[3.1.0]hexan-3-yl)methyl)cyclopropyl)methanol) | 1930 | −3.0 |
| KEFARENE (1-(4-methoxy-2,2,6,6-tetramethylcyclohex-3-en-1-yl)ethanone) | 1807 | −2.0 |
| KEPHALIS (4-(1-ethoxyvinyl)-3,3,5,5-tetramethylcyclohexanone) | 1936 | −2.4 |
| KOHINOOL (3,4,5,6,6-pentamethylheptan-2-ol) | 1751 | −2.1 |
| LABIENONE ((E)-2,4,4,7-tetramethylnona-6,8-dien-3-one) | 1748 | −1.4 |
| LABIENOXIME ((3E,6E)-2,4,4,7-tetramethylnona-6,8-dien-3-one oxime) | 1850 | −4.0 |
| LACTOSCATONE (2,8,8-trimethyloctahydro-1H-4a,2-(epoxymethano)naphthalen-10-one) | 1804 | −2.6 |
| LAITONE (8-isopropyl-1-oxaspiro[4.5]decan-2-one) | 1561 | −2.2 |
| LIMETOL (2,2,6-trimethyl-6-vinyltetrahydro-2H-pyran) | 1332 | −1.3 |
| LINALOOL OXIDE (2-(5-methyl-5-vinyltetrahydrofuran-2-yl)propan-2-ol) | 1395 | −2.5 |
| LINALYL CINNAMATE (3,7-dimethylocta-1,6-dien-3-yl 3-phenylprop-2-enoate) | 2286 | −2.2 |
| LINALYL FORMATE (3,7-dimethylocta-1,6-dien-3-yl formate) | 1520 | −2.0 |
| LINALYL ISOBUTYRATE (3,7-dimethylocta-1,6-dien-3-yl isobutanoate) | 1911 | −1.4 |
| LINALYL PROPIONATE (3,7-dimethylocta-1,6-dien-3-yl propionate) | 1783 | −1.9 |
| LINDENOL (2-(4-methylcyclohex-3-en-1-yl)propan-2-ol) | 1307 | −1.7 |

-continued

| Ingredient (NAME (IUPAC name)) | RECON_VOLTAE | Log Kcaps |
|---|---|---|
| LONGIFOLENE STD ((3R,3aR,8R,8aS)-4,4,8-trimethyl-9-methylenedecahydro-3,8-methanoazulene) | 1799 | −1.0 |
| MACEAL (bicyclo[2.2.2]oct-5-ene-2-carboxaldehyde) | 1573 | −3.0 |
| MAGNOLAN (2,4-dimethyl-4,4a,5,9b-tetrahydroindeno[1,2-d][1,3]dioxine) | 1509 | −3.0 |
| MAHONIAL ((4E)-9-hydroxy-5,9-dimethyl-4-decenal) | 1685 | −3.5 |
| MAJANTOL (2,2-dimethyl-3-(m-tolyl)propan-1-ol) | 1507 | −2.4 |
| MALTOL (3-hydroxy-2-methyl-4H-pyran-4-one) | 854 | −3.9 |
| MARENIL (2-(4-(tert-butyl)phenyl)acetonitrile) | 1542 | −2.1 |
| MAYOL ((4-isopropylcyclohexyl)methanol) | 1345 | −2.7 |
| MEFRANAL (3-methyl-5-phenylpentanal) | 1443 | −2.7 |
| MEFROSOL (3-methyl-5-phenylpentan-1-ol) | 1471 | −3.5 |
| MELOZONE (tricyclo[5.2.1.02,6]decane-3-carbaldehyde) | 1260 | −1.9 |
| MENTHANYL ACETATE (2-(4-methylcyclohexyl)propan-2-yl acetate) | 1639 | −1.5 |
| METAMBRATE (2-(sec-butyl)-1-methylcyclohexyl acetate) | 1772 | −1.7 |
| METHOXY MELONAL (6-methoxy-2,6-dimethylheptanal) | 1468 | −2.5 |
| METHOXY PHENYL BUTANONE (4-(4-methoxyphenyl)butan-2-one) | 1372 | −2.6 |
| METHYL ACETOPHENONE (1-(p-tolyl)ethanone) | 1051 | −1.4 |
| METHYL AMYL KETONE (heptan-2-one) | 1015 | −1.0 |
| METHYL ANTHRANILATE (methyl 2-aminobenzoate) | 1077 | −4.0 |
| METHYL BENZOATE (methyl benzoate) | 981 | −2.3 |
| METHYL CAMOMILLE (butyl 2-methylpentanoate) | 1460 | −0.2 |
| METHYL CINNAMATE (methyl 3-phenylprop-2-enoate) | 1192 | −1.6 |
| METHYL CINNAMIC ALDEHYDE ((Z)-2-methyl-3-phenylacrylaldehyde) | 1132 | −1.9 |
| METHYL CRESOTATE PARA (methyl 2-hydroxy-5-methylbenzoate) | 1172 | −2.3 |
| METHYL DECALACTONE GAMMA (5-hexyl-5-methyloxolan-2-one) | 1517 | −2.5 |
| METHYL DIANTILIS (2-ethoxy-4-(methoxymethyl)phenol) | 1338 | −3.3 |
| METHYL DIHYDRO ISOJASMONATE (methyl 3-oxo-2-pentylcyclopentaneacetate) | 1784 | −1.8 |
| METHYL DIPHENYL ETHER (2-methoxy-1,1'-biphenyl) | 1386 | −1.9 |
| METHYL EPI JASMONATE ((Z)-methyl 2-(3-oxo-2-(pent-2-en-1-yl)cyclopentyl)acetate) | 1742 | −2.1 |
| METHYL GEOSMIN (4,4,8a-trimethyldecahydronaphthalen-4a-ol) | 1738 | −2.8 |
| METHYL HEPTENONE PURE (6-methylhept-5-en-2-one) | 1101 | −0.6 |
| METHYL HEXYL KETONE (octan-2-one) | 1144 | −1.2 |
| METHYL ISO EUGENOL ((E)-1,2-dimethoxy-4-(prop-1-en-1-yl)benzene) | 1366 | −3.0 |
| METHYL LAITONE (8-methyl-1-oxaspiro[4.5]decan-2-one) | 1299 | −2.0 |
| METHYL LINOLEATE ((9E,12E)-methyl octadeca-9,12-dienoate) | 2546 | −2.9 |
| METHYL METHYL BUTYRATE (methyl 2-methylbutanoate) | 944 | −2.2 |
| METHYL PARA-CRESOL (1-methoxy-4-methylbenzene) | 959 | −2.0 |
| METHYL PHENYL ACETATE (methyl 2-phenylacetate) | 1111 | −2.4 |
| METHYL QUINOLINE PARA (6-methylquinoline) | 1078 | −1.8 |
| METHYL SALICYLATE (methyl 2-hydroxybenzoate) | 1043 | −2.0 |
| METHYL TUBERATE PURE (4-methyl-5-pentyldihydrofuran-2(3H)-one) | 1385 | −2.6 |
| METHYL-2 BUTANOL-1 FR (2-methylbutan-1-ol) | 789 | −1.9 |
| METHYL-2-PENTENOIC ACID, 2- ((E)-2-methylpent-2-enoic acid) | 903 | −1.6 |
| METHYL-3 METHOXY-3 BUTANOL (3-methoxy-3-methylbutan-1-ol) | 981 | −3.0 |
| METHYLOCTYLACETALDEHYDE MOA (2-methyl-decanal) | 1530 | −2.6 |
| MOXALONE (1a,3,3,4,6,6-hexamethyl-1a,2,3,4,5,6,7,7a-octahydronaphtho[2,3-b]oxirene) | 1992 | −2.8 |
| MUSCENONE ((Z)-3-methylcyclopentadec-5-enone) | 2053 | −2.5 |
| MUSCONE (3-methylcyclopentadecanone) | 2095 | −2.5 |
| MUSK C14 (1,4-dioxacyclohexadecane-5,16-dione) | 1967 | −3.0 |
| MUSK R1 (1,7-dioxacycloheptadecan-8-one) | 2065 | −2.9 |
| MYRALDYL ACETATE ((4-(4-methylpent-3-en-1-yl)cyclohex-3-en-1-yl)methyl acetate) | 1928 | −1.6 |
| MYRCENE 90 (7-methyl-3-methyleneocta-1,6-diene) | 1259 | −0.4 |
| MYROXIDE (2,2-dimethyl-3-(3-methylpenta-2,4-dienyl)oxirane) | 1282 | −0.9 |
| MYSTIKAL (2-methylundecanoic acid) | 1722 | −5.0 |
| NEOCASPIRENE (10-isopropyl-2,7-dimethyl-1-oxaspiro[4.5]deca-3,6-diene) | 1715 | −1.4 |
| NEROL C (3,7-dimethyl-2,6-octadien-1-ol) | 1363 | −2.1 |
| NEROLEX ((Z)-3,7-dimethylocta-2,6-dien-1-ol) | 1357 | −2.2 |
| NEROLIDOL ((E)-3,7,11-trimethyldodeca-1,6,10-trien-3-ol) | 1971 | −4.5 |
| NEROLINE (2-ethoxynaphthalene) | 1294 | −1.1 |
| NEROLIONE (1-(3-methylbenzofuran-2-yl)ethanone) | 1251 | −1.7 |

-continued

| Ingredient (NAME (IUPAC name)) | RECON_VOLTAE | Log Kcaps |
|---|---|---|
| NIRVANOLIDE ((E)-13-methyloxacyclopentadec-10-en-2-one) | 1981 | −1.8 |
| NONADIENAL ((2E,6Z)-nona-2,6-dienal) | 1187 | −1.9 |
| NONADIENOL-2,6 ((2E,6Z)-nona-2,6-dien-1-ol) | 1234 | −2.5 |
| NONADIENYL ACETATE ((2E,6Z)-nona-2,6-dien-1-yl acetate) | 1520 | −2.4 |
| NONANYL ACETATE (nonanyl acetate) | 1632 | −1.7 |
| NONENOL-6-CIS ((Z)-non-6-en-1-ol) | 1263 | −2.8 |
| NOOTKATONE CRYSTALS (4,4a-dimethyl-6-(prop-1-en-2-yl)-4,4a,5,6,7,8-hexahydronaphthalen-2(3H)-one) | 1848 | −2.5 |
| NOPYL ACETATE (2-(6,6-dimethylbicyclo[3.1.1]hept-2-en-2-yl)ethyl acetate) | 1669 | −2.1 |
| OCIMENE ((E)-3,7-dimethylocta-1,3,6-triene) | 1253 | −0.7 |
| OCTALACTONE DELTA (6-propyltetrahydro-2H-pyran-2-one) | 1119 | −2.8 |
| OCTALACTONE GAMMA (5-butyloxolan-2-one) | 1128 | −3.4 |
| OCTENOL (oct-1-en-3-ol) | 1149 | −2.9 |
| OCTENYL ACETATE (oct-1-en-3-yl acetate) | 1436 | −1.8 |
| OKOUMAL (2,4-dimethyl-2-(5,5,8,8-tetramethyl-5,6,7,8-tetrahydronaphthalen-2-yl)-1,3-dioxolane) | 2422 | −2.6 |
| ONCIDAL ((E)-2,6,10-trimethylundeca-5,9-dienal) | 1833 | −2.8 |
| OPALAL (7-isopropyl-8,8-dimethyl-6,10-dioxaspiro[4.5]decane) | 1831 | −3.0 |
| ORANGER CRYSTALS (1-(2-naphtalenyl)-ethanone) | 1262 | −2.0 |
| ORCINYL 3 (3-methoxy-5-methylphenol) | 1021 | −3.0 |
| OSYROL (7-methoxy-3,7-dimethyloctan-2-ol) | 1643 | −3.2 |
| OXANE (2-methyl-4-propyl-1,3-oxathiane) | 1264 | −1.8 |
| OXYOCTALINE FORMATE (2,4a,5,8a-tetramethyl-1,2,3,4,4a,7,8,8a-octahydronaphthalen-1-yl formate) | 1974 | −2.1 |
| PANDANOL ((2-methoxyethyl)benzene) | 1081 | −1.9 |
| PARMAVERT (1,1-dimethoxynon-2-yne) | 1547 | −1.9 |
| PEACH PURE (5-heptyldihydrofuran-2(3H)-one) | 1515 | −3.9 |
| PELARGOL (3,7-dimethyloctan-1-ol) | 1438 | −2.3 |
| PEOMOSA (2-(o-tolyl)ethanol) | 1078 | −2.4 |
| PEPPERWOOD (3,7-dimethylocta-1,6-dien-3-yl dimethylcarbamate) | 1941 | −2.6 |
| PERANAT (2-methylpentyl 2-methylpentanoate) | 1719 | −0.9 |
| PETIOLE ((2-isopropoxyethyl)benzene) | 1347 | −1.5 |
| PHARAONE (2-cyclohexylhepta-1,6-dien-3-one) | 1629 | −2.3 |
| PHENOXANOL (3-methyl-5-phenylpentan-1-ol) | 1471 | −2.5 |
| PHENOXY ACETALDEHYDE (2-phenoxyacetaldehyde) | 987 | −2.9 |
| PHENOXY ETHYL ALCOHOL (2-phenoxyethanol) | 1007 | −2.9 |
| PHENOXY ETHYL ISOBUTYRATE (2-(phenoxy)ethyl 2-methylpropionate) | 1553 | −4.3 |
| PHENYL ACETALDEHYDE (2-phenyl-ethanal) | 919 | −2.5 |
| PHENYL ACETIC ACID PURE (2-phenylacetic acid) | 981 | −2.5 |
| PHENYL ETHYL ACETATE (2-phenethyl acetate) | 1237 | −1.8 |
| PHENYL ETHYL ALCOHOL (2-phenylethanol) | 951 | −2.4 |
| PHENYL ETHYL CINNAMATE (2-phenethyl 3-phenylprop-2-enoate) | 1870 | −2.9 |
| PHENYL ETHYL FORMATE (2-phenethyl formate) | 1105 | −2.1 |
| PHENYL ETHYL ISOBUTYRATE (2-phenethyl isobutanoate) | 1496 | −2.7 |
| PHENYL ETHYL ISOVALERATE (2-phenethyl 3-methylbutanoate) | 1625 | −2.2 |
| PHENYL ETHYL PHENYLACETATE (2-phenethyl 2-phenylacetate) | 1788 | −4.0 |
| PHENYL ETHYL SALICYLATE CRYSTALS (2-phenethyl 2-hydroxybenzoate) | 1721 | −5.0 |
| PHENYL PROPIONIC ALDEHYDE (3-phenylpropanal) | 1052 | −2.6 |
| PHENYL PROPYL ACETATE (3-phenylpropyl acetate) | 1367 | −1.7 |
| PHENYL PROPYL ALCOHOL (3-phenylpropan-1-ol) | 1081 | −2.3 |
| PINENE ALPHA (2,6,6-trimethylbicyclo[3.1.1]hept-2-ene) | 1196 | −0.7 |
| PINENE BETA (6,6-dimethyl-2-methylenebicyclo[3.1.1]heptane) | 1204 | −0.8 |
| PINO ACETALDEHYDE (3-(6,6-dimethylbicyclo[3.1.1]hept-2-en-2-yl)propanal) | 1483 | −4.0 |
| PIVACYCLENE ((3aR,6S,7aS)-3a,4,5,6,7,7a-hexahydro-1H-4,7-methanoinden-6-yl pivalate) | 1851 | −1.8 |
| PLICATONE ((4aS,8aR)-7-methyloctahydro-1,4-methanonaphthalen-6(2H)-one) | 1390 | −1.7 |
| POIRENATE (ethyl 2-cyclohexylpropionate) | 1499 | −1.3 |
| POMAROSE ((2E,5E)-5,6,7-trimethylocta-2,5-dien-4-one) | 1443 | −0.9 |
| PRECARONE ((1S,4R,6S)-4,7,7-trimethyl-4-(3-methylbut-2-en-1-yl)bicyclo[4.1.0]heptan-3-one) | 1887 | −3.3 |
| PRENYL ACETATE (3-methylbut-2-en-1-yl acetate) | 1039 | −2.2 |
| PROPYL DIANTILIS (2-ethoxy-4-(isopropoxymethyl)phenol) | 1606 | −2.0 |
| PRUNOLIDE (5-pentyldihydrofuran-2(3H)-one) | 1257 | −3.7 |
| QUINTONE (2-pentylcyclopentanone) | 1313 | −1.9 |
| RESEDAL (2-(cyclohexylmethyl)-4,4,6-trimethyl-1,3-dioxane) | 1726 | −1.4 |

-continued

| Ingredient (NAME (IUPAC name)) | RECON_VOLTAE | Log Kcaps |
|---|---|---|
| RHUBOFIX ((2R,8aS)-3',6-dimethyl-3,4,4a,5,8,8a-hexahydro-1H-spiro[1,4-methanonaphthalene-2,2'-oxirane]) | 1571 | −1.2 |
| RHUBOFLOR ((4aR,8aS,E)-6-ethylideneoctahydro-2H-5,8-methanochromene) | 1400 | −1.7 |
| ROSANTOLENE (1-(ethoxymethyl)-2-methoxybenzene) | 1277 | −2.2 |
| ROSAPHEN (2-methyl-5-phenylpentan-1-ol) | 1471 | −2.5 |
| ROSE OXIDE (4-methyl-2-(2-methylprop-1-en-1-yl)tetrahydro-2H-pyran) | 1320 | −2.4 |
| ROSSITOL (3-isobutyl-1-methylcyclohexanol) | 1489 | −2.3 |
| SAFRALEINE (2,3,3-trimethyl-2,3-dihydro-1H-inden-1-one) | 1390 | −1.8 |
| SAFRANAL (2,6,6-trimethylcyclohexa-1,3-dienecarbaldehyde) | 1263 | −2.4 |
| SANDELA CONCENTRATED (3-((1R,2S,4R,6R)-5,5,6-trimethylbicyclo[2.2.1]heptan-2-yl)cyclohexanol) | 1989 | −2.8 |
| SCENTENAL ((3aR,4R,6S,7R,7aR)-6-methoxyoctahydro-1H-4,7-methanoindene-1-carbaldehyde) | 1453 | −3.2 |
| SCLARENE (4,5,6,7,8,9,10,11,12,13-decahydrocyclododeca[d]oxazole) | 1680 | −1.7 |
| SHISOLIA (4-vinylcyclohex-1-enecarbaldehyde) | 1103 | −1.9 |
| SKATOLE (3-methyl-1H-indole) | 998 | −3.9 |
| SPIRAMBRENE (2',2',3,7,7-pentamethylspiro[bicyclo[4.1.0]heptane-2,5'-[1,3]dioxane]) | 2037 | −2.9 |
| STRAWBERRY PURE (ethyl methyl phenyl glycidate) | 1481 | −2.0 |
| STYRALLYL ACETATE (1-phenylethyl acetate) | 1246 | −2.0 |
| STYRALLYL PROPIONATE (1-phenylethyl propionate) | 1377 | −1.6 |
| SUPERFIX (1,1,3-trimethyl-3-phenyl-2,3-dihydro-1H-indene) | 1959 | −1.9 |
| SYRINGA ALDEHYDE (2-(p-tolyl)acetaldehyde) | 1046 | −3.0 |
| SYVERTAL (2-(heptan-3-yl)-1,3-dioxolane) | 1428 | −3.0 |
| TANAISONE ((Z)-1-(cyclooct-3-en-1-yl)ethanone) | 1275 | −1.4 |
| TANGERINOL ((E)-6,10-dimethylundeca-5,9-dien-2-yl acetate) | 2033 | −1.8 |
| TERPINENE ALPHA (1-methyl-4-propan-2-ylcyclohexa-1,3-diene) | 1194 | −0.5 |
| TERPINEOL PURE (2-(4-methylcyclohex-3-en-1-yl)propan-2-ol) | 1307 | −2.0 |
| TETRAHYDRO CITRAL (3,7-dimethyloctanal) | 1409 | −2.4 |
| TETRAHYDRO LINALYL ACETATE (3,7-dimethyloctan-3-yl acetate) | 1733 | −1.9 |
| THIOGERANIOL ((E)-3,7-dimethylocta-2,6-diene-1-thiol) | 1458 | −1.1 |
| THYMOL CRYSTALS (2-isopropyl-5-methylphenol) | 1217 | −1.8 |
| TIMBEROL (1-(2,2,6-trimethylcyclohexyl)hexan-3-ol) | 2040 | −2.1 |
| TOLYL ALDEHYDE PARA (4-methylbenzaldehyde) | 918 | −0.7 |
| TOSCANOL (1-(cyclopropylmethyl)-4-methoxybenzene) | 1261 | −1.9 |
| TRICYCLAL (2,4-dimethylcyclohex-3-enecarbaldehyde) | 1138 | −1.7 |
| TRIDECENAL-2-TRANS ((E)-tridec-2-enal) | 1744 | −2.5 |
| TRIFERNAL (3-phenylbutanal) | 1178 | −2.2 |
| TRIMOFIX O (1-((2E,5Z,9Z)-2,7,8-trimethylcyclododeca-2,5,9-trien-1-yl)ethanone) | 2093 | −3.0 |
| TROPIONAL (3-(benzo[d][1,3]dioxol-5-yl)-2-methylpropanal) | 1361 | −2.6 |
| ULTRAVANIL (2-ethoxy-4-methylphenol) | 1146 | −2.3 |
| UNDECALACTONE DELTA (6-hexyltetrahydro-2H-pyran-2-one) | 1507 | −3.3 |
| UNDECATRIENE ((3E,5Z)-undeca-1,3,5-triene) | 1379 | −0.8 |
| UNDECENE 2 NITRILE ((E)-undec-2-enenitrile) | 1559 | −1.5 |
| VALEROLACTONE GAMMA (5-methyloxolan-2-one) | 740 | −2.3 |
| VANILLIN (4-hydroxy-3-methoxybenzaldehyde) | 1043 | −3.1 |
| VANITROPE ((E)-2-ethoxy-5-(prop-1-en-1-yl)phenol) | 1363 | −1.9 |
| VELVIONE ((Z)-cyclohexadec-5-enone) | 2050 | −1.7 |
| VERDALIA ((3aS,4R,6S,7R,7aR)-6-methoxy-3a,4,5,6,7,7a-hexahydro-1H-4,7-methanoindene) | 1267 | −2.1 |
| VERDOL (2-(tert-butyl)cyclohexanol) | 1395 | −2.5 |
| VERNALDEHYDE (1-methyl-4-(4-methylpentyl)cyclohex-3-enecarbaldehyde) | 1826 | −2.3 |
| VERTOFIX COEUR (1-((1S,8aS)-1,4,4,6-tetramethyl-2,3,3a,4,5,8-hexahydro-1H-5,8a-methanoazulen-7-yl)ethanone) | 2094 | −1.9 |
| VETIKOL ACETATE/CORPS RHUBARB (4-methyl-4-phenylpentan-2-yl acetate) | 1803 | −2.4 |
| VETYNAL ((2R,5R,8S)-4,4,8-trimethyltricyclo[6.3.1.02,5]dodecan-1-yl acetate) | 2192 | −3.7 |
| VIOLET NITRILE ((2E,6Z)-nona-2,6-dienenitrile) | 1261 | −1.6 |
| VIOLIFF (undec-10-enenitrile) | 1400 | −1.5 |
| YARA YARA (2-methoxynaphthalene) | 1169 | −1.8 |

In another aspect of the present invention, there is provided a consumer product comprising an encapsulated perfume composition as herein defined.

The encapsulated perfume compositions according to the present invention can be incorporated into all manner of consumer product applications, including personal care products, such as shampoos, soaps, body washes and hair conditioners, deodorants and anti-perspirants; laundry care products such as powdered or liquid detergent compositions, scent boosters, and fabric softener or conditioning products; and household care products, such as all-purpose cleaners and dishwashing liquids, and the like.

Encapsulated perfume compositions are particularly suitable for incorporation into consumer product bases containing cationic surfactants, such as fabric conditioners or hair conditioner products.

The encapsulated perfume compositions may be incorporated into consumer products at levels that provide the consumer product with about 0.03 wt % to 1 wt % of encapsulated perfume composition based on the weight of the consumer product. The amount of encapsulated perfume composition that should be added to a consumer product base in order to arrive at this level of fragrance will depend on a number of factors, including the amount of perfume ingredients loaded into microcapsules, and the form in which the encapsulated perfume composition is incorporated into the base. Typically, the encapsulated perfume composition is incorporated in the form of a slurry containing about 20 to 50 wt %, and more particularly 30 to 45 wt % of microcapsules, wherein the microcapsules contain only perfume ingredients and no other diluents or solvents. In such a case, in order to provide the consumer product with the levels of perfume described above, one would typically incorporate between about 0.1 wt % to about 3 wt % of slurry into a consumer product base.

In a particular embodiment of the present invention, the consumer product is a fabric treatment product, such as a fabric conditioner or softener.

Fabric softener and conditioner ingredients and formulations are disclosed in U.S. Pat. Nos. 6,335,315; 5,674,832; 5,759,990; 5,877,145; and 5,574,179, which are hereby incorporated by reference.

Fabric conditioners or softeners typically comprise nitrogen-containing cationic surfactants having one or two alkyl chain comprising 16 to 22 carbon atoms, and optionally hydroxyl groups. The cationic group is preferably a quaternary ammonium, imidazolium group, and amido amine acid salts. The quaternary ammonium group has additionally two to three alkyl groups having 1 to 4 carbon or hydroxyalkyl or hydroxyl groups, or alkoxy groups, having typically about 1 to about 10 ethylene oxide moieties, and an anion selected from the group of halides, hydroxides, acetates and methylsulfate. The long alkyl chain is preferably bound to the cationic group by a ester group. Typical examples of such fabric conditioning actives include esterquat (N-methyl-N, N,bis[2-(C16-C18-acetoxy)ethyl)]-N-(2-hydroxyethyl) ammonium methosulfate), diesterquat (N,N,N-trimethyl-N-[1,2-di-(C16-C18-acyloxy)propyl ammonium salts), DEED-MAC (N,N-dimethyl-N,N-bis([2-(-[(1-oxooctadecyl)oxy] ethyl) ammonium chloride, HEQ (N,N,N-trimethyl-N—[(Z)-2-hydroxy-3-[(1-oxo-octadec-9-enyl)oxy]] ammonium chloride, TEAQ (diquaternized methylsulfate salt of the reaction product between C10-C20 staturated and unsaturated fatty acids and triethanoloamine), glycerine-based polyol esterquats, ethyl-tallowalkyl imidazolinium methyl sulphate, ditallowalkyl dimethylammonium methyl sulfate, methyl tallowalkyl amido ethyl tallowalkyl imidazolinium methyl sulfate, b-hydroxyethyl ethylenediamine erivatives, polyammonium and the like, and mixture thereof.

Further fabric softening actives are disclosed, for example, in Ajad Farooq and Charles J. Schramm, Handbook of Detergents—Part E: Applications, Surfactant Science Series 141, p. 181-200, CRC-Press, Broken Sound Parway, 2009.

Typical non-ionic surfactants that may be present in fabric conditioners or softeners include, but are not limited to alkyl and alkylbenzyl alcohol alkoxylates or polyalkoxylated carboxylic acids, polyalkoxylated amines, polyalkoxylated glycol or glycerol esters, polyalkoxylated sorbitan esters or alkanoamides.

In another embodiment of the invention, the consumer product may be a laundry detergent composition.

Laundry detergent ingredients and formulations are disclosed in U.S. Pat. Nos. 5,929,022; 5,916,862; 5,731,278; 5,470,507; 5,466,802; 5,460,752; and 5,458,810, which are hereby incorporated by reference.

Powdered or liquid detergents typically comprise anionic, zwitterionic and/or non-ionic surfactants, and mixtures thereof.

Typical anionic surfactants include sodium lauryl sulfate, sodium laureth sulfate, sodium trideceth sulfate, ammonium lauryl sulfate, ammonium laureth sulfate, potassium laureth sulfate, linear alkyl benzene sulfonates, sodium tridecyl benzene sulfonate, sodium dodecyl benzene sulfonate, sodium xylene sulfonate, monoethanolamine lauryl sulfate, monoethanolamine laureth sulfate, triethanolamine lauryl sulfate, triethanolamine laureth sulfate, lauryl sarcosine, cocoyl sarcosine, sodium lauryl sarcosinate, sodium lauroyl sarcosinate, triethylamine lauryl sulfate, triethylamine laureth sulfate, diethanolamine lauryl sulfate, diethanolamine laureth sulfate, lauric monoglyceride sodium sulfate, ammonium co-coyl sulfate, ammonium lauroyl sulfate, sodium cocoyl sulfate, sodium lauroyl sulfate, sodium cocoyl isethionate, potassium cocoyl sulfate, potassium lauryl sulfate, monoethanolamine cocoyl sulfate, monoethanolamine lauryl sulfate, triethanolamine lauryl sulfate, C5-C17 acyl-N—(C1-C4 alkyl) glucamine sulfate, C5-C17 acyl-N—(C1-C4 hydroxyalkyl) glucamine sulfate, sodium hydroxyethyl-2-decyl ether sulfates, sodium methyl-2-hydroxydecyl ether sulfates, sodium hydroxyethyl-2-dodecyl ether sulfates, sodium monoethoxylated lauryl alkyl sulfates, C12-C18 alkyl sulfonates, ethoxylated or native linear and ramified C12-C18 alcohol sulfates, ethoxylated or native linear and ramified C12-C18 alcohol sulfates, and mixtures thereof. Above anionic surfactants may also be used in their un-neutralized, acid form.

Typical non-ionic surfactants include C6-C24 alkyl ethoxylates with about 1-12 ethylene oxide units. The alkyl chain of the aliphatic alcohol can either be straight or branched, primary or secondary, and generally contains from about 6 to about 22 carbon atoms. Further examples of non-ionic surfactants include the condensation products of fatty acids with glucamines, such as C12-C16 akyl N-methyl glucamide, and/or the condensation product of fatty acids with eth-oxylated amines; C10-C20 alkyl mono- or di-alkanolamides, where the alkyloxy group has 1 to 3 carbon atoms, C10-C20 alkyl mono- or di-alknolamide having an intermediate polyoxyalkylene moiety having 2 to 20 alkyleneoxide groups between the alkyl moiety and the alkanolamide moiety; alkyl amidopropyl dimethylamine; fatty acid alkyl esters, such as sorbitol esters with oleic, myristic, stearic, palmitic acid, and the like, also known under the trade name Tween, such as Tween 20, Tween 40, and Tween 60; alkyl polyglycosides including, for example, C8-C10 alkyl polyglycosides, C12-C16 alkyl polyglycosides, C5 Amyl. Further non-ionic surfactants include glycerol-based surfactants, such as fatty acid polyglyceryl esters like octanoic acid hexaglyceryl ester, decanoic acid tetraglyceryl ester, riccinoleic acid hexaglyceryl ester and cocoic acids tetraglyceryl esters and their mixtures. The term "alkyl" as used hereinabove for the non-ionic sugar-based surfactant refers to saturated linear alkyl residues having 3 to 21 carbon atoms, including hexyl, octyl, decanyl, dodecanyl, tetradecanyl, hexa-decanyl, and octadecanyl.

Typical zwitterionic surfactants include but are not limited to derivatives of aliphatic quaternary ammonium, phosphonium, and sulfonium compounds having linear or ramified alkyl, or alkenyl, or hydroxyl alkyl or alkoxy radicals, one of which having from about 8 to about 18 carbon atoms and another of which containing an anionic group selected from carboxyl, sulfonate, sulfate, succinate, phosphate or phosphonate groups. The alkoxy radicals include typically about 1 to about 10 ethylene oxide moieties or about 1 to about 3 glyceryl moieties. The hydroxyl alkyl radicals comprise typically alkylol moieties having 1 to 3 carbon atoms. A particular class of zwitterionic surfactants includes betaines comprising a quaternized cationic ammonium group and an anionic carboxylate group, separated by at least one methylene group, such as coco dimethylcarboxymethyl betaine, lauryl dimethyl carboxymethyl betaine, lauryl dimethyl alphacarboxyethyl betaine, cetyl dimethyl carboxymethyl betaine, oleyl dimethyl gammacarboxypropyl betaine, lauryl and stearyl bis-(2-hydroxyethyl) carboxymethyl betaine, oleyl dimethyl gammacarboxypropyl betaine, and lauryl bis-(2-hydroxypropyl)alphacarboxyethyl betaine. Other betaines include amidoalkyl, sulfoalkyl and alkyl amidosufo beta-ines, wherein the alkyl moiety is typically an ethyl or a propyl moiety, such as cocoamidopropyl betaine, cocodimethylsulfopropyl betaine, lauryl dimethyl sulfoethyl betaine, lauryl bis-(2-hydroxyethyl) sulfopropyl betaine and the like. Another particular class of zwitterionic surfactants includes sultaines, hydroxysultaines and amidopropyl hydroxysultaines.

Typical Zwitterionic and semi-polar surfactants include water-soluble amine oxides, such as C10-C18 alkyl dimethyl amine oxides and C8-C12 alkoxy ethyl dihydroxy ethyl amine oxides, such as NN-dihydroxyethyl-N-stearamine oxide, ethoxylated lauramide and lauryldimethylamine oxide, also known under the name Lauramine oxide ("LO"), and alkyl amphocarboxylic acids, such as disodium cocoamphodiacetate.

Liquid or solid laundry detergent compositions may be provided in the form of single unit doses contained, for example, in water-dissolvable packaging, such as pouches or pods. Because these products are single dose and of relatively small size (typically about 10 to 20 ml volume), they are provided with a relatively low dose of detergent composition, and furthermore, because the packaging enclosing the detergent is water-soluble, or at least disintegrates readily in water, the composition necessarily contains a small volume of highly concentrated surfactant, and therefore represents a very aggressive medium in which to incorporate microcapsules.

In pouches comprising laundry, laundry additive and/or fabric conditioning compositions, the compositions may comprise one or more of the following non-limiting list of ingredients: fabric care benefit agent; detersive enzyme; deposition aid; rheology modifier; builder; bleach; bleaching agent; bleach precursor; bleach booster; bleach catalyst; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors (see: U.S. Publication No. 2003/0060390 A1, ¶65-77); cationic starches (see: US 2004/0204337 A1 and US 2007/0219111 A1); scum dispersants (see: US 2003/0126282 A1); substantive dyes; hueing dyes (see: US 2014/0162929A1); colorants; opacifier; antioxidant; hydrotropes such as toluenesulfonates, cumenesulfonates and naphthalenesulfonates; color speckles; colored beads, spheres or extrudates; clay softening agents; anti-bacterial agents. Additionally or alternatively, the compositions may comprise surfactants, quaternary ammonium compounds, and/or solvent systems.

The detergent compositions can comprise from about 1 wt % to 80 wt % by weight of a surfactant. Detersive surfactants utilized can be of the anionic, nonionic, zwitterionic or cationic type or can comprise compatible mixtures of these types. More preferably surfactants are selected from the group consisting of anionic, nonionic, cationic surfactants and mixtures thereof. Detergent surfactants useful herein are described in U.S. Pat. Nos. 3,664,961; 3,919,678; 4,222,905; and 4,239,659. Anionic and nonionic surfactants are preferred. Useful anionic, nonionic, zwitterionic or cationic type surfactants are those described above.

Laundry detergent compositions may have a pH of about 6 to about 10, about 6.5 to about 8.5, about 7 to about 7.5, or about 8 to about 10, wherein the pH of the detergent is defined as the pH of an aqueous 10% (weight/volume) solution of the detergent at 20±2° C.

In yet another embodiment of the present invention the consumer product is a personal care product, such as shampoos, hair conditioners and personal cleansing compositions. Examples of shampoos and hair conditioner formulations and ingredients are described in U.S. Pat. Nos. 6,162,423; 5,968,286; 5,935,561; 5,932,203; 5,837,661; 5,776,443; 5,756,436; 5,661,118; and 5,618,523.

Hair cleansing compositions—shampoos—comprise at least one surfactant selected from anionic, non-ionic and/or zwitterionic surfactants, typically at a concentration range of 2 to 60 wt %, more particularly 5 to 50 wt % and more particularly 5 to 40 wt % based on the total weight of the composition.

Any of the anionic, non-ionic and/or zwitterionic surfactants referred to above may be employed in hair cleansing compositions.

Anionic surfactants may be present in an amount from 1 to about 30 wt %, particularly 2 to 25 wt % and most particularly 2-20 wt %.

Non-ionic surfactants may be employed in an amount from about 0.25 wt % to about 5 wt %, particularly about 0.5 wt % to about 3.5 wt % based on the total composition.

Zwitterionic surfactants may be employed in an amount of about 0.5 wt % to about 10 wt %, more particularly from about 1 wt % to about 7.5 wt % by weight based on the total weight of the composition.

Hair conditioning compositions of the present invention can be in the form of either leave in or rinse off compositions.

Preferred surfactants are non-ionic and cationic types and they may be employed in the amounts referred to above in relation to the hair cleaning compositions.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride, and dioleoylethyl dimethyl ammonium methosulfate.

Particularly useful are so-called esterquats, which are well known commercial ingredients, such as those available under the trade names "Schercoquat™", "Dehyquart™ F30" and "Tetranyl™". Use of the esterquats in hair care compositions is described, for example, in WO-A 93/107 48, WO-A 92/068 99 and WO-A 94/166 77.

Hair conditioning compositions may contain cationic polymers as conditioning agents. Cationic conditioning agents include but are not limited to cellulose type polymers, such as Polyquaternium 10 or cationic guar gum, such as Guar hydroxypropyl trimonium chloride. Other cationic conditioning agents include natural cationic polymers, such as chitosan and chitin. Other polymers include Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, and Polyquaternium 46. Still further, Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84. It is also possible to use mixtures of various cationic polymers.

The cationic polymers may also include the quaternized products of graft polymers from organopolysiloxanes and polyethyl oxazolines, as described, for example in EP-A 524 612 and EP-A 640 643.

Typically, a hair conditioning composition might contain between 0.01 wt % to 7.5 wt %, preferably 0.05 wt % to 5 wt % of said conditioning agents based on the total weight of the composition.

Other conditioning agents might include volatile or non-volatile silicone oils, including dimethicone, dimethiconol, polydimethylsiloxane, such as the DC fluid ranges available from Dow Corning. Also suitable are natural oils, such as olive oil, almond oil, avocado oil, *ricinus* oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof, as well as mineral oils such as paraffin oil and petrolatum.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Typical concentration range for any of the additional non-cationic conditioning agents mentioned above can be 0.01 wt % to 15 wt % based on the total weight of the composition.

They may additionally contain at least one saturated or unsaturated fatty alcohol. Fatty alcohols include but are not limited to myristyl alcohol, palmityl alcohol, cetyl alcohol, stearyl alcohol, behenyl alcohol and their mixtures. The concentration of the fatty alcohol may be less than 20 wt % based on the total weight of the composition.

Conditioner compositions are disclosed in US 2015/0157550, which is hereby incorporated by reference.

In yet another embodiment of the invention, the consumer product may be a scent-booster. Scent booster products may be liquid or solid products. They are characterized in that they do not contain any actives, such as surfactants; they merely provide a suspending medium for perfume compositions, both in encapsulated form and optionally also in the form of free perfume oil. A particularly suitable suspending medium for encapsulated perfume compositions in scent booster products is polyethylene glycol (PEG). The PEG may have a molecular weight of between 5,000 to 11,000, and more particularly about 8,000.

Scent booster products are disclosed in U.S. Pat. No. 7,867,968, which is herein incorporated in its entirety.

Given the fact that scent booster products do not contain actives, such as surfactants, stability issues do not arise and so the formulator's latitude to incorporate encapsulated perfume compositions into such products is greater. Accordingly, scent booster products may contain a wider concentration range of perfume. In particular, the encapsulated perfume compositions may be applied to scent booster products at levels that provide the consumer product with up to about 5 wt % of perfume composition based on the weight of the consumer product.

There now follows a series of Examples that serve to illustrate embodiments of the present invention. It will be understood that these Examples are illustrative, and the invention is not to be considered as being restricted thereto.

Example 1

Preparation of an Ampholytic Copolymer Colloid Stabilizer

The polymer of the invention is obtained using the following protocol. The example is carried out with an acrylic acid/MAPTAC copolymer. In order to produce this polymer, the following compounds are introduced in the reactor:

464 g of MAPTAC (50% in water)
34.4 g of Acrylic acid (90% in water)
119 g of water
0.03 g of EDTA
0.14 g of sodium hypophosphite The pH of the reaction medium is adjusted at 5.0-5.2, by using NaOH.

53 g of 2,2'-azobis (2-amidinopropane) di-hydrochloride (10% in water) are also introduced in the reactor.

The reaction medium is maintained at 85° C. during 1 hour. Then 1.3 g of sodium bisulfite solution (40% in water) is added in one shot in the reactor. After 1 hour of aging, the product is diluted by adding 255 g of water.

Preparation of an Encapsulated Perfume Composition According to the Invention

One kilogram of encapsulated perfume composition slurry is formed according to the following method:

A reactor set to a temperature of 20° C. and is charged with deionised water (550 g); resorcinol as cross-linker (10 g); positively charged polymeric colloid stabilizer (2 g) prepared in accordance with the method described above; and melamine formaldehyde precondensate (Luracoll SD) (5 g). The stirring speed is set to 400 rpm. At this stage, a perfume composition (300 g) is added.

Coacervation is undertaken in the following manner: Formic acid (10%) is added and the mixture is stirred for 1 hour at 35° C. Then, the reactor temperature is increased to 90° C. for 1 hour.

Finally, the mixture is cooled. After stirring the cooled mixture for one hour, caprylyl glycol (4 g) and phenoxy ethanol (4 g) are added. A cationic suspending agent (Flosoft FS222) is added to the mixture over a 30 minute period under stirring. Finally, the pH of the slurry is adjusted to a pH range of 5.7 to 6.7 by adding a quantity of Ammonia (1 g). Thereafter, the slurry of encapsulated perfume composition is discharged from the reactor.

Example 2a

Preparation of a Comparative Encapsulated Perfume Composition Using an Anionic Polymeric Stabilizer (Lupasol PA 140)

One kilogram of encapsulated perfume composition slurry is formed according to the following method:

A reactor set to a temperature of 20° C. and is charged with deionised water (550 g); resorcinol as cross-linker (10 g); anionic polymeric colloid stabilizer Lupasol PA 140 (10 g); and melamine formaldehyde pre-condensate (Luracoll SD) (5 g). The stirring speed is set to 400 rpm At this stage, a perfume composition (300 g) is added.

Coacervation is undertaken in the following manner: Formic acid (10%) is added and the mixture is stirred for 1 hour. Then the reactor temperature is increased to 90° C. for 1 hour Finally, the mixture is cooled After stirring the cooled mixture for one hour, caprylyl glycol (4 g) and phenoxy ethanol (4 g) are added. Finally, the pH of the slurry is adjusted to a pH range of 5.7 to 6.7 by adding a quantity of Ammonia (1 g). Thereafter, the slurry of encapsulated perfume composition is discharged from the reactor.

Example 2b

Preparation of a Comparative Encapsulated Perfume Composition Using the Ampholytic Copolymer, Prepared in Accordance with the Method Described Example 1 Above, Wherein the Copolymer is Added During Crosslinking A reactor set to a temperature of 20° C. and is charged with deionised water (550 g); resorcinol as cross-linker (10 g); and melamine formaldehyde precondensate (Luracoll SD) (5 g). The stirring speed is set to 400 rpm. At this stage, a perfume composition (300 g) is added.

Coacervation is undertaken in the following manner: Formic acid (10%) is added and the mixture is stirred for 1 hour at 35° C. The reactor temperature is then increased to 90° C. and held at that temperature for 1 hour to affect cross-linking. During the increase in temperature, when the reactor temperature reaches 60° C., the positively charged ampholytic copolymer (2 g) is added to the mixture.

Finally, the mixture is cooled. After stirring the cooled mixture for one hour, caprylyl glycol (4 g) and phenoxy ethanol (4 g) are added. A cationic suspending agent (Flosoft FS222) is added to the mixture over a 30 minute period under stirring. Finally, the pH of the slurry is adjusted to a pH range of 5.7 to 6.7 by adding a quantity of Ammonia (1 g). Thereafter, the slurry of encapsulated perfume composition is discharged from the reactor.

The slurry obtained was of poor quality. D50 measurements indicated a wide particle size distribution indicating the formation of aggregates, many of which were actually visible.

Example 3

Incorporation of encapsulated perfume composition of the invention, and a comparative encapsulated perfume composition (@ 0.5% of slurry) into a fabric softener base.

The following table shows the volume average diameter (D 50) of comparative and inventive encapsulated perfume compositions. In the form of a slurry, the encapsulated perfume composition of Example 1 has a D 50 of 8 microns, whereas that of Example 2a has D 50 of 11 microns. However, when the respective compositions are incorporated into a fabric softener base, the comparative composition of Example 2a is seen to form agglomerates (D 50=100), whereas the D 50 of the inventive composition appears to be substantially unchanged (D 50=11), indicating no agglomeration. The volume average diameter is obtained by taking light scattering measurements using a Malvern 2000S instrument.

| D50 (μm) | Comparative | Invention |
|---|---|---|
| slurry | 13 | 8 |
| 0.5% Slurry in Fab softener | 100 | 11 |

Example 4

Demonstrating that the Zeta Potential on the Microcapsules is Stable Even after a Washing Step A suspension is prepared with 499.5 g of water and 0.5 g of slurry prepared according to Example 1. The suspension is agitated gently for 5 minutes to homogenize it. Thereafter, 2 grams of the suspension is added into a buffer solution ($KH_2PO_4/Na_2HPO_4$) 8 g at pH 7. The buffered solution is added to a measuring cell of a Zetasizer Nano Z instrument (Malvern), and the zeta-potential of the microcapsules is measured by the so-called phase analysis light scattering method, by directing a laser at 633 nm wavelength through the solution. The instrument gives a direct read out of microcapsule charge. The value obtained was +50 mV.

To confirm the stability of the zeta potential of the microcapsules, 5 grams of the suspension described above was mixed with the same amount of distilled water. The mixture is placed in a centrifuged and spun for 5 minutes at 2000 rpm to remove the water. The pellet was reconstituted with another 5 grams of water and then centrifuged again. The wash and centrifuge step was repeated three times. Finally, after being re-suspended, the suspension was buffered in the manner described above and the zeta potential was measured as described. It was postulated that if the positively charged polymer used in the preparation of the microcapsules was well embedded in the rnicrocapsules then it would not be washed out and the zeta potential would remain unchanged. And this proved to be the case because the zeta potential measured was again +50 mV.

Example 5

Olfactory performance of encapsulated perfume compositions according to the invention (Example 1) compared with prior art encapsulated perfume compositions of Example 2 (comparative) in a liquid fabric conditioner base.

A slurry of encapsulated perfume composition (0.5 wt % of slurry based on the weight of the base) was incorporated into a liquid fabric conditioner base. Cotton Terry towels were washed in a standard front-loading EU washing machine using an unfragranced detergent. During the rinse cycle, the towels were treated with a fabric conditioner containing encapsulated perfume composition according to example 1 (invention) and containing a comparative encapsulated perfume composition (according example 2). The towels were removed from the washing machine and line dried at room temperature for 24 h. At 24 h, the towels are folded and olfactively assessed by expert panelists (10 people). The panelists are asked to make an olfactive assessment and the results are shown in the table below (0-5 scale with the higher numbers representing the strongest olfactive performance).

| Microcapsule | Charge | D 50 (μm) | Pre-rub | Post-rub |
|---|---|---|---|---|
| Ex 2 (comparative) | Anionic | 8-10 | 2.2 | 4.2 |
| Ex 2 (comparative) | Anionic | 15-20 | 1.7 | 4.0 |

-continued

| Microcapsule | Charge | D 50 (μm) | Pre-rub | Post-rub |
|---|---|---|---|---|
| Ex 1 (invention) | Cationic | 8-10 | 3 | >5[a] |
| Ex 1 (invention) | Cationic | 15-20 | 2.2 | 4.9 |

[a] = Although the rating scale was 0-5, and so panelists could only award 5 as the highest rating, nevertheless panelists indicated that the perfume impression warranted a much higher rating The example demonstrates that the microcapsules formed according to Ex 1 are superior to those formed according to Ex 2. Furthermore, those microcapsules formed according to Ex 1 show better performance when the volume average diameter is relatively low.

Example 6

Effect of Perfume Composition on Encapsulated Perfume Composition Stability 1 g of consumer product base sample, previously filtered through a 5 micrometre syringe filter is accurately weighed in a 30 ml flask. 1 g of Celite 545 is added and admixed with the sample. 10 ml of pentane is then added together with 0.5 mg of internal standard (Methyl decanoate 99% Aldrich ref 299030) to the sample. The whole is stirred for 30 minutes using a magnetic stirrer. The pentane phase is then removed and an aliquot of 2 microlitre is injected in a gas chromatograph (GC) equipped with a splitless injector and a flame ionization detector. The initial temperature of the GC oven is 70° C., the final temperature, 240° C. and the rate of hating is set to 2° C./min. The temperature of the injector is 250° C. A RTX1 GC column with dimensions 60 m*0.25 μm*0.25 μm is used.

The table summarizes the results from capsule leakage analysis, along with RECON_VOLTAE and PROC values.

| Perfume Composition/ Application Capsules | Ingredients with RV > 1200 (wt %) | Ingredients with RV > 1540 (wt %) | Ingredients with RV > 1750 (wt %) | Total PROC | LEAKAGE 1 month 37° C. (wt %) |
|---|---|---|---|---|---|
| Fabric care softener | 96.3 | 69.6 | 21.2 | $2.0 \times 10^6$ | 20.2 |
| Fabric care softener | 99.2 | 61.0 | 4.1 | $1.8 \times 10^6$ | 14.6 |
| liquid detergent tabs | 93.8 | 66.4 | 6.5 | $2.1 \times 10^6$ | 15 |

The results show the effect of RECON_VOLTAE value distribution on microcapsule leakage. Furthermore, the results show also that it is possible to obtain perfume compositions that not only are stable under various storage conditions, while still being diffusive, as illustrated by the high tPROC values.

Example 7

A series of perfumes were encapsulated by using the process described in Example 1. In these cases, both the distribution of RECON_VOLTAE values and the total Pre-Rub Odour Contribution (tPROC) was varied. The encapsulated perfume compositions were dispersed in a liquid detergent base. Wash tests were performed after one month storage in thermostated hood at 37° C., using standard front-loaded wash machine and terry towelling as standard substrate. The pre-rub performance was evaluated by smelling the towel on dry towel, taking care not to break the capsules. A panel of 10 trained panellists was used. Both evaluation scores and characteristics of the encapsulated perfumes are reported in the table below. The following relative scale was used: 1: barely noticeable odour, 2: medium odour strength, 3: strong odour and 4: very strong odour.

TABLE

Perfume features and capsule pre-rub performance in liquid detergent tabs after storage (RV means RECON_VOLTAE and the total Pre Rub Odour Contribution (tPROC) has been divided by $10^6$ for clarity)

| RV > 1200 | RV > 1540 | RV > 1750 | pPROC/10E+6 | SCORE |
|---|---|---|---|---|
| 90.95 | 31.00 | 8.50 | 3.3 | 4 |
| 93.50 | 75.30 | 2.50 | 2.5 | 4 |
| 90.00 | 23.00 | 2.00 | 6.8 | 4 |
| 96.90 | 84.30 | 2.50 | 3.6 | 4 |
| 93.00 | 66.80 | 8.00 | 2.1 | 3 |
| 100.00 | 50.00 | 2.00 | 1.4 | 3 |
| 97.00 | 53.00 | 0.00 | 2 | 3 |
| 97.00 | 55.50 | 9.00 | 4 | 3 |
| 100.00 | 42.50 | 7.00 | 1.1 | 3 |
| 97.00 | 35.00 | 14.00 | 4.4 | 3 |
| 100.00 | 55.40 | 15.00 | 1.4 | 3 |
| 91.65 | 39.45 | 18.00 | 2 | 3 |
| 92.85 | 52.60 | 25.50 | 1 | 3 |
| 96.00 | 51.50 | 51.50 | 1.6 | 1 |
| 93.00 | 55.78 | 28.49 | 1.4 | 1 |
| 100.00 | 85.00 | 35.00 | 2 | 1 |

The results show that there is an optimum in terms of both RECON_VOLTAE distribution and t PROC distribution. The relevance of the p PROC parameter is also demonstrated. The results also show that high levels of ingredients having RECON_VOLTAE values higher than 1750 are beneficial to capsule resistance against leakage during storage, but can have a deleterious effect on pre-rub impact. The present example teaches that it is advantageous not to use RV>1750 ingredients at levels higher than 20 to 25 wt % in the encapsulated perfume composition of the present invention.

The invention claimed is:

1. An encapsulated perfume composition comprising at least one aminoplast core-shell microcapsule dispersed in a suspending medium, the at least one aminoplast microcapsule comprising a perfume-containing core, encapsulated in a shell comprising a cross-linked network of an aminoplast resin, and wherein the at least one aminoplast microcapsule is positively charged, wherein dispersed within the cross-linked network of the aminoplast resin is a positively charge polymeric colloidal stabilizer, the positively charged polymeric colloidal stabilizer being an ampholytic polymer bearing polyatomic cations with cationic units derived from a monomer bearing quaternary ammonium ion functionality, said monomer being selected from:

quaternized dimethylaminoethyl acrylate (ADAME),
quaternized dimethylaminoethyl methacrylate (MADAME),
dimethyldiallyl ammonium chloride (DADMAC),
acrylamidopropyltrimethylammonium chloride (APTAC), and
methacrylamidopropyltrimethylammonium chloride (MAPTAC).

2. The encapsulated perfume composition according to claim 1 wherein the at least one aminoplast core-shell microcapsule is not coated with a cationic deposition aid.

3. The encapsulated perfume composition according to claim 1 having a zeta potential of +50 mV+/−5 mV.

4. The encapsulated perfume composition according to claim 1, wherein the positively charged polymeric colloidal stabilizer is a terpolymer of acrylic acid, methacrylamidopropyltrimethylammonium chloride monomer and acrylamide.

5. The encapsulated perfume composition according to claim 1, wherein the suspending medium is an aqueous medium comprising a cationic suspending aid.

6. The encapsulated perfume composition according to claim 1, wherein the encapsulated perfume composition contains more than 70% wt. of perfume ingredients having known RECON_VOLTAE values larger than about 1200 $Bohr^3$.

7. The encapsulated perfume composition according to claim 1, forming a part of a personal care, household care or fabric care product.

8. A personal care, household care or fabric care product containing the encapsulated perfume composition according to claim 1.

9. The encapsulated perfume composition according to claim 1, wherein the positively charged polymeric colloidal stabilizer is an ampholytic copolymer formed from acrylic acid or methacrylic acid, and acrylamidopropyltrimethylammonium chloride (APTAC) or methacrylamidopropyltrimethylammonium chloride (MAPTAC).

10. The encapsulated perfume composition according to claim 6, wherein 30 wt. % or more of the perfume ingredients have known RECON VOLTAE values larger than 1540 $Bohr^3$, and 30 wt % or more of perfume ingredients have known RECON VOLTAE values from 1200 $Bohr^3$ to 1540 $Bohr^3$, and from 0.1 to 30 wt. % of perfume ingredients have known RECON VOLTAE values below 1200 $Bohr^3$.

11. The encapsulated perfume composition according to claim 6, wherein 0.5 to 30 wt. % or more of perfume ingredients have known RECON VOLTAE values above 1750 $Bohr^3$, and 20 to 60 wt. % of perfume ingredients have known RECON VOLTAE values from 1540 $Bohr^3$ to 1750 $Bohr^3$, and 5 to 50 wt. % of perfume ingredients have known RECON VOLTAE values from 1200 $Bohr^3$ to 1540 $Bohr^3$, and from 0.1 to 30 wt. % of perfume ingredients have known RECON VOLTAE values below 1200 $Bohr^3$.

12. A method of forming the encapsulated perfume composition according to claim 1, said method comprising the step of:
    forming a dispersion of at least one perfume-containing droplet in a suspending medium in the presence of a positively-charged polymeric colloidal stabilizer, and thereafter;
    causing an encapsulating shell of cross-linked aminoplast resin to form around said at least one droplet thereby forming the at least one aminoplast microcapsule comprising a perfume-containing core.

13. The method according to claim 12, comprising the steps of:—
    a) providing an aqueous phase comprising a positively charged polymeric colloidal stabilizer, a shell-forming melamine formaldehyde pre-condensate and optionally a cross-linker;
    b) providing an oil phase comprising the perfume-containing droplet to be encapsulated;
    c) mixing the aqueous phase and the oil phase in a reactor to form an emulsion comprising perfume-containing droplets dispersed in an aqueous external phase;
    d) adjusting the pH and temperature within the reactor to initiate coacervation and shell formation around the droplets thereby to form core-shell microcapsules; and
    e) adjusting temperature within the reactor to initiate cross-linking and harden the shells of said core-shell capsules, before cooling to form the at least one aminoplast microcapsule comprising a perfume-containing core in the form of a slurry.

14. The method according to claim 13 wherein the slurry comprises a cationic suspending agent.

15. A method of incorporating the encapsulated perfume composition formed according to the method of claim 12 into a consumer product, the method comprising the steps of:
    providing a formed encapsulated perfume composition, and mixing a slurry into the consumer product.

16. The method according to claim 15, wherein the D50 of the microcapsules in the encapsulated perfume composition is 5 to 50 microns and the D50 of the microcapsules incorporated into the consumer product is 5 to 50 microns.

17. An encapsulated perfume composition produced by the process of claim 12.

18. The method according to claim 16, wherein the D50 of the microcapsules in the encapsulated perfume composition is 5 to 20 microns.

19. The method according to claim 16, wherein the D50 of the microcapsules incorporated into the consumer product is 5 to 20 microns.

* * * * *